United States Patent
Yahagi et al.

(10) Patent No.: US 11,693,313 B2
(45) Date of Patent: *Jul. 4, 2023

(54) RESIST COMPOSITION AND METHOD OF FORMING RESIST PATTERN

(71) Applicant: TOKYO OHKA KOGYO CO., LTD., Kawasaki (JP)

(72) Inventors: Masahito Yahagi, Kawasaki (JP); Takahiro Kojima, Kawasaki (JP)

(73) Assignee: Tokyo Ohka Kogyo Co., Ltd., Kawasaki (JP)

( * ) Notice: Subject to any disclaimer, the term of this patent is extended or adjusted under 35 U.S.C. 154(b) by 298 days.

This patent is subject to a terminal disclaimer.

(21) Appl. No.: 17/094,636

(22) Filed: Nov. 10, 2020

(65) Prior Publication Data
US 2021/0149302 A1    May 20, 2021

(30) Foreign Application Priority Data
Nov. 14, 2019   (JP) .................. 2019-206432

(51) Int. Cl.
| | | |
|---|---|---|
| G03F 7/004 | (2006.01) | |
| G03F 7/038 | (2006.01) | |
| G03F 7/039 | (2006.01) | |
| C08F 220/18 | (2006.01) | |
| C08F 212/14 | (2006.01) | |
| C07C 65/05 | (2006.01) | |

(52) U.S. Cl.
CPC ............ *G03F 7/0045* (2013.01); *C07C 65/05* (2013.01); *C08F 212/24* (2020.02); *C08F 220/1806* (2020.02); *C08F 220/1807* (2020.02); *C08F 220/1808* (2020.02); *C08F 220/1811* (2020.02); *C08F 220/1818* (2020.02); *G03F 7/038* (2013.01); *G03F 7/039* (2013.01)

(58) Field of Classification Search
CPC .............. C08F 220/1818; C08F 220/30; C08F 220/1807; C08F 220/1806; C08F 220/1808; C08F 220/1811; C08F 212/24; C07C 65/05; G03F 7/004; G03F 7/0045
See application file for complete search history.

(56) References Cited

U.S. PATENT DOCUMENTS

| | | | |
|---|---|---|---|
| 6,949,325 B2 | 9/2005 | Li et al. | |
| 8,785,106 B2* | 7/2014 | Komuro | G03F 7/0397 430/326 |
| 11,275,306 B2* | 3/2022 | Kojima | G03F 7/0045 |
| 2001/0049073 A1 | 12/2001 | Hada et al. | |
| 2004/0110085 A1 | 6/2004 | Iwai et al. | |
| 2008/0187860 A1 | 8/2008 | Tsubaki et al. | |
| 2009/0317743 A1 | 12/2009 | Shiono et al. | |
| 2013/0095427 A1 | 4/2013 | Yahagi et al. | |
| 2013/0189619 A1 | 7/2013 | Komuro et al. | |
| 2016/0209745 A1 | 7/2016 | Hirayama | |
| 2017/0003591 A1 | 1/2017 | Mochizuki et al. | |
| 2017/0351177 A1* | 12/2017 | Hatakeyama | G03F 7/0048 |

(Continued)

FOREIGN PATENT DOCUMENTS

| | | |
|---|---|---|
| JP | 2000-206694 | 7/2000 |
| JP | 2003-241385 | 8/2003 |

(Continued)

OTHER PUBLICATIONS

Machine translation of WO 2020/195428 (no date).*

(Continued)

*Primary Examiner* — Amanda C. Walke
(74) *Attorney, Agent, or Firm* — Knobbe, Martens, Olson & Bear, LLP

(57) ABSTRACT

A resist composition including a compound (D0) represented by general formula (d0) and a polymeric compound (A10) having a structural unit (a0) derived from a compound represented by general formula (a0-1) shown below (in formula (d0), n represents an integer of 2 or more; in formula (a0-1), $W^1$ represents a polymerizable group-containing group; $C^t$ represents a tertiary carbon atom, and the α-position of $C^t$ is a carbon atom which constitutes a carbon-carbon unsaturated bond; $R^{11}$ represents an aromatic hydrocarbon group which may have a substituent, or a chain hydrocarbon group; $R^{12}$ and $R^{13}$ each independently represents a chain hydrocarbon group, or $R^{12}$ and $R^{13}$ are mutually bonded to form a cyclic group

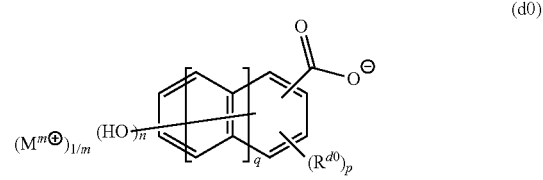

(d0)

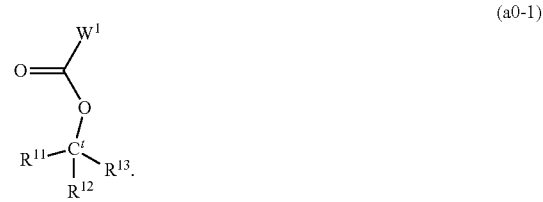

(a0-1)

7 Claims, No Drawings

(56) References Cited

U.S. PATENT DOCUMENTS

| | | | |
|---|---|---|---|
| 2020/0183273 A1 | 6/2020 | Nguyen et al. | |
| 2020/0183275 A1* | 6/2020 | Kojima | G03F 7/0392 |
| 2021/0149302 A1 | 5/2021 | Yahagi et al. | |
| 2021/0149303 A1* | 5/2021 | Kojima | G03F 7/0392 |
| 2021/0364918 A1 | 11/2021 | Nishikori et al. | |
| 2022/0121118 A1 | 4/2022 | Yahagi et al. | |

FOREIGN PATENT DOCUMENTS

| | | | |
|---|---|---|---|
| JP | 2005-336452 | 12/2005 | |
| JP | 2006-259582 | 9/2006 | |
| JP | 2006-317803 | 11/2006 | |
| JP | 2008-292975 | 12/2008 | |
| JP | 2010-002870 | 1/2010 | |
| JP | 2010-066492 | 3/2010 | |
| JP | 2014-115386 A | 6/2014 | |
| WO | WO-2020195428 A1 * | 10/2020 | C07C 381/12 |

OTHER PUBLICATIONS

Office Action issued in U.S. Appl. No. 13/772,658, dated Nov. 4, 2013.

Notice of Allowance issued in U.S. Appl. No. 13/772,658, dated Mar. 14, 2014.

Requirement for Restriction/Election issued in U.S. Appl. No. 16/686,712, dated Apr. 2, 2021.

Office Action issued in U.S. Appl. No. 16/686,712, dated May 13, 2021.

Notice of Allowance issued in U.S. Appl. No. 16/686,712, dated Nov. 15, 2021.

Office Action issued in U.S. Appl. No. 17/094,661, dated Jun. 15, 2022.

Final Office Action issued in U.S. Appl. No. 17/094,661, dated Dec. 5, 2022.

* cited by examiner

RESIST COMPOSITION AND METHOD OF FORMING RESIST PATTERN

TECHNICAL FIELD

The present invention relates to a resist composition and a method of forming a resist pattern.

Priority is claimed on Japanese Patent Application No. 2019-206432, filed Nov. 14, 2019, the content of which is incorporated herein by reference.

DESCRIPTION OF RELATED ART

In recent years, in the production of semiconductor elements and liquid crystal display elements, advances in lithography techniques have led to rapid progress in the field of pattern miniaturization. Typically, these miniaturization techniques involve shortening the wavelength (increasing the energy) of the exposure light source.

Resist materials for use with these types of exposure light sources require lithographic properties such as a high resolution capable of reproducing patterns of minute dimensions, and a high level of sensitivity to these types of exposure light sources.

As a resist material that satisfies these conditions, a chemically amplified composition is used, which includes a base material component that exhibits a changed solubility in a developing solution under the action of acid and an acid-generator component that generates acid upon exposure.

In the formation of a resist pattern, it is considered that the behavior of the acid generated from the acid-generator component upon exposure is one of the factors that has a large influence on the lithography properties.

In consideration of the above, there has been proposed a chemically amplified resist composition which uses, in combination with an acid generator component, an acid diffusion control agent which controls the diffusion of acid generated from the acid generator component upon exposure.

For example, Patent Literature 1 discloses a resist composition including a base component which exhibits changed solubility in a developing solution by the action of acid, an acid-generator component, and a photoreactive quencher having a cation moiety with a specific structure as an acid diffusion control agent. The photoreactive quencher goes under an ion exchange reaction with the acid generated from the acid generator component to exhibit a quenching effect. By including a photoreactive quencher, acid generated from the acid generator component can be suppressed from being diffused from exposed portions of the resist film to unexposed portions of the resist film. As a result, lithography properties can be improved.

DOCUMENTS OF RELATED ART

Patent Literature

[Patent Document 1] Japanese Unexamined Patent Application, First Publication No. 2014-115386

SUMMARY OF THE INVENTION

Recently, advances in lithography techniques and expansion in the application fields have led to rapid progress in the field of pattern miniaturization. As a consequence, in the production of a semiconductor device or the like, there is a demand for a technique which enable formation of a fine resist pattern having a pattern width of no more than 100 nm with good shape.

However, using a conventional resist composition as described in Patent Literature 1, it was difficult to achieve both high sensitivity and improved lithography properties.

The present invention takes the above circumstances into consideration, with an object of providing a resist composition which exhibits improved sensitivity and lithography properties and is capable of forming a resist pattern with a high rectangularity, and a method of forming a resist pattern using the resist composition.

For solving the above-mentioned problems, the present invention employs the following aspects.

Specifically, a first aspect of the present invention is a resist composition which generates acid upon exposure and exhibits changed solubility in a developing solution under action of acid, the resist composition including: a resin component (A1) which exhibits changed solubility in a developing solution under action of acid, and a compound (D0) represented by general formula (d0) shown below having a cation moiety and an anion moiety, the resin component (A1) including a polymeric compound (A10) having a structural unit (a0) derived from a compound represented by general formula (a0-1) shown below.

[Chemical Formula 1]

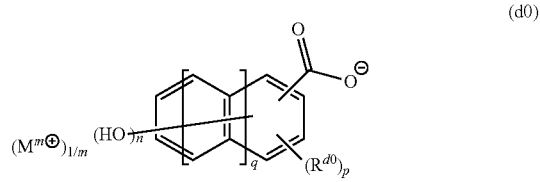

In the formula, $M^{m+}$ represents an m-valent organic cation; m represents an integer of 1 or more. $R^{d0}$ represents a substituent; p represents an integer of 0 to 3; when p is 2 or 3, the plurality of $R^{d0}$ may be the same or different from each other; q represents an integer of 0 to 3; n represents an integer of 2 or more; provided that $n+p \leq (q \times 2)+5$.

A second aspect of the present invention is a method of forming a resist pattern, including: using a resist composition according to the first aspect to form a resist film, exposing the resist film, and developing the exposed resist film to form a resist pattern.

According to the present invention, there are provided a resist composition which exhibits improved sensitivity and lithography properties, and which is capable of forming a resist pattern with a high rectangularity; and a method of forming a resist pattern using the resist composition.

DETAILED DESCRIPTION OF THE INVENTION

In the present description and claims, the term "aliphatic" is a relative concept used in relation to the term "aromatic", and defines a group or compound that has no aromaticity.

The term "alkyl group" includes linear, branched or cyclic, monovalent saturated hydrocarbon, unless otherwise specified. The same applies for the alkyl group within an alkoxy group.

The term "alkylene group" includes linear, branched or cyclic, divalent saturated hydrocarbon, unless otherwise specified.

Examples of the halogen atom include a fluorine atom, a chlorine atom, a bromine atom and an iodine atom. The term "structural unit" refers to a monomer unit that contributes to the formation of a polymeric compound (resin, polymer, copolymer).

The case of describing "may have a substituent" includes both of the case where the hydrogen atom (—H) is substituted with a monovalent group and the case where a methylene group (—CH$_2$—) is substituted with a divalent group.

The term "exposure" is used as a general concept that includes irradiation with any form of radiation.

The term "acid decomposable group" refers to a group in which at least a part of the bond within the structure thereof is cleaved by the action of an acid.

Examples of acid decomposable groups which exhibit increased polarity by the action of an acid include groups which are decomposed by the action of an acid to form a polar group.

Examples of the polar group include a carboxy group, a hydroxy group, an amino group and a sulfo group (—SO$_3$H).

More specifically, as an example of an acid decomposable group, a group in which the aforementioned polar group has been protected with an acid dissociable group (such as a group in which the hydrogen atom of the OH-containing polar group has been protected with an acid dissociable group) can be given.

The "acid dissociable group" refers to both (i) a group in which the bond between the acid dissociable group and the adjacent atom is cleaved by the action of acid; and (ii) a group in which one of the bonds is cleaved by the action of acid, and then a decarboxylation reaction occurs, thereby cleaving the bond between the acid dissociable group and the adjacent atom.

It is necessary that the acid dissociable group that constitutes the acid decomposable group is a group which exhibits a lower polarity than the polar group generated by the dissociation of the acid dissociable group. Thus, when the acid dissociable group is dissociated by the action of acid, a polar group exhibiting a higher polarity than that of the acid dissociable group is generated, thereby increasing the polarity. As a result, the polarity of the entire component (A1) is increased. By the increase in the polarity, the solubility in an alkali developing solution changes, and the solubility in an alkali developing solution is relatively increased, whereas the solubility in an organic developing solution is relatively decreased.

The term "base component" refers to an organic compound capable of forming a film. The organic compound used as the base component is broadly classified into non-polymers and polymers. In general, as a non-polymer, any of those which have a molecular weight in the range of 500 to less than 4,000 is used. Hereafter, a "low molecular weight compound" refers to a non-polymer having a molecular weight in the range of 500 to less than 4,000. As a polymer, any of those which have a molecular weight of 1,000 or more is generally used. Hereafter, a "resin" or a "polymer" refers to a polymer having a molecular weight of 1,000 or more. As the molecular weight of the polymer, the weight average molecular weight in terms of the polystyrene equivalent value determined by gel permeation chromatography (GPC) is used.

The expression "structural unit derived from" refers to a structural unit which is formed by cleavage of a multiple bond between carbon atoms, e.g., an ethylenic double bond.

The acrylate ester may have the hydrogen atom bonded to the carbon atom on the α-position substituted with a substituent. The substituent ($R^{\alpha x}$) that substitutes the hydrogen atom bonded to the carbon atom on the α-position is an atom other than hydrogen or a group. Further, an acrylate ester having the hydrogen atom bonded to the carbon atom on the α-position substituted with a substituent ($R^{\alpha x}$) in which the substituent has been substituted with a substituent containing an ester bond (e.g., an itaconic acid diester), or an acrylic acid having the hydrogen atom bonded to the carbon atom on the α-position substituted with a substituent ($R^{\alpha x}$) in which the substituent has been substituted with a hydroxyalkyl group or a group in which the hydroxy group within a hydroxyalkyl group has been modified (e.g., α-hydroxyalkyl acrylate ester) may be mentioned as an acrylate ester having the hydrogen atom bonded to the carbon atom on the α-position substituted with a substituent. A carbon atom on the α-position of an acrylate ester refers to the carbon atom bonded to the carbonyl group, unless specified otherwise.

Hereafter, an acrylate ester having the hydrogen atom bonded to the carbon atom on the α-position substituted with a substituent is sometimes referred to as "α-substituted acrylate ester".

The term "derivative" is a concept including a compound in which a hydrogen atom at the α-position of the subject compound has been substituted with another substituent such as an alkyl group or a halogenated alkyl group, and derivatives thereof. Examples of the derivatives include a compound in which the hydrogen atom at the α-position of the subject compound may be substituted with a substituent, and the hydrogen atom of the hydroxy group of the target compound has been substituted with an organic group; and a compound in which the hydrogen atom at the α-position of the subject compound may be substituted with a substituent, and a substituent other than a hydroxy group has been bonded to the subject compound. The α-position refers to the first carbon atom adjacent to a functional group, unless otherwise specified.

As the substituent which substitutes the hydrogen atom on the α-position of hydroxystyrene, the same substituents as those described above for $R^{\alpha x}$ may be mentioned.

In the present specification and claims, some structures represented by chemical formulae may have an asymmetric carbon, such that an enantiomer or a diastereomer may be present. In such a case, the one formula represents all isomers. The isomers may be used individually, or in the form of a mixture.

(Resist Composition)

The resist composition of the present embodiment generates acid upon exposure and exhibits changed solubility in a developing solution under action of acid.

In one embodiment, the resist composition may include the component (A) and a basic component (hereafter, sometimes referred to as "component (D)") which suppresses diffusion of acid generated upon exposure. Preferably, the resist composition contains, in addition to the component (A) and the component (D), an acid-generator component (B) (hereafter, also referred to as "component (B)") which generates acid upon exposure.

When a resist film is formed using the resist composition according to the present embodiment, and the resist film is selectively exposed, acid is generated at exposed portions of the resist film, and the solubility of the component (A) in a developing solution is changed by the action of the acid. On the other hand, at unexposed portions of the resist film, the solubility of the component (A) in a developing solution is unchanged. As a result, difference is generated between the exposed portions of the resist film and the unexposed portions of the resist film in terms of solubility in a developing solution.

The resist composition of the present embodiment may be either a positive resist composition or a negative resist composition.

Further, the resist composition of the present embodiment may be applied to an alkali developing process using an alkali developing solution in the developing treatment in the formation of a resist pattern, or a solvent developing process using a developing solution containing an organic solvent (organic developing solution) in the developing treatment.

That is, the resist composition of the present embodiment is preferably a resist composition which forms a positive pattern in an alkali developing process (i.e., a positive resist compound for alkali developing process) or a resist composition which forms a negative pattern in a solvent developing process (i.e., a negative type resist composition for solvent developing process).

<Component (A)>

In the resist composition of the present embodiment, the component (A) includes a resin component (A1) (hereafter, sometimes referred to as "component (A1)") which exhibits changed solubility in a developing solution by the action of acid, and the component (A1) includes a polymeric compound (A10) having a structural unit (a0) derived from a compound represented by general formula (a0-1) shown below.

As the component (A), at least the component (A1) is used, and at least one of another polymeric compound and a low molecular weight compound may be used in combination with the component (A1).

In the resist composition of the present embodiment, as the component (A), one kind of compound may be used, or two or more kinds of compounds may be used in combination.

—Component (A1)

The component (A1) includes a polymeric compound (A10) having a structural unit (a0).

<<Structural Unit (a0)>>

The structural unit (a0) is a structural unit derived from a compound represented by general formula (a0-1) shown below.

[Chemical Fromula 2]

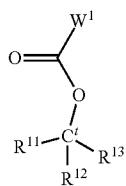

(a0-1)

In formula (a0-1), $W^1$ represents a polymerizable group-containing group; $C^t$ represents a tertiary carbon atom, and the α-position of $C^t$ is a carbon atom which constitutes a carbon-carbon unsaturated bond; $R^{11}$ represents an aromatic hydrocarbon group which may have a substituent, or a chain hydrocarbon group; $R^{12}$ and $R^{13}$ each independently represents a chain hydrocarbon group which may have a substituent, or $R^{12}$ and $R^{13}$ are mutually bonded to form a cyclic group which may have a substituent.

In general formula (a0-1), $W^1$ represents a polymerizable group-containing group.

The "polymerizable group" for $W^1$ is a group which can cause a compound having the polymerizable group to be polymerized by radical polymerization or the like. Examples of the polymerizable group include a group containing a multiple bond between carbon atoms such as an ethylenic double bond.

In the structural unit (a0), the multiple bond in the polymerizable group of the compound represented by the aforementioned general formula (a0-1) is cleaved to form a main chain.

Examples of the polymerizable group include a vinyl group, an allyl group, an acryloyl group, a methacryloyl group, a fluorovinyl group, a difluorovinyl group, a trifluorovinyl group, a difluorotrifluoromethylvinyl group, a trifluoroallyl group, a perfluoroallyl group, a trifluoromethylacryloyl group, a nonylfluorobutylacryloyl group, a vinyl ether group, a fluorine-containing vinyl ether group, an allyl ether group, an fluorine-containing allyl ether group, a styryl group, a vinylnaphthyl group, a fluorine-containing styryl group, a fluorine-containing vinylnaphthyl group, a norbornyl group, a fluorine-containing norbornyl group, and a silyl group.

The polymerizable group-containing group may be a group constituted of only a polymerizable group, or a group constituted of a polymerizable group and a group other than a polymerizable group. Examples of the group other than a polymerizable group include a divalent hydrocarbon group which may have a substituent, and a divalent linking group containing a hetero atom (provided that oxygen is excluded). However, the polymerizable group-containing group $W^1$ contains no oxygen.

Preferable examples of $W^1$ include a group represented by the chemical formula:

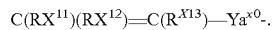

$$C(RX^{11})(RX^{12})=C(R^{X13})-Ya^{x0}-.$$

In the chemical formula, $R^{X11}$, $R^{X12}$ and $R^{X13}$ independently represents a hydrogen atom, an alkyl group having 1 to 5 carbon atoms or a halogenated alkyl group having 1 to 5 carbon atoms, and $Ya^{x0}$ represents a single bond or a divalent linking group.

In formula (a0-1), as the alkyl group of 1 to 5 carbon atoms for $R^{X11}$, $R^{X12}$ and $R^{X13}$, a linear or branched alkyl group of 1 to 5 carbon atoms is preferable, and specific examples thereof include a methyl group, an ethyl group, a propyl group, an isopropyl group, an n-butyl group, an isobutyl group, a tert-butyl group, a pentyl group, an isopentyl group and a neopentyl group. The halogenated alkyl group of 1 to 5 carbon atoms represented by R is a group in which part or all of the hydrogen atoms of the aforementioned alkyl group of 1 to 5 carbon atoms have been substituted with halogen atoms. As the halogen atom, a fluorine atom is most preferable.

Among these examples, as $R^{X11}$ and $R^{X12}$ a hydrogen atom, an alkyl group of 1 to 5 carbon atoms or a fluorinated alkyl group of 1 to 5 carbon atoms is preferable, and in terms of industrial availability, a hydrogen atom or a methyl group is more preferable, and a hydrogen atom is still more preferable.

As $R^{X13}$, a hydrogen atom, an alkyl group of 1 to 5 carbon atoms or a fluorinated alkyl group of 1 to 5 carbon atoms is preferable, and in terms of industrial availability, a hydrogen atom or a methyl group is more preferable.

In the formula (a0-1), the divalent linking group for $Ya^{x0}$ is not particularly limited, and preferable examples thereof include a divalent hydrocarbon group which may have a substituent and a divalent linking group containing a hetero atom.

—Divalent Hydrocarbon Group which May have a Substituent:

In the case where $Ya^{x0}$ is a divalent linking group which may have a substituent, the hydrocarbon group may be either an aliphatic hydrocarbon group or an aromatic hydrocarbon group.

—Aliphatic Hydrocarbon Group for $Ya^{x0}$

The "aliphatic hydrocarbon group" refers to a hydrocarbon group that has no aromaticity. The aliphatic hydrocarbon group may be saturated or unsaturated. In general, the aliphatic hydrocarbon group is preferably saturated. Examples of the aliphatic hydrocarbon group include a linear or branched aliphatic hydrocarbon group, and an aliphatic hydrocarbon group containing a ring in the structure thereof can be given.

—Linear or Branched Aliphatic Hydrocarbon Group

The linear aliphatic hydrocarbon group preferably has 1 to 10 carbon atoms, more preferably 1 to 6, still more preferably 1 to 4, and most preferably 1 to 3.

As the linear aliphatic hydrocarbon group, a linear alkylene group is preferable. Specific examples thereof include a methylene group [—$CH_2$—], an ethylene group [—$(CH_2)_2$—], a trimethylene group [—$(CH_2)_3$—], a tetramethylene group [—$(CH_2)_4$—] and a pentamethylene group [—$(CH_2)_5$—].

The branched aliphatic hydrocarbon group preferably has 2 to 10 carbon atoms, more preferably 3 to 6, still more preferably 3 or 4, and most preferably 3.

As the branched aliphatic hydrocarbon group, branched alkylene groups are preferred, and specific examples include various alkylalkylene groups, including alkylmethylene groups such as —$CH(CH_3)$—, —$CH(CH_2CH_3)$—, —$C(CH_3)_2$—, —$C(CH_3)(CH_2CH_3)$—, —$C(CH_3)(CH_2CH_2CH_3)$—, and —$C(CH_2CH_3)_2$—; alkylethylene groups such as —$CH(CH_3)CH_2$—, —$CH(CH_3)CH(CH_3)$—, —$C(CH_3)_2CH_2$—, —$CH(CH_2CH_3)CH_2$—, and —$C(CH_2CH_3)_2$—$CH_2$—; alkyltrimethylene groups such as —$CH(CH_3)CH_2CH_2$—, and —$CH_2CH(CH_3)CH_2$—; and alkyltetramethylene groups such as —$CH(CH_3)CH_2CH_2CH_2$—, and —$CH_2CH(CH_3)CH_2CH_2$—. As the alkyl group within the alkylalkylene group, a linear alkyl group of 1 to 5 carbon atoms is preferable.

The linear or branched aliphatic hydrocarbon group may or may not have a substituent. Examples of the substituent include a fluorine atom, a fluorinated alkyl group of 1 to 5 carbon atoms, and a carbonyl group.

—Aliphatic Hydrocarbon Group Containing a Ring in the Structure Thereof

As examples of the hydrocarbon group containing a ring in the structure thereof, an alicyclic hydrocarbon group (a group in which two hydrogen atoms have been removed from an aliphatic hydrocarbon ring) which may contain a hetero atom in the ring structure thereof, a group in which the alicyclic hydrocarbon group is bonded to the terminal of the aforementioned chain-like aliphatic hydrocarbon group, and a group in which the alicyclic group is interposed within the aforementioned linear or branched aliphatic hydrocarbon group, may be given. The linear or branched aliphatic hydrocarbon group is the same as defined above.

The cyclic aliphatic hydrocarbon group preferably has 3 to 20 carbon atoms, and more preferably 3 to 12 carbon atoms.

The cyclic aliphatic hydrocarbon group may be either a polycyclic group or a monocyclic group. As the monocyclic aliphatic hydrocarbon group, a group in which 2 hydrogen atoms have been removed from a monocycloalkane is preferable. The monocycloalkane preferably has 3 to 6 carbon atoms, and specific examples thereof include cyclopentane and cyclohexane. As the polycyclic group, a group in which 2 hydrogen atoms have been removed from a polycycloalkane is preferable, and the polycyclic group preferably has 7 to 12 carbon atoms. Examples of the polycycloalkane include adamantane, norbornane, isobornane, tricyclodecane and tetracyclododecane.

The cyclic aliphatic hydrocarbon group may or may not have a substituent. Examples of the substituent include an alkyl group, an alkoxy group, a halogen atom, a halogenated alkyl group, a hydroxyl group and a carbonyl group.

The alkyl group as the substituent is preferably an alkyl group of 1 to 5 carbon atoms, and a methyl group, an ethyl group, a propyl group, an n-butyl group or a tert-butyl group is particularly desirable.

The alkoxy group as the substituent is preferably an alkoxy group having 1 to 5 carbon atoms, more preferably a methoxy group, ethoxy group, n-propoxy group, isopropoxy group, n-butoxy group or tert-butoxy group, and most preferably a methoxy group or an ethoxy group.

The halogen atom as the substituent is preferably a fluorine atom.

Examples of the halogenated alkyl group for the substituent include groups in which part or all of the hydrogen atoms within the aforementioned alkyl groups has been substituted with the aforementioned halogen atoms.

The cyclic aliphatic hydrocarbon group may have part of the carbon atoms constituting the ring structure thereof substituted with a substituent containing a hetero atom. As the substituent containing a hetero atom, —O—, —C(=O)—O—, —S—, —S(=O)$_2$— or —S(=O)$_2$—O— is preferable.

—Aromatic hydrocarbon group for $Ya^{x0}$

The aromatic hydrocarbon group is a hydrocarbon group having at least one aromatic ring.

The aromatic ring is not particularly limited, as long as it is a cyclic conjugated compound having (4n+2)π electrons, and may be either monocyclic or polycyclic. The aromatic ring preferably has 5 to 30 carbon atoms, more preferably 5 to 20 carbon atoms, and still more preferably 6 to 15 carbon atoms, and most preferably 6 to 12 carbon atoms. Here, the number of carbon atoms within a substituent(s) is not included in the number of carbon atoms of the aromatic hydrocarbon group. Examples of the aromatic ring include aromatic hydrocarbon rings, such as benzene, naphthalene, anthracene and phenanthrene; and aromatic hetero rings in which part of the carbon atoms constituting the aforementioned aromatic hydrocarbon rings has been substituted with a hetero atom. Examples of the hetero atom within the aromatic hetero rings include an oxygen atom, a sulfur atom and a nitrogen atom. Specific examples of the aromatic hetero ring include a pyridine ring and a thiophene ring.

Specific examples of the aromatic hydrocarbon group include a group in which two hydrogen atoms have been removed from the aforementioned aromatic hydrocarbon ring or aromatic hetero ring (arylene group or heteroarylene group); a group in which two hydrogen atoms have been removed from an aromatic compound having two or more aromatic rings (biphenyl, fluorene or the like); and a group in which one hydrogen atom of the aforementioned aromatic hydrocarbon ring or aromatic hetero ring has been substituted with an alkylene group (a group in which one hydrogen atom has been removed from the aryl group within the aforementioned arylalkyl group such as a benzyl group, a phenethyl group, a 1-naphthylmethyl group, a 2-naphthylmethyl group, a 1-naphthylethyl group, or a 2-naphthylethyl group, or a heteroarylalkyl group). The alkylene group which is bonded to the aforementioned aryl group or heteroaryl group preferably has 1 to 4 carbon atoms, more preferably 1 or 2 carbon atoms, and most preferably 1 carbon atom.

With respect to the aromatic hydrocarbon group, the hydrogen atom within the aromatic hydrocarbon group may be substituted with a substituent. For example, the hydrogen atom bonded to the aromatic ring within the aromatic hydrocarbon group may be substituted with a substituent. Examples of substituents include an alkyl group, an alkoxy group, a halogen atom, a halogenated alkyl group, and a hydroxyl group.

The alkyl group as the substituent is preferably an alkyl group of 1 to 5 carbon atoms, and a methyl group, an ethyl group, a propyl group, an n-butyl group or a tert-butyl group is particularly desirable.

As the alkoxy group, the halogen atom and the halogenated alkyl group for the substituent, the same groups as the aforementioned substituent groups for substituting a hydrogen atom within the cyclic aliphatic hydrocarbon group can be used.

—Divalent Linking Group Containing a Hetero Atom

In the case where $Ya^{x0}$ is a divalent linking group containing a hetero atom, examples of the linking group include —O—, —C(=O)—O—, —C(=O)-, —O—C(=O)—O—, —C(=O)—NH—, —NH—, —NH—C(=NH)— (H may be substituted with an alkyl group, an acyl group or the like), —S—, —S(=O)$_2$—, —S(=O)$_2$—O—, and a group represented by general formula —$Y^{21}$—O—$Y^{22}$—, —$Y^{21}$—O—, —$Y^{21}$—C(=O)—O—, —C(=O)—O—$Y^{21}$—, —[$Y^{21}$—C(=O)—O]$_{m''}$—$Y^{22}$—, —$Y^{21}$—O—C(=O)—$Y^{22}$— or —$Y^{21}$—S(=O)$_2$—O—$Y^{22}$— (in the formulae, $Y^{21}$ and $Y^{22}$ each independently represents a divalent hydrocarbon group which may have a substituent, O represents a hydrogen atom, and m" represents an integer of 0 to 3).

In the case where the divalent linking group containing a hetero atom is —C(=O)—NH—, —C(=O)—NH—C(=O)—, —NH— or —NH—C(=NH)—, H may be substituted with a substituent such as an alkyl group, an acyl group or the like. The substituent (an alkyl group, an acyl group or the like) preferably has 1 to 10 carbon atoms, more preferably 1 to 8, and most preferably 1 to 5.

In general formulae —$Y^{21}$—O—$Y^{22}$—, —$Y^{21}$—O—, —$Y^{21}$—C(=O)—O—, —C(=O)—O—$Y^{21}$—, —[$Y^{21}$—C(=O)—O]$_{m''}$—$Y^{22}$—, —$Y^{21}$—O—C(=O)—$Y^{22}$— or —$Y^{21}$—S(=O)$_2$—O—$Y^{22}$—, $Y^{21}$ and $Y^{22}$ each independently represents a divalent hydrocarbon group which may have a substituent. Examples of the divalent hydrocarbon group include the same groups as those described above as the "divalent hydrocarbon group which may have a substituent" in the explanation of the aforementioned divalent linking group.

As $Y^{21}$, a linear aliphatic hydrocarbon group is preferable, more preferably a linear alkylene group, still more preferably a linear alkylene group of 1 to 5 carbon atoms, and a methylene group or an ethylene group is particularly desirable.

As $Y^{22}$, a linear or branched aliphatic hydrocarbon group is preferable, and a methylene group, an ethylene group or an alkylmethylene group is more preferable. The alkyl group within the alkylmethylene group is preferably a linear alkyl group of 1 to 5 carbon atoms, more preferably a linear alkyl group of 1 to 3 carbon atoms, and most preferably a methyl group.

In the group represented by the formula —[$Y^{21}$—C(=O)—O]$_{m''}$—$Y^{22}$—, m" represents an integer of 0 to 3, preferably an integer of 0 to 2, more preferably 0 or 1, and most preferably 1. Namely, it is particularly desirable that the group represented by the formula —[$Y^{21}$—C(=O)—O]$_{m''}$—$Y^{22}$— is a group represented by the formula —$Y^{21}$—C(=O)—O—$Y^{22}$—. Among these, a group represented by the formula —(CH$_2$)$_{a'}$—C(=O)—O—(CH$_2$)$_{b'}$— is preferable. In the formula, a' is an integer of 1 to 10, preferably an integer of 1 to 8, more preferably an integer of 1 to 5, still more preferably 1 or 2, and most preferably 1. b' is an integer of 1 to 10, preferably an integer of 1 to 8, more preferably an integer of 1 to 5, still more preferably 1 or 2, and most preferably 1.

Among these examples, as $Ya^{x0}$, an ester bond [—C(=O)—O—, —O—C(=O)—], an ether bond (—O—), a linear or branched alkylene group, an aromatic hydrocarbon group, or a combination thereof, or a single bond is preferable. Among these examples, as $Ya^{x0}$, a single bond or a combination of an ester bond [—C(=O)—O—, —O—C(=O)—] and a linear alkylene group is more preferable.

In formula (a0-1), $C^T$ represents a tertiary carbon atom, and the α-position of $C^t$ is a carbon atom which constitutes a carbon-carbon unsaturated bond.

The "α-position of $C^t$" refers to the first carbon atom adjacent to the carbon atom ($C^t$) bonded to the oxy group (—O—) in formula (a0-1).

In formula (a0-1), "—$C^t$($R^{11}$)($R^{12}$)($R^{13}$)" is an acid dissociable group. The acid dissociable group protects the oxy group (—O—) side of the carbonyloxy group [—C(=O)—O—] in formula (a0-1). An "acid dissociable group" exhibits acid dissociability such that the bond between the acid dissociable group and the adjacent oxygen atom (O) is cleaved by the action of acid. When the acid dissociable group is dissociated by the action of acid, a polar group which exhibits a higher polarity than the acid dissociable group is generated, and the polarity is increased. As a result, the polarity of the entire component (A1) is increased. By the increase in the polarity, the solubility in an alkali developing solution changes, and the solubility in an alkali developing solution is relatively increased, whereas the solubility in an organic developing solution is relatively decreased.

In formula (a0-1), at least one of $R^{11}$, $R^{12}$ and $R^{13}$ has a carbon atom constituting a carbon-carbon unsaturated bond at the α-position of $C^t$.

In formula (a0-1), $R^{11}$ represents an aromatic hydrocarbon group which may have a substituent, or a chain hydrocarbon group.

Examples of the aromatic hydrocarbon group for $R^{11}$ include a group in which 1 or more hydrogen atoms have been removed from an aromatic hydrocarbon ring having 5 to 30 carbon atoms. Among these examples, as $R^{11}$, a group in which 1 hydrogen atom has been removed from an aromatic hydrocarbon group of 6 to 15 carbon atoms is preferable, a group in which 1 hydrogen atom has been removed from benzene, naphthalene, anthracene or phenanthrene is more preferable, a group in which 1 hydrogen atom has been removed from benzene, naphthalene or anthracene is still more preferable, and a group in which 1 hydrogen atom has been removed from benzene is most preferable.

Examples of the substituent for $R^{11}$ include a methyl group, an ethyl group, a propyl group, a hydroxyl group, a carboxyl group, a halogen atom (a fluorine atom, a chlorine atom, a bromine atom, or the like), an alkoxy group (a methoxy group, an ethoxy group, a propoxy group, a butoxy group, or the like), and an alkyloxycarbonyl group.

The chain hydrocarbon group for $R^{11}$ may be a saturated hydrocarbon group or an unsaturated hydrocarbon group, and may be linear or branched.

The linear saturated hydrocarbon group (alkyl group) for $R^{11}$ preferably has 1 to 10 carbon atoms, more preferably 1 to 5 carbon atoms, still more preferably 1 to 4 carbon atoms, and most preferably 1 or 2 carbon atoms. Specific examples include a methyl group, an ethyl group, an n-propyl group, an n-butyl group and an n-pentyl group. Among these, a methyl group, an ethyl group or an n-butyl group is preferable, and a methyl group or an ethyl group is more preferable.

The branched alkyl group for $R^{11}$ preferably has 3 to 10 carbon atoms, and more preferably 3 to 5 carbon atoms. Specific examples include an isopropyl group, an isobutyl group, a tert-butyl group, an isopentyl group, a neopentyl group a 1,1-diethylpropyl group and a 2,2-dimethylbutyl group. Among these, an isopropyl group is preferable.

Examples of the unsaturated hydrocarbon group for $R^{11}$ include an alkenyl group.

The alkenyl group for $R^{11}$ preferably has 2 to 10 carbon atoms, more preferably 2 to 5 carbon atoms, still more preferably 2 to 4 carbon atoms, and most preferably 3 carbon atoms. Examples of linear alkenyl groups include a vinyl group, a propenyl group (an allyl group) and a butynyl group. Examples of branched alkenyl groups include a 1-methylvinyl group, a 2-methylvinyl group, a 1-methylpropenyl group and a 2-methylpropenyl group. Among these examples, as the chain-like alkenyl group, a linear alkenyl group is preferable, a vinyl group or a propenyl group is more preferable, and a vinyl group is most preferable.

In formula (a0-1), $R^{12}$ and $R^{13}$ each independently represents a chain hydrocarbon group which may have a substituent, or $R^{12}$ and $R^{13}$ are mutually bonded to form a cyclic group which may have a substituent.

The chain hydrocarbon group for $R^{12}$ and $R^{13}$ is the same as defined for the chain hydrocarbon group for $R^{11}$. Further, the substituent for the chain hydrocarbon group represented by $R^{12}$ or $R^{13}$ is the same as defined for the substituent for the chain hydrocarbon group represented by $R^{11}$.

In the case where $R^{12}$ and $R^{13}$ are mutually bonded to form a cyclic group (cyclic hydrocarbon group), the cyclic group may be a polycyclic group or a monocyclic group. Further, the cyclic group may be an alicyclic hydrocarbon group or a condensed polycyclic hydrocarbon group in which an alicyclic hydrocarbon group is fused with an aromatic ring.

The cyclic aliphatic hydrocarbon group may have part of the carbon atoms constituting the ring structure thereof substituted with a substituent containing a hetero atom. As the substituent containing a hetero atom, —O—, —C(=O)—O—, —S—, —S(=O)$_2$— or —S(=O)$_2$—O— is preferable.

As the monocyclic aliphatic hydrocarbon group, a group in which 1 hydrogen atom has been removed from a monocycloalkane or a monocycloalkene is preferable. The monocycloalkane preferably has 3 to 6 carbon atoms, and specific examples thereof include cyclopentane and cyclohexane. The monocycloalkene preferably has 3 to 6 carbon atoms, and specific examples thereof include cyclopentene and cyclohexene.

As the polycyclic aliphatic hydrocarbon group, a group in which 1 hydrogen atom has been removed from a polycycloalkane or a polycycloalkene is preferable. The polycycloalkane preferably has 7 to 12 carbon atoms, and examples thereof include adamantane, norbornane, isobornane, tricyclodecane and tetracyclododecane. The polycycloalkene preferably has 7 to 12 carbon atoms, and examples thereof include adamantene, norbornene, isobornene, tricyclodecene and tetracyclododecene.

Examples of the condensed polycyclic hydrocarbon group in which an aromatic ring is fused with an alicyclic hydrocarbon group include a group in which one hydrogen atom has been removed from an aliphatic ring of a bicyclic compound, such as tetrahydronaphthalene or indane.

The cyclic group which is formed by the $R^{12}$ group and the $R^{13}$ group being mutually bonded may have a substituent. Examples of the substituent for the cyclic hydrocarbon group formed by $Xa^0$ together with $Ya^0$ include —$R^{P1}$, —$R^{P2}$—O—$R^{P1}$, —$R^{P2}$—CO—$R^{P1}$, —$R^{P2}$—CO—O$R^{P1}$, —$R^{P2}$—O—CO—$R^{P1}$, —$R^{P2}$—OH, —$R^{P2}$—CN and —$R^{P2}$—COOH ((hereafter, these substituents are sometimes collectively referred to as "$Ra^{06}$").

Here, $R^{P1}$ is a monovalent chain saturated hydrocarbon group having 1 to 10 carbon atoms, a monovalent aliphatic cyclic saturated hydrocarbon group having 3 to 20 carbon atoms, or a monovalent aromatic hydrocarbon group having 6 to 30 carbon atoms. Further, $R^{P2}$ is a single bond, a divalent chain saturated hydrocarbon group having 1 to 10 carbon atoms, a divalent aliphatic cyclic saturated hydrocarbon group having 3 to 20 carbon atoms, or a divalent aromatic hydrocarbon group having 6 to 30 carbon atoms. However, the saturated chain hydrocarbon group, the saturated cyclic aliphatic hydrocarbon group and the aromatic hydrocarbon group for $R^{P1}$ and $R^{P2}$ may have part or all of the hydrogen atoms substituted with fluorine. The aliphatic cyclic hydrocarbon group may have 1 or more substituents of 1 kind, or 1 or more substituents of a plurality of kinds.

Examples of the monovalent chain saturated hydrocarbon group having 1 to 10 carbon atoms include a methyl group, an ethyl group, a propyl group, a butyl group, a pentyl group, a hexyl group, a heptyl group, an octyl group, and a decyl group.

Examples of the monovalent aliphatic cyclic saturated hydrocarbon group having 3 to 20 carbon atoms include a monocyclic aliphatic saturated hydrocarbon group such as a cyclopropyl group, a cyclobutyl group, a cyclopentyl group, a cyclohexyl group, a cycloheptyl group, a cyclooctyl group, a cyclodecyl group, and a cyclododecyl group; and a polycyclic aliphatic saturated hydrocarbon group such as a bicyclo[2.2.2]octanyl group, a tricyclo[5.2.1.0²,⁶]decanyl group, a tricyclo[3.3.1.1³,⁷]decanyl group, a tetracyclo[6.2.1.1³,⁶.0²,⁷]dodecanyl group, and an adamantyl group.

Examples of the monovalent aromatic hydrocarbon group having 6 to 30 carbon atoms include a group obtained by removing one hydrogen atom from the aromatic hydrocarbon ring such as benzene, biphenyl, fluorene, naphthalene, anthracene, and phenanthrene.

Among these examples, as the cyclic group formed by $R^{12}$ and $R^{13}$ mutually bonded, an alicyclic hydrocarbon group which may have a substituent is preferable, a monocyclic aliphatic hydrocarbon group which may have a substituent is more preferable, a group in which one hydrogen atom has been removed from a monocycloalkane or a monocycloalkene is still more preferable, and in terms of reactivity, a group in which one hydrogen atom has been removed from cyclopentane or cyclopentene is most preferable.

Among the above examples, as the structural unit (a0), a structural unit derived from a compound represented by general formula (a0-11) shown below is preferable.

[Chemical Formula 3]

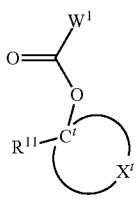

(a0-11)

In formula (a0-11), $W^1$ represents a polymerizable group-containing group; $C^t$ represents a tertiary carbon atom, and an α-position of $C^t$ is a carbon atom constituting a carbon-carbon unsaturated bond; $R^{11}$ represents an aromatic hydrocarbon group which may have a substituent, or a chain hydrocarbon group; $X^t$ represents a group which forms a cyclic hydrocarbon group together with $C^t$; provided that part or all of the hydrogen atoms of the cyclic hydrocarbon group may be substituted with a substituent.

In formula (a0-11), $W^1$ and $C^t$ are the same as defined for $W^1$ and $C^t$ in the aforementioned formula (a0-1).

In formula (a0-11), the cyclic hydrocarbon group formed by $X^t$ and $C^t$ is the same as defined for the cyclic group (cyclic hydrocarbon group) formed by $R^{12}$ and $R^{13}$ mutually bonded in the aforementioned formula (a0-1).

Among the above examples, as the structural unit (a0), a structural unit represented by general formula (a0-11-1) shown below is more preferable.

[Chemical Formula 4]

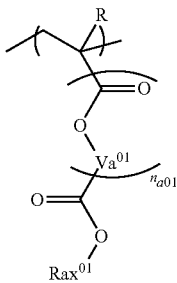

(a0-11-1)

In the formula, R represents a hydrogen atom, an alkyl group of 1 to 5 carbon atoms or a halogenated alkyl group of 1 to 5 carbon atoms; $Va^{01}$ represents a divalent hydrocarbon group optionally having an ether bond; $n_{a01}$ represents an integer of 0 to 2; $Rax^{01}$ is a group represented by general formula (a0-r-1) shown below, a general formula (a0-r-2) shown below or a group represented by general formula (a0-r-3) shown below.

[Chemical Formula 5]

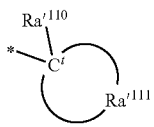

(a0-r-1)

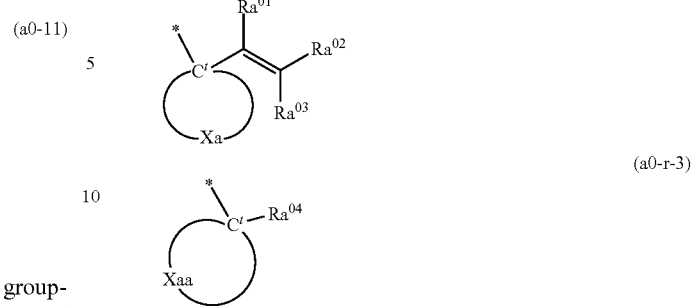

(a0-r-2)

(a0-r-3)

In formula (a0-r-1), $C^t$ represents a tertiary carbon atom; $Ra'^{110}$ represents a linear or branched alkyl group having 1 to 12 carbon atoms optionally having part thereof substituted with a halogen atom or a hetero atom-containing group; $Ra'^{111}$ is a group which forms a monocyclic alicyclic hydrocarbon group together with $C^t$; provided that part or all of the hydrogen atoms of the monocyclic alicyclic hydrocarbon group may be substituted; provided that, in the monocyclic alicyclic hydrocarbon group, the α-position of $C^t$ is a carbon atom constituting a carbon-carbon unsaturated bond.

In formula (a0-r-2), $C^t$ represents a tertiary carbon atom; Xa is a group which forms a monocyclic alicyclic hydrocarbon group together with $C^t$; provided that part or all of the hydrogen atoms of the monocyclic alicyclic hydrocarbon group may be substituted; $Ra^{01}$ to $Ra^{03}$ each independently represents a hydrogen atom, a monovalent saturated chain hydrocarbon group of 1 to 10 carbon atoms or a monovalent saturated aliphatic cyclic hydrocarbon group of 3 to 20 carbon atoms; provided that part or all of the hydrogen atoms of the saturated chain hydrocarbon or the saturated aliphatic cyclic hydrocarbon may be substituted with a substituent; 2 or more of $Ra^{01}$ to $Ra^{03}$ may be mutually bonded to form an aliphatic cyclic structure, but does not form a bridged structure.

In formula (a0-r-3), $C^t$ represents a tertiary carbon atoms; Xaa is a group which forms a monocyclic alicyclic hydrocarbon group together with $C^t$; provided that part or all of the hydrogen atoms of the monocyclic alicyclic hydrocarbon group may be substituted with a substituent; $Ra^{04}$ represents an aromatic hydrocarbon group which may have a substituent; and * represents a bonding site.

In formula (a0-11-1), as the alkyl group of 1 to 5 carbon atoms for R, a linear or branched alkyl group of 1 to 5 carbon atoms is preferable, and specific examples thereof include a methyl group, an ethyl group, a propyl group, an isopropyl group, an n-butyl group, an isobutyl group, a tert-butyl group, a pentyl group, an isopentyl group and a neopentyl group. The halogenated alkyl group of 1 to 5 carbon atoms represented by R is a group in which part or all of the hydrogen atoms of the aforementioned alkyl group of 1 to 5 carbon atoms have been substituted with halogen atoms. As the halogen atom, a fluorine atom is most preferable.

As R, a hydrogen atom, an alkyl group of 1 to 5 carbon atoms or a fluorinated alkyl group of 1 to 5 carbon atoms is preferable, and a hydrogen atom or a methyl group is particularly desirable in terms of industrial availability.

In formula (a0-11-1), the divalent linking group for $Va^{01}$ is the same as defined for the divalent linking group for $Ya^{xo}$ described above in relation to $W^1$ in the aforementioned formula (a0-1).

In formula (a0-11-1), $n_{a01}$ represents an integer of 0 to 2, and more preferably 0 or 1.

In formula (a0-r-1), $Ra'^{110}$ represents a linear or branched alkyl group having 1 to 12 carbon atoms optionally having part thereof substituted with a halogen atom or a hetero atom-containing group.

The linear alkyl group for $Ra'^{110}$ has 1 to 12 carbon atoms, preferably 1 to 10 carbon atoms, and more preferably 1 to 5 carbon atoms. Specific examples include a methyl group, an ethyl group, an n-propyl group, an n-butyl group and an n-pentyl group. Among these, a methyl group, an ethyl group or an n-butyl group is preferable, and a methyl group or an ethyl group is more preferable. The branched alkyl group for $Ra'^{110}$ preferably has 3 to 10 carbon atoms, and more preferably 3 to 6 carbon atoms. Specific examples include an isopropyl group, an isobutyl group, a tert-butyl group, an isopentyl group, a neopentyl group, a 1,1-diethylpropyl group, a 1,1-dimethylbutyl group, a 1,1-dimethylpentyl group and a 2,2-dimethylbutyl group. Among these examples, an isopropyl group or a tert-butyl group is preferable.

The alkyl group for $Ra'^{110}$ may have part thereof substituted with a halogen atom or a hetero atom-containing group. For example, part of the hydrogen atoms constituting the alkyl group may be substituted with a halogen atom or a hetero atom-containing group. Further, for example, part of the carbon atoms constituting the alkyl group (e.g., a methylene group) may be substituted with a hetero atom-containing group.

Examples of the hetero atom include an oxygen atom, a sulfur atom and a nitrogen atom. Examples of the hetero atom-containing group include an oxygen atom (—O—), —C(=O)—O—, —O—C(=O)—, —C(=O)—, —O—C(=O)—O—, —C(=O)—NH—, —NH—, —S—, —S(=O)$_2$— and —S(=O)$_2$—O—.

In formula (a0-r-1), $C^t$ represents a tertiary carbon atom.

In formula (a0-r-1), $Ra'^{111}$ is a group which forms a monocyclic alicyclic hydrocarbon group together with $C^t$. Part or all of the hydrogen atoms of the aliphatic cyclic group may be substituted with a substituent.

Examples of the monocyclic alicyclic hydrocarbon group formed by $Ra'^{111}$ and $C^t$ include a group in which 2 or more hydrogen atoms have been removed from a monocycloalkane. The monocycloalkane preferably has 3 to 10 carbon atoms, more preferably 3 to 8 carbon atoms, and still more preferably 3 to 6 carbon atoms. Specific examples of the monocycloalkane include cyclopentane and cyclohexane.

In formula (a0-r-2), $C^t$ represents a tertiary carbon atoms.

In formula (a0-r-2), Xa is a group which forms a monocyclic alicyclic hydrocarbon group together with $C^t$. Part or all of the hydrogen atoms of the aliphatic cyclic group may be substituted with a substituent.

The monocyclic alicyclic hydrocarbon group formed by Xa and $C^t$ is the same as defined for the monocyclic alicyclic hydrocarbon group for $Ra'^{111}$ (the monocyclic alicyclic hydrocarbon group formed together with $C^t$) in the aforementioned formula (a0-r-1).

As the substituent for the aliphatic cyclic group formed by Xa and $C^t$, for example, the same groups as those defined for the aforementioned $Ra^{06}$ may be mentioned.

In formula (a0-r-2), $Ra^{01}$ to $Ra^{03}$ each independently represents a hydrogen atom, a monovalent saturated chain hydrocarbon group of 1 to 10 carbon atoms or a monovalent saturated aliphatic cyclic hydrocarbon group of 3 to 20 carbon atoms, provided that part or all of the hydrogen atoms of the saturated chain hydrocarbon or the saturated aliphatic cyclic hydrocarbon may be substituted with a substituent; 2 or more of $Ra^{01}$ to $Ra^{03}$ may be mutually bonded to form an aliphatic cyclic structure, but does not form a bridged structure.

In formula (a0-r-2), examples of the monovalent saturated chain hydrocarbon group of 1 to 10 carbon atoms for $Ra^{01}$ to $Ra^{03}$ include a methyl group, an ethyl group, a propyl group, a butyl group, a pentyl group, a hexyl group, a heptyl group, an octyl group, and a decyl group.

Examples of the monovalent aliphatic cyclic saturated hydrocarbon group having 3 to 20 carbon atoms for $Ra^{01}$ to $Ra^{03}$ include a cyclopropyl group, a cyclobutyl group, a cyclopentyl group, a cyclohexyl group, a cycloheptyl group, a cyclooctyl group, a cyclodecyl group, and a cyclododecyl group.

Among these examples, in terms of ease in synthesis, $Ra^{01}$ to $Ra^{03}$ is preferably a hydrogen atom or a monovalent saturated hydrocarbon group having 1 to 10 carbon atoms, more preferably a hydrogen atom, a methyl group or an ethyl group, and most preferably a hydrogen atom.

As the substituent for the saturated chain hydrocarbon group or saturated cyclic aliphatic hydrocarbon group represented by $Ra^{01}$ to $Ra^{03}$, for example, the same substituents as those described above for $Ra^{06}$ may be mentioned.

Examples of the group containing a carbon-carbon double bond which is generated by forming a cyclic structure in which two or more of $Ra^{01}$ to $Ra^{03}$ are bonded to each other include a cyclopentenyl group, a cyclohexenyl group, a methyl cyclopentenyl group, a methyl cyclohexenyl group, a cyclopentylideneethenyl group, and a cyclohexylideneethenyl group.

In formula (a0-r-3), $C^t$ represents a tertiary carbon atoms.

In formula (a0-r-3), Xaa is a group which forms a monocyclic alicyclic hydrocarbon group together with $C^t$. provided that part or all of the hydrogen atoms of the monocyclic alicyclic hydrocarbon group may be substituted; The monocyclic alicyclic hydrocarbon group formed by Xaa and $C^t$ is the same as defined for $Ra'^{111}$ (the monocyclic alicyclic hydrocarbon group formed together with $C^t$) in the aforementioned formula (a0-r-1).

Examples of the substituent for the monocyclic alicyclic hydrocarbon group formed by Xaa and $C^t$ include the aforementioned groups $Ra^{06}$.

In formula (a0-r-3), $Ra^{04}$ represents an aromatic hydrocarbon group which may have a substituent. As the aromatic hydrocarbon group for $Ra^{04}$, a group in which one or more hydrogen atoms have been removed from an aromatic hydrocarbon ring having 6 to 15 carbon atoms is preferable, and a group in which one or more hydrogen atoms have been removed from benzene is more preferable.

As the substituent for $Ra^{04}$, the same substituents as those described above for the aromatic hydrocarbon group represented by $R^{11}$ may be mentioned.

In general formula (a0-11-1), among the above examples, $Rax^{01}$ is preferably a group represented by general formula (a0-r-2) or (a0-r-3). In general formula (a0-11-1), in the case where $Rax^{01}$ is a group represented by general formula (a0-r-2) or (a0-r-3), the reactivity of the structural unit (a0) in the deprotection is enhanced. As a result, in the formation of a resist pattern, sensitivity, reduction of roughness, and rectangularity of pattern may be further improved.

Specific examples of the group represented by the aforementioned formula (a0-r-1) are shown below. * indicates the bonding site with the oxy group (—O—).

[Chemical Formula 6]
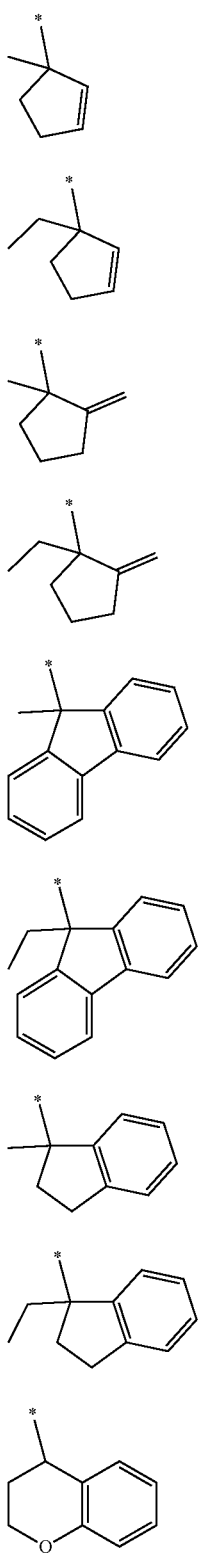
(a0-r-1-1)
(a0-r-1-2)
(a0-r-1-3)
(a0-r-1-4)
(a0-r-1-5)
(a0-r-1-6)
(a0-r-1-7)
(a0-r-1-8)
(a0-r-1-9)
Specific examples of the group represented by the aforementioned formula (a0-r-2) are shown below. * indicates the bonding site with the oxy group (—O—).
[Chemical Formula 7]
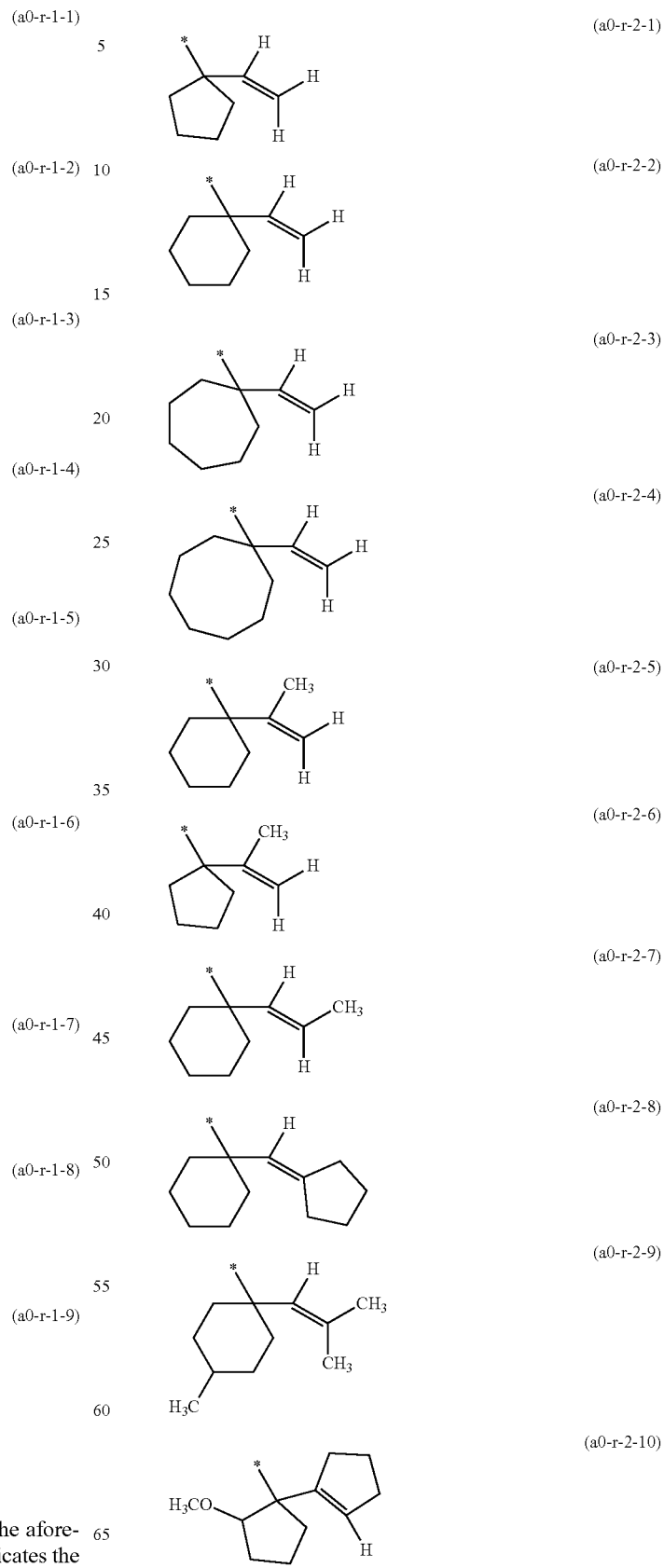
(a0-r-2-1)
(a0-r-2-2)
(a0-r-2-3)
(a0-r-2-4)
(a0-r-2-5)
(a0-r-2-6)
(a0-r-2-7)
(a0-r-2-8)
(a0-r-2-9)
(a0-r-2-10)

-continued
(a0-r-2-11)
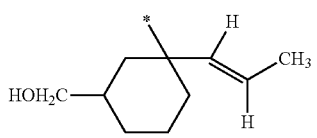
(a0-r-2-12)
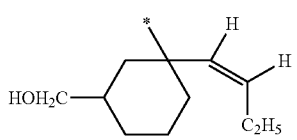
[Chemical Formula 8]
(a0-r-2-13)
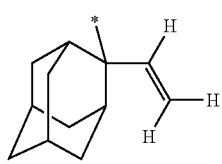
(a0-r-2-14)
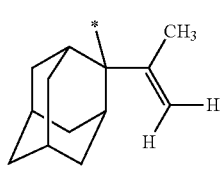
(a0-r-2-14)
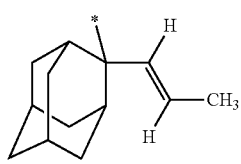
(a0-r-2-15)
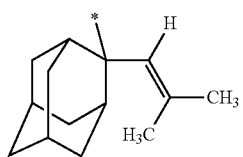
(a0-r-2-16)
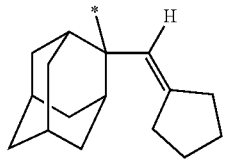
(a0-r-2-17)
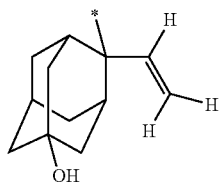
(a0-r-2-18)
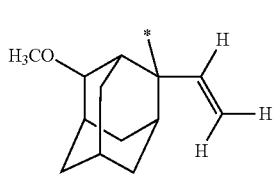
-continued
(a0-r-2-19)
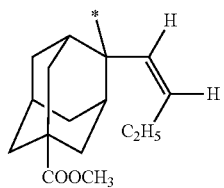
(a0-r-2-20)
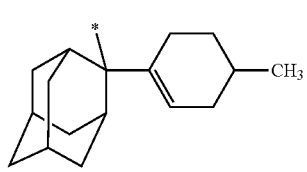
[Chemical Formula 9]
(a0-r-2-21)
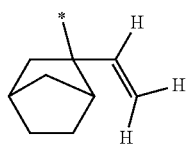
(a0-r-2-22)
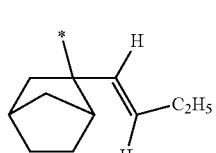
(a0-r-2-23)
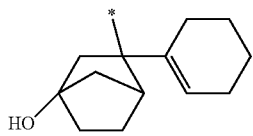
(a0-r-2-24)
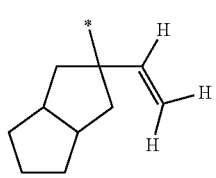
(a0-r-2-25)
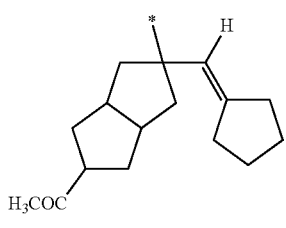
(a0-r-2-26)
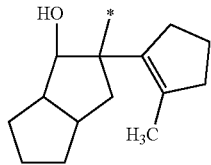
(a0-r-2-27)
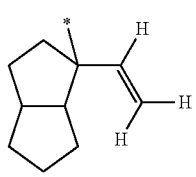

-continued
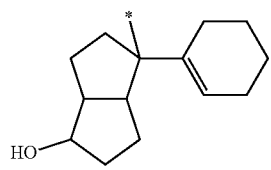 (a0-r-2-28)
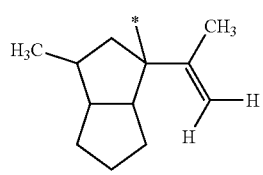 (a0-r-2-29)
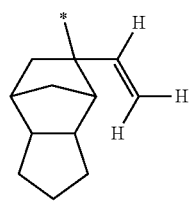 (a0-r-2-30)
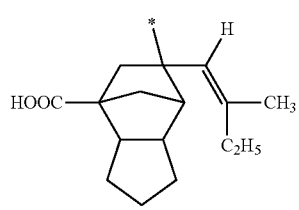 (a0-r-2-31)
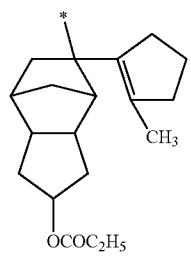 (a0-r-2-32)
[Chemical Formula 10]
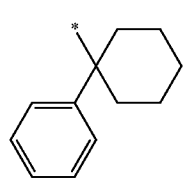 (a0-r-3-1)
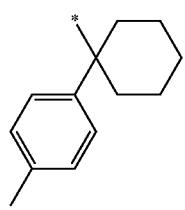 (a0-r-3-2)
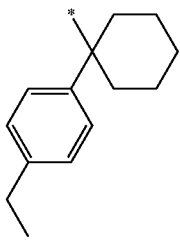 (a0-r-3-3)
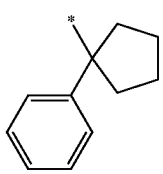 (a0-r-3-4)
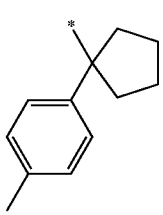 (a0-r-3-5)
(a0-r-3-6)
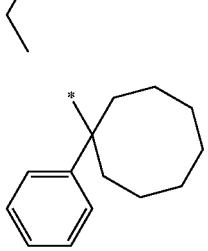 (a0-r-3-7)
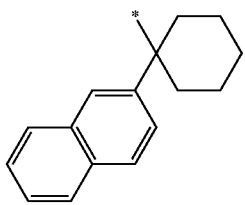 (a0-r-3-8)
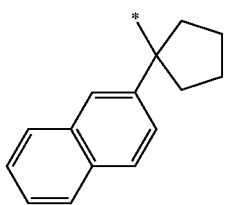 (a0-r-3-9)

-continued
(a0-r-3-10)
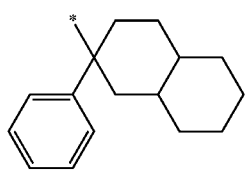
(a0-r-3-11)
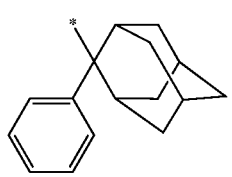
Specific examples of the structural unit (a0) are shown below. In the formulae shown below, $R^\alpha$ represents a hydrogen atom, a methyl group or a trifluoromethyl group.
[Chemical Formula 11]
(a0-1a-1)
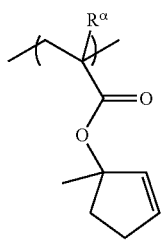
(a0-1a-2)
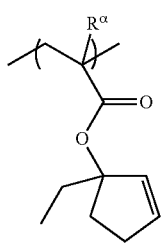
(a0-1a-3)
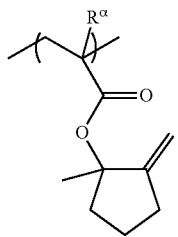
(a0-1a-4)
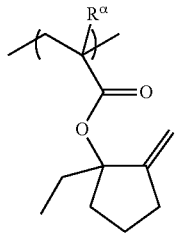
(a0-1a-5)
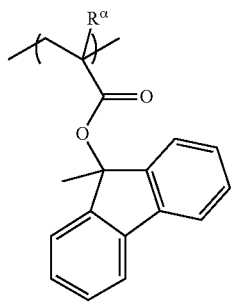
(a0-1a-6)
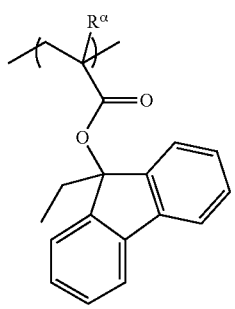
(a0-1a-7)
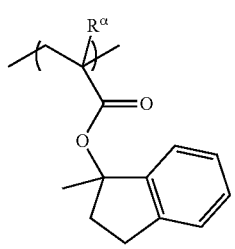
(a0-1a-8)
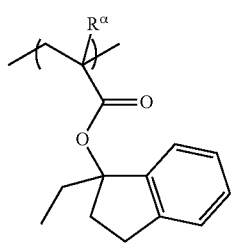
(a0-1a-9)
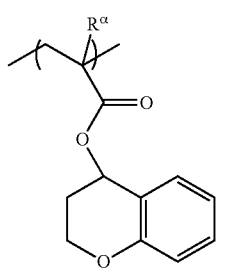

[Chemical Formula 12]
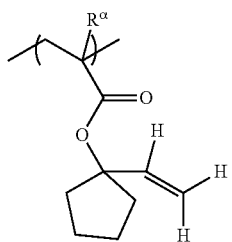 (a0-1a-10)
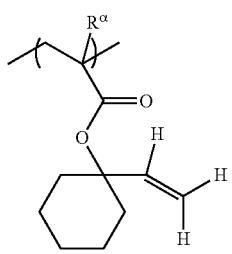 (a0-1a-11)
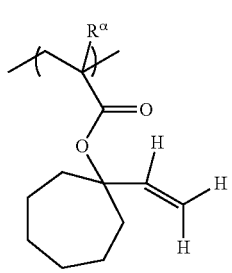 (a0-1a-12)
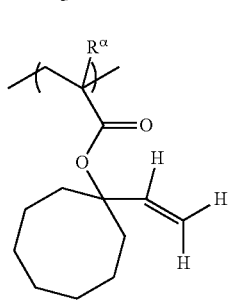 (a0-1a-13)
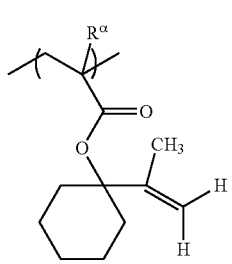 (a0-1a-14)
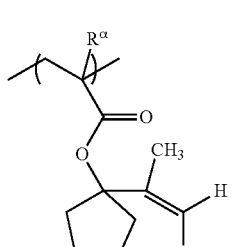 (a0-1a-15)
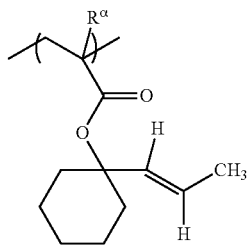 (a0-1a-16)
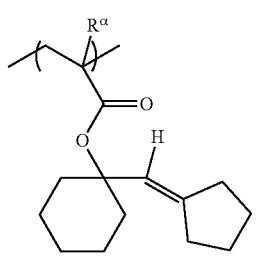 (a0-1a-17)
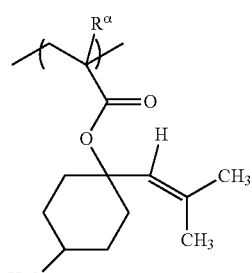 (a0-1a-18)
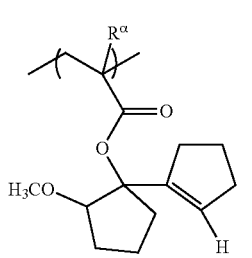 (a0-1a-19)
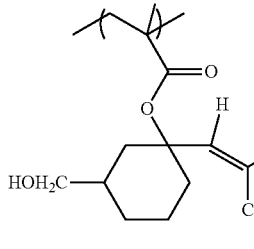 (a0-1a-20)
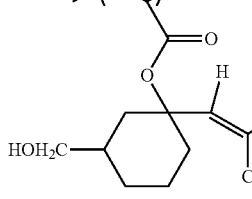 (a0-1a-21)

(a0-1a-22)
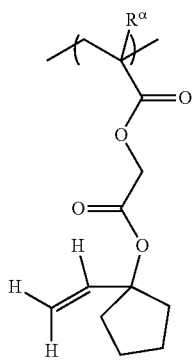
[Chemical Formula 13]
(a0-1a-23)
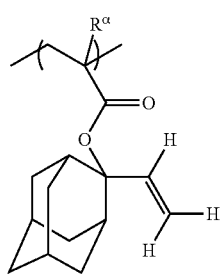
(a0-1a-24)
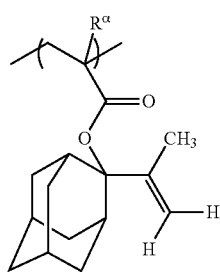
(a0-1a-25)
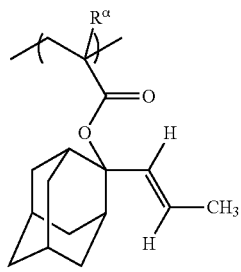
(a0-1a-26)
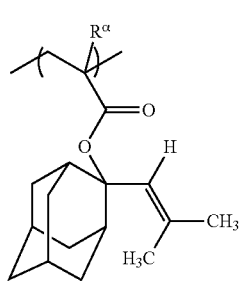
(a0-1a-27)
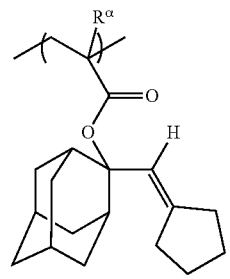
(a0-1a-28)
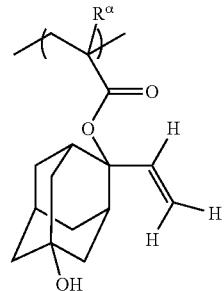
(a0-1a-29)
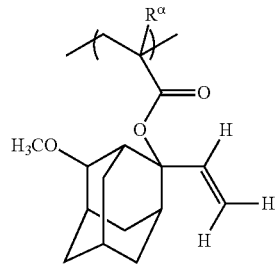
(a0-1a-30)
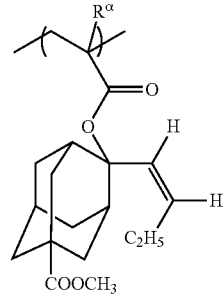
(a0-1a-31)
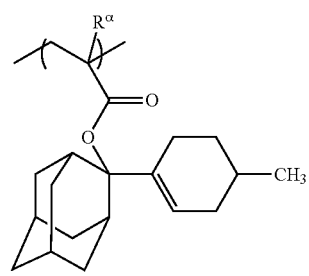

[Chemical Formula 14]
(a0-1a-32) 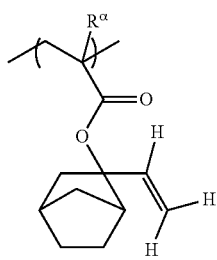
(a0-1a-33) 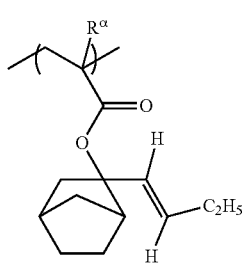
(a0-1a-34) 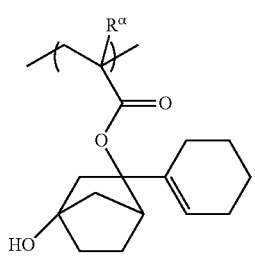
(a0-1a-35) 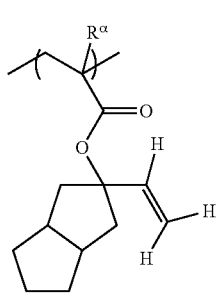
(a0-1a-36) 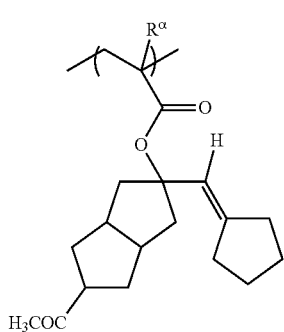
(a0-1a-37) 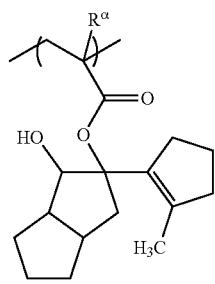
(a0-1a-38) 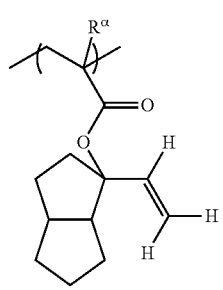
(a0-1a-39) 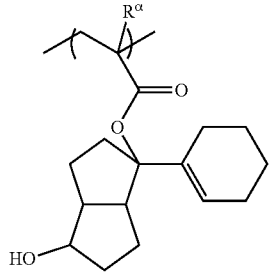
(a0-1a-40) 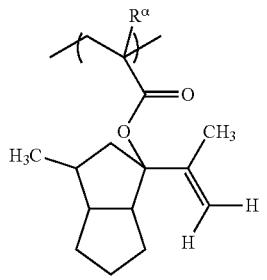
(a0-1a-41) 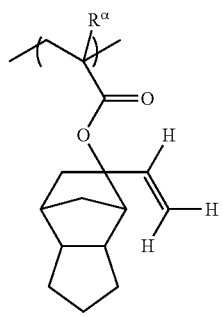

(a0-1a-42)
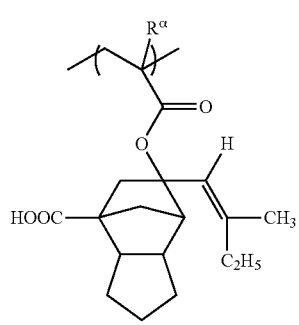
(a0-1a-43)
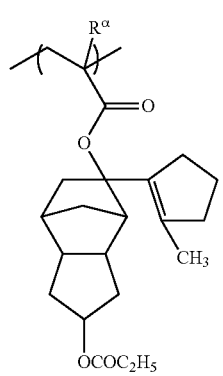
[Chemical Formula 15]
(a0-1a-44)
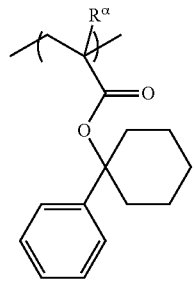
(a0-1a-45)
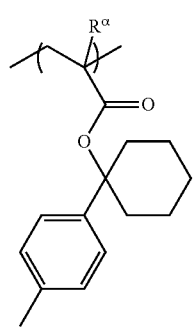
(a0-1a-46)
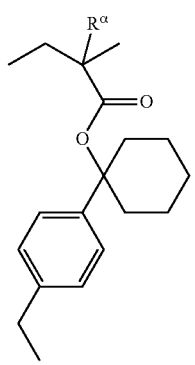
(a0-1a-47)
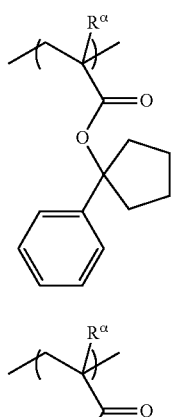
(a0-1a-48)
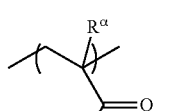
(a0-1a-49)
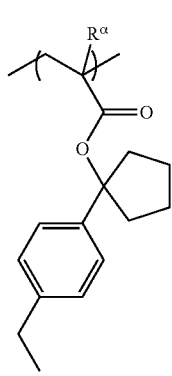
(a0-1a-50)
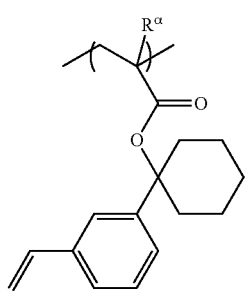

(a0-1a-51)
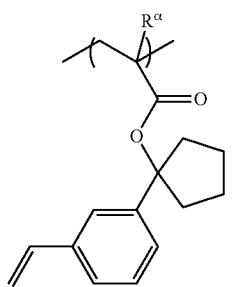
(a0-1a-52)
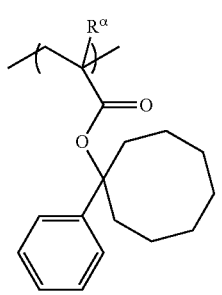
(a0-1a-53)
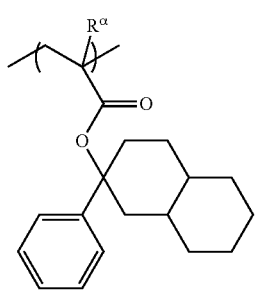
(a0-1a-54)
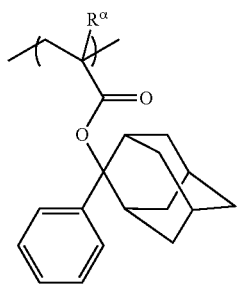
(a0-1a-55)
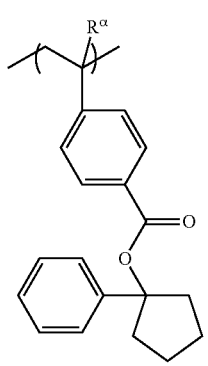
(a0-1a-56)
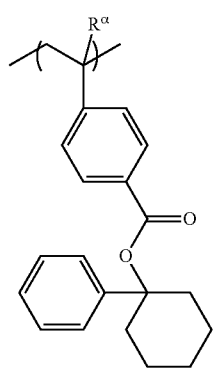
[Chemical Formula 16]
(a0-1a-57)
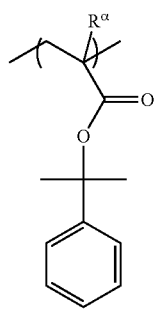
(a0-1a-58)
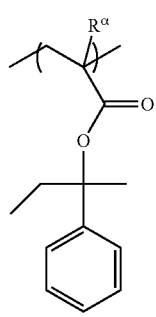
(a0-1a-59)
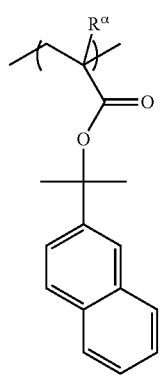

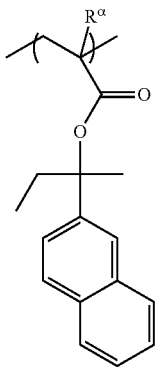

(a0-1a-60)

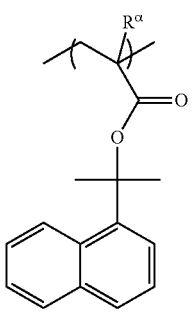

(a0-1a-61)

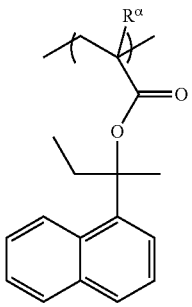

(a0-1a-62)

Among the above examples, as the structural unit (a0), at least one member selected from the group consisting of structural units represented by chemical formulae (a0-1a-1), (a0-1a-3), (a0-1a-5), (a0-1a-8), (a0-1a-10), (a0-1a-11), (a0-1a-22), (a0-1a-44) and (a0-1a-47) is preferable, at least one member selected from the group consisting of structural units represented by chemical formulae (a0-1a-10), (a0-1a-11), (a0-1a-22), (a0-1a-44) and (a0-1a-47) is more preferable, and at least one member selected from the group consisting of structural units represented by chemical formulae (a0-1a-10), (a0-1a-11), (a0-1a-44) and (a0-1a-47) is still more preferable.

As the structural unit (a0) contained in the component (A1), 1 kind of structural unit may be used, or 2 or more kinds of structural units may be used.

In the component (A1), the amount of the structural unit (a0) based on the combined total (100 mol %) of all structural units constituting the component (A1) is preferably 20 to 80 mol %, more preferably 25 to 70 mol %, and still more preferably 40 to 70 mol %.

When the amount of the structural unit (a0) is within the above-mentioned preferable range, efficiency of the deprotection reaction and solubility in a developing solution may be reliably assured, and the effects of the present invention may be more reliably achieved.

<<Other Structural Units>>

If desired, the component (A1) may include, in addition to the structural unit (a), other structural unit.

Examples of other structural units include a structural unit (a10) represented by general formula (a10-1) described later; a structural unit (a1) containing an acid decomposable group and which exhibits increased polarity by the action of acid (provided that structural units that fall under the definition of the structural unit (a0) are excluded); a structural unit (a2) containing a lactone-containing cyclic group, an —SO$_2$— containing cyclic group or a carbonate-containing cyclic group (provided that structural units that fall under the definition of the structural units (a0) and (a1) are excluded); a structural unit (a3) containing a polar group-containing aliphatic hydrocarbon group (provided that structural units that fall under the definition of the structural units (a0) and (a1) are excluded); a structural unit (a4) containing an acid non-dissociable aliphatic cyclic group; and a structural unit (st) derived from styrene or a derivative thereof.

Structural Unit (a10):

The structural unit (a10) is a structural unit represented by general formula (a10-1) shown below.

[Chemical Formula 17]

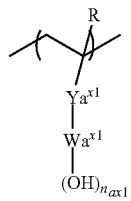

(a10-1)

In the formula, R represents a hydrogen atom, an alkyl group of 1 to 5 carbon atoms or a halogenated alkyl group of 1 to 5 carbon atoms; $Ya^{x1}$ represents a single bond or a divalent linking group; $Wa^{x1}$ represents an aromatic hydrocarbon group which may have a substituent; and $n_{ax1}$ represents an integer of 1 or more.

In general formula (a10-1), R represents a hydrogen atom, an alkyl group of 1 to 5 carbon atoms or a halogenated alkyl group of 1 to 5 carbon atoms.

As the alkyl group having 1 to 5 carbon atoms for R, a linear or branched alkyl group of 1 to 5 carbon atoms is preferable, and specific examples thereof include a methyl group, an ethyl group, a propyl group, an isopropyl group, an n-butyl group, an isobutyl group, a tert-butyl group, a pentyl group, an isopentyl group and a neopentyl group.

The halogenated alkyl group of 1 to 5 carbon atoms represented by R is a group in which part or all of the hydrogen atoms of the aforementioned alkyl group of 1 to 5 carbon atoms have been substituted with halogen atoms. As the halogen atom, a fluorine atom is most preferable.

As R, a hydrogen atom, an alkyl group of 1 to 5 carbon atoms or a fluorinated alkyl group of 1 to 5 carbon atoms is preferable, and in view of industrial availability, a hydrogen atom, a methyl group or a trifluoromethyl group is more preferable, a hydrogen atom or a methyl group is still more preferable, and a methyl group is most preferable.

In formula (a10-1), $Ya^{x1}$ represents a single bond or a divalent linking group.

In the chemical formula, the divalent linking group for $Ya^{x1}$ is the same as the divalent linking group for $Ya^{x0}$ in the aforementioned formula (a0-1).

Among the above examples, as $Ya^{x1}$, a single bond, an ester bond [—C(=O)—O—, —O—C(=O)—], an ether bond (—O—), a linear or branched alkylene group, or a combination of these is preferable, and a single bond or an ester bond [—C(=O)—O—, —O—C(=O)—] is more preferable.

In formula (a10-1), $Wa^{x1}$ represents an aromatic hydrocarbon group which may have a substituent.

Examples of the aromatic hydrocarbon group for $Wa^{x1}$ include a group obtained by removing $(n_{ax1}+1)$ hydrogen atoms from an aromatic ring which may have a substituent. The aromatic ring is not particularly limited, as long as it is a cyclic conjugated compound having $(4n+2)\pi$ electrons, and may be either monocyclic or polycyclic. The aromatic ring preferably has 5 to 30 carbon atoms, more preferably 5 to 20 carbon atoms, and still more preferably 6 to 15 carbon atoms, and most preferably 6 to 12 carbon atoms. Specific examples of the aromatic ring include an aromatic hydrocarbon ring, such as benzene, naphthalene, anthracene or phenanthrene; and an aromatic heterocyclic ring in which part of the carbon atoms constituting the aromatic hydrocarbon ring has been substituted with a hetero atom. Examples of the hetero atom within the aromatic hetero rings include an oxygen atom, a sulfur atom and a nitrogen atom. Specific examples of the aromatic hetero ring include a pyridine ring and a thiophene ring.

Examples of the aromatic hydrocarbon group for $Wa^{x1}$ include a group obtained by removing $(n_{ax1}+1)$ hydrogen atoms from an aromatic compound having two or more aromatic rings which may have a substituent (e.g., biphenyl or fluorene).

Among the above examples, as $Wa^{x1}$, a group in which $(n_{ax1}+1)$ hydrogen atoms have been removed from benzene, naphthalene, anthracene or biphenyl is preferable, a group in which $(n_{ax1}+1)$ hydrogen atoms have been removed from benzene or naphthalene is more preferable, and a group in which $(n_{ax1}+1)$ hydrogen atoms have been removed from benzene is still more preferable.

The aromatic hydrocarbon group for Wax may or may not have a substituent. Examples of the substituent include an alkyl group, an alkoxy group, a halogen atom, and a halogenated alkyl group. The alkyl group, the alkoxy group and the halogen atom and the halogenated alkyl group as the substituent are the same as defined for the substituent for the cyclic aliphatic hydrocarbon group represented by $Ya^{x1}$. The substituent is preferably a linear or branched alkyl group having 1 to 5 carbon atoms, more preferably a linear or branched alkyl group having 1 to 3 carbon atoms, still more preferably an ethyl group or a methyl group, and most preferably a methyl group. The aromatic hydrocarbon group for $Wa^{x1}$ preferably has no substituent.

In formula (a10-1), $n_{ax1}$ is an integer of 1 or more, preferably an integer of 1 to 10, more preferably an integer of 1 to 5, still more preferably 1, 2 or 3, and most preferably 1 or 2.

Specific examples of the structural unit (a10) represented by formula (a10-1) are shown below.

In the formulae shown below, $R^\alpha$ represents a hydrogen atom, a methyl group or a trifluoromethyl group.

[Chemical Formula 18]

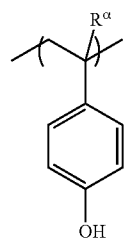

(a10-1-11)

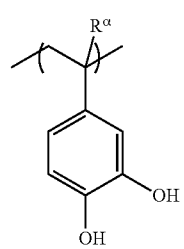

(a10-1-12)

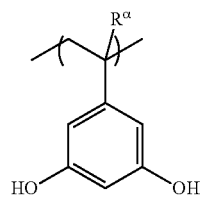

(a10-1-13)

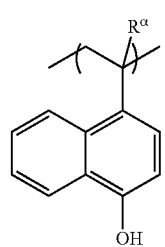

(a10-1-14)

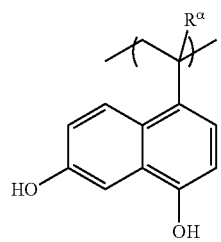

(a10-1-15)

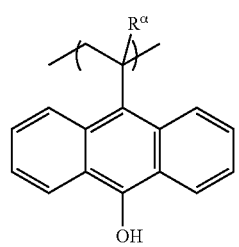

(a10-1-16)

-continued
(a10-1-17)
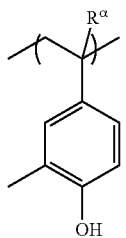
(a10-1-18)
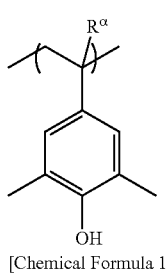
[Chemical Formula 19]
(a10-1-21)
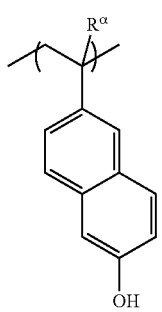
(a10-1-22)
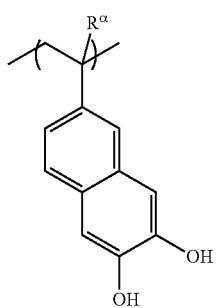
(a10-1-23)
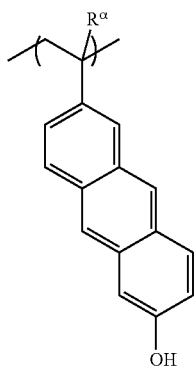
-continued
(a10-1-24)
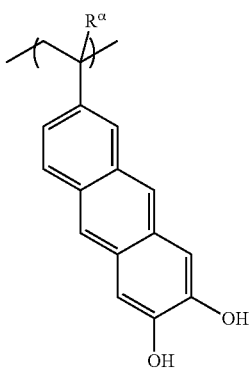
[Chemical Formula 20]
(a10-1-31)
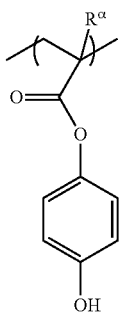
(a10-1-32)
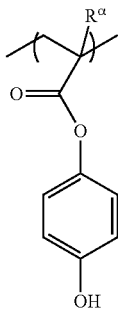
(a10-1-33)
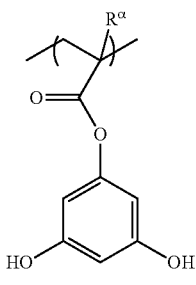
(a10-1-34)
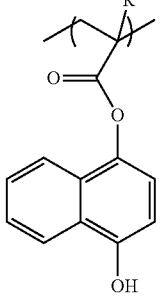

(a10-1-35)
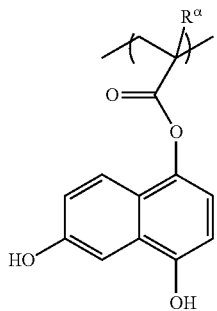

(a10-1-36)
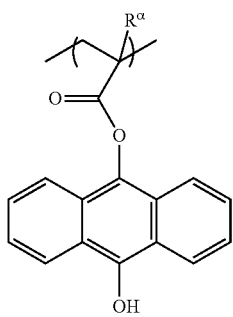

[Chemical Formula 21]

(a10-1-41)
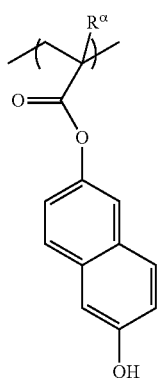

(a10-1-42)
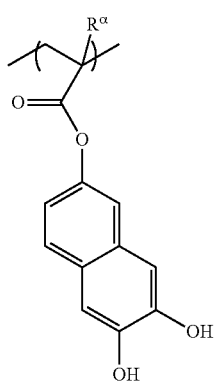

(a10-1-43)
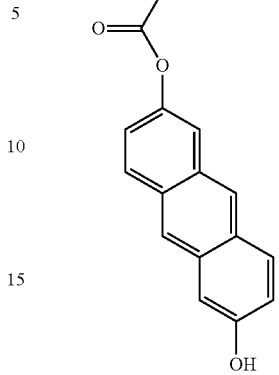

(a10-1-44)
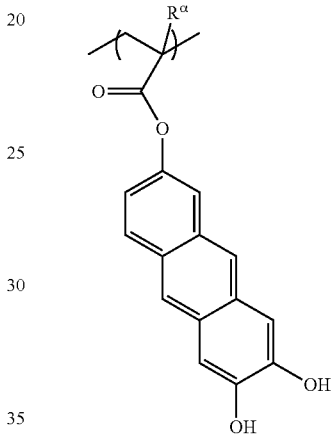

As the structural unit (a10) contained in the component (A1), 1 kind of structural unit may be used, or 2 or more kinds of structural units may be used.

When the component (A1) includes the structural unit (a10), the amount of the structural unit (a10) based on the combined total of all structural units constituting the component (A1) (100 mol %) is preferably 20 to 80 mol %, more preferably 25 to 70 mol %, and still more preferably 40 to 65 mol %.

When the amount of the structural unit (a10) is within the above-mentioned preferable range, proton source ability and solubility in a developing solution may be reliably assured, and the effects of the present invention may be more reliably achieved.

Structural Unit (a1):

The component (A1) may further include a structural unit (a1) containing an acid decomposable group that exhibits increased polarity by the action of acid (provided that structural units which fall under the definition of the structural unit (a0) are excluded).

Examples of the acid dissociable group for the structural unit (a1) include acid dissociable groups which have been proposed for a base resin of a chemically amplified resist composition, provided that the acid dissociable group "—$C^t$($R^{11}$)($R^2$)($R^{13}$)" in the aforementioned general formula (a0-1) is excluded.

Specific examples of acid dissociable groups for the base resin of a conventional chemically amplified resist include "acetal-type acid dissociable group", "tertiary alkyl ester-type acid dissociable group" and "tertiary alkyloxycarbonyl acid dissociable group" described below.

—Acetal-Type Acid Dissociable Group

Examples of the acid dissociable group for protecting the carboxy group or hydroxy group include the acid dissociable group represented by general formula (a1-r-1) shown below (hereafter, referred to as "acetal-type acid dissociable group").

[Chemical Formula 22]

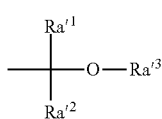

(a1-r-1)

In the formula, $Ra'^1$ and $Ra'^2$ represents a hydrogen atom or an alkyl group; and $Ra'^3$ represents a hydrocarbon group, provided that $Ra'^3$ may be bonded to $Ra'^1$ or $Ra'^2$.

In the formula (a1-r-1), it is preferable that at least one of $Ra'^1$ and $Ra'^2$ represents a hydrogen atom, and it is more preferable that both of $Ra'^1$ and $Ra'^2$ represent a hydrogen atom.

In the case where $Ra'^1$ or $Ra'^2$ is an alkyl group, as the alkyl group, the same alkyl groups as those described above the for the substituent which may be bonded to the carbon atom on the α-position of the aforementioned α-substituted acrylate ester can be mentioned, and an alkyl group of 1 to 5 carbon atoms is preferable. Specific examples include linear or branched alkyl groups. Specific examples of the alkyl group include a methyl group, an ethyl group, a propyl group, an isopropyl group, an n-butyl group, an isobutyl group, a tert-butyl group, a pentyl group, an isopentyl group and a neopentyl group. Of these, a methyl group or an ethyl group is preferable, and a methyl group is particularly preferable.

In formula (a1-r-1), examples of the hydrocarbon group for $Ra'^3$ include a linear or branched alkyl group and a cyclic hydrocarbon group.

The linear alkyl group preferably has 1 to 5 carbon atoms, more preferably 1 to 4, and still more preferably 1 or 2. Specific examples include a methyl group, an ethyl group, an n-propyl group, an n-butyl group and an n-pentyl group. Among these, a methyl group, an ethyl group or an n-butyl group is preferable, and a methyl group or an ethyl group is more preferable.

The branched alkyl group preferably has 3 to 10 carbon atoms, and more preferably 3 to 5. Specific examples include an isopropyl group, an isobutyl group, a tert-butyl group, an isopentyl group, a neopentyl group a 1,1-diethylpropyl group and a 2,2-dimethylbutyl group. Among these, an isopropyl group is preferable.

In the case where $Ra'^3$ represents a cyclic hydrocarbon group, the cyclic hydrocarbon group may be an aliphatic hydrocarbon group or an aromatic hydrocarbon group, and may be polycyclic or monocyclic.

As the monocyclic aliphatic hydrocarbon group, a group in which 1 hydrogen atom has been removed from a monocycloalkane is preferable. The monocycloalkane preferably has 3 to 6 carbon atoms, and specific examples thereof include cyclopentane and cyclohexane.

As the polycyclic aliphatic hydrocarbon group, a group in which 1 hydrogen atom has been removed from a polycycloalkane is preferable, and the polycyclic group preferably has 7 to 12 carbon atoms. Examples of the polycycloalkane include adamantane, norbornane, isobornane, tricyclodecane and tetracyclododecane.

When the monovalent hydrocarbon group for $Ra'^3$ is an aromatic hydrocarbon group, the aromatic hydrocarbon group is a hydrocarbon group having at least one aromatic ring.

The aromatic ring is not particularly limited, as long as it is a cyclic conjugated compound having (4n+2)π electrons, and may be either monocyclic or polycyclic. The aromatic ring preferably has 5 to 30 carbon atoms, more preferably 5 to 20, still more preferably 6 to 15, and most preferably 6 to 12. Examples of the aromatic ring include aromatic hydrocarbon rings, such as benzene, naphthalene, anthracene and phenanthrene; and aromatic hetero rings in which part of the carbon atoms constituting the aforementioned aromatic hydrocarbon rings has been substituted with a hetero atom. Examples of the hetero atom within the aromatic hetero rings include an oxygen atom, a sulfur atom and a nitrogen atom. Specific examples of the aromatic hetero ring include a pyridine ring and a thiophene ring.

Specific examples of the aromatic hydrocarbon group for $Ra'^3$ include a group in which one hydrogen atom has been removed from the aforementioned aromatic hydrocarbon ring or aromatic hetero ring (aryl group or heteroaryl group); a group in which one hydrogen atom has been removed from an aromatic compound having two or more aromatic rings (biphenyl, fluorene or the like); and a group in which one hydrogen atom of the aforementioned aromatic hydrocarbon ring or aromatic hetero ring has been substituted with an alkylene group (an arylalkyl group such as a benzyl group, a phenethyl group, a 1-naphthylmethyl group, a 2-naphthylmethyl group, a 1-naphthylethyl group, or a 2-naphthylethyl group). The alkylene group bonded to the aforementioned aromatic hydrocarbon ring or the aromatic hetero ring preferably has 1 to 4 carbon atoms, more preferably 1 or 2 carbon atoms, and most preferably 1 carbon atom.

In the case where $Ra'^3$ is bonded to $Ra'^1$ or $Ra'^2$ to form a ring, the cyclic group is preferably a 4 to 7-membered ring, and more preferably a 4 to 6-membered ring. Specific examples of the cyclic group include tetrahydropyranyl group and tetrahydrofuranyl group.

—Tertiary Alkyl Ester-Type Acid Dissociable Group

Examples of the acid dissociable group for protecting the carboxy group include the acid dissociable group represented by general formula (a1-r-2) shown below. Among the acid dissociable groups represented by general formula (a1-r-2), for convenience, a group which is constituted of alkyl groups is referred to as "tertiary ester-type acid dissociable group".

[Chemical Formula 23]

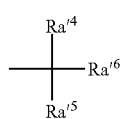

(a1-r-2)

In the formula, $Ra'^4$ to $Ra'^6$ each independently represents a hydrocarbon group, provided that $Ra'^5$ and $Ra'6$ may be mutually bonded to form a ring.

As the hydrocarbon group for $Ra'^4$ to $Ra'^6$, the same groups as those described above for $Ra'^3$ can be mentioned. $Ra'^4$ is preferably an alkyl group having from 1 to 5 carbon atoms. In the case where $Ra'^5$ and $Ra'6$ are mutually bonded to form a ring, a group represented by general formula (a1-r2-1) shown below may be mentioned. On the other hand, in the case where Ra'⁴ to Ra'⁶ are not mutually bonded and independently represent a hydrocarbon group, the group represented by general formula (a1-r2-2) shown below may be mentioned.

[Chemical Formula 24]

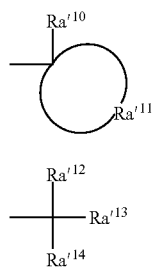

(a1-r2-1)

(a1-r2-2)

In the formulae $Ra'^{10}$ represents an alkyl group having 1 to 10 carbon atoms; $Ra'^{11}$ is a group which forms an alicyclic hydrocarbon group together with the carbon atom to which $Ra'^{10}$ is bonded; and $Ra'^{12}$ to $Ra'^{14}$ each independently represents a hydrocarbon group.

In the formula (a1-r2-1), as the alkyl group of 1 to 10 carbon atoms for $Ra'^{10}$, the same groups as described above for the linear or branched alkyl group for $Ra'^{3}$ in the formula (a1-r-1) are preferable. In the formula (a1-r2-1), as the alicyclic hydrocarbon group which is formed by $Ra'^{11}$ together with the carbon atom bonded to $Ra'^{10}$, the same groups as those described above for the monocyclic or polycyclic aliphatic hydrocarbon group for $Ra'^{3}$ in the formula (a1-r-1) are preferable.

In the formula (a1-r2-2), it is preferable that $Ra'^{12}$ and $Ra'^{14}$ each independently represents an alkyl group or 1 to 10 carbon atoms, and it is more preferable that the alkyl group is the same group as the described above for the linear or branched alkyl group for $Ra'^{3}$ in the formula (a1-r-1), it is still more preferable that the alkyl group is a linear alkyl group of 1 to 5 carbon atoms, and it is still more preferable that the alkyl group is a methyl group or an ethyl group.

In the formula (a1-r2-2), it is preferable that $Ra'^{13}$ is the same group as described above for the linear or branched alkyl group or monocyclic or polycyclic alicyclic hydrocarbon group for $Ra'^{3}$ in the formula (a1-r-1). Among these examples, monocyclic or polycyclic aliphatic hydrocarbon group for $Ra'^{3}$ are more preferable.

Specific examples of the group represented by the aforementioned formula (a1-r2-1) are shown below. and * represents a valence bond.

[Chemical Formula 25]

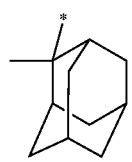

(r-pr-m1)

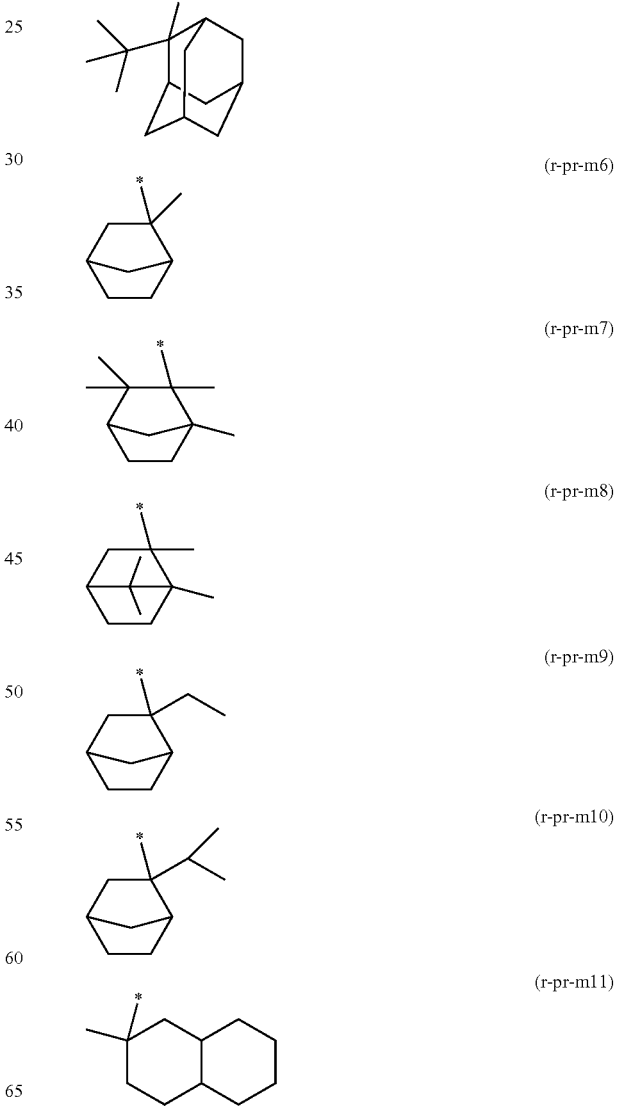

(r-pr-m2)

(r-pr-m3)

(r-pr-m4)

(r-pr-m5)

(r-pr-m6)

(r-pr-m7)

(r-pr-m8)

(r-pr-m9)

(r-pr-m10)

(r-pr-m11)

(r-pr-m12)
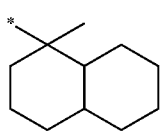
(r-pr-m13)
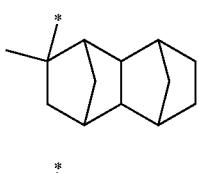
(r-pr-m14)
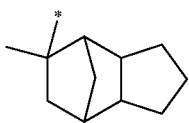
(r-pr-m15)
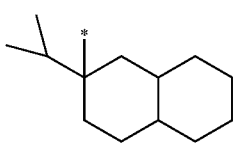
(r-pr-m16)
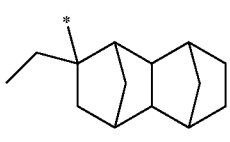
(r-pr-m17)
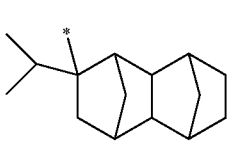
[Chemical Formula 26]
(r-pr-s1)
(r-pr-s2)
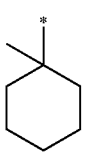
(r-pr-s3)
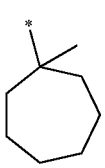
(r-pr-s4)
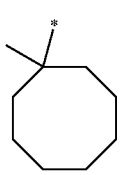
(r-pr-s5)
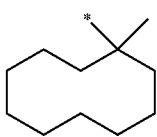
(r-pr-s6)
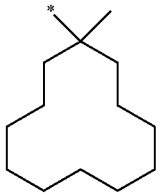
(r-pr-s7)
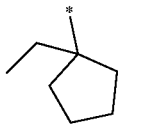
(r-pr-s8)
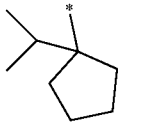
(r-pr-s9)
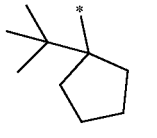
(r-pr-s10)
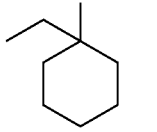
(r-pr-s11)
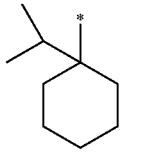
(r-pr-s12)
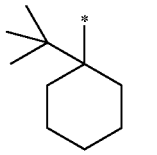
(r-pr-s13)
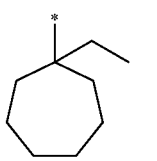
(r-pr-s14)
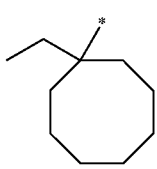

(r-pr-s15)
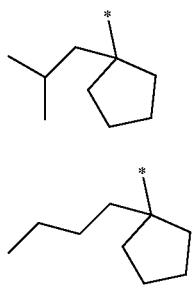

(r-pr-s16)

(r-pr-s17)
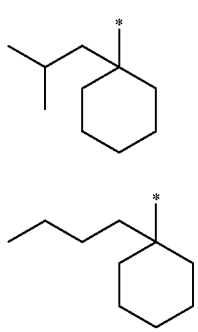

(r-pr-s18)

(r-pr-s19)
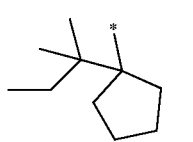

(r-pr-s20)
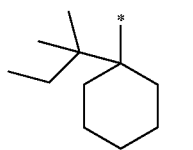

Specific examples of the group represented by the aforementioned formula (a1-r2-2) are shown below.

[Chemical Formula 27]

(r-pr-cm1)
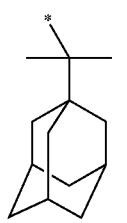

(r-pr-cm2)
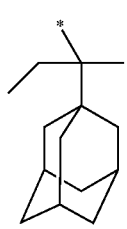

(r-pr-cm3)
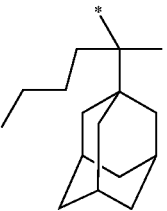

(r-pr-cm4)
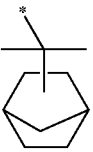

(r-pr-cs1)
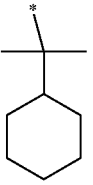

(r-pr-cs2)
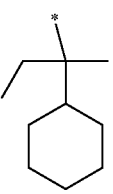

(r-pr-cs3)
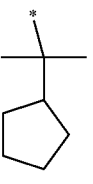

(r-pr-c1)

(r-pr-c2)

(r-pr-c3)
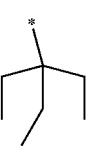

—Tertiary Alkyloxycarbonyl Acid Dissociable Group

Examples of the acid dissociable group for protecting a hydroxy group include the acid dissociable group represented by general formula (a1-r-3) shown below (hereafter, referred to as "tertiary alkyloxycarbonyl-type acid dissociable group").

[Chemical Formula 28]

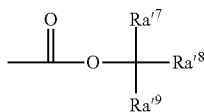

(a1-r-3)

In the formula, Ra'7 to Ra'9 each independently represents an alkyl group.

In formula (a1-r-3), each of $Ra'^7$ to $Ra'^9$ is preferably an alkyl group having 1 to 5 carbon atoms, and more preferably an alkyl group having 1 to 3 carbon atoms.

Further, the total number of carbon atoms within the alkyl group is preferably 3 to 7, more preferably 3 to 5, and most preferably 3 or 4.

Examples of the structural unit (a1) include a structural unit derived from an acrylate ester which may have the hydrogen atom bonded to the carbon atom on the α-position substituted with a substituent; a structural unit derived from an acrylamide; a structural unit derived from hydroxystyrene or a hydroxystyrene derivative in which at least a part of the hydrogen atom of the hydroxy group is protected with a substituent containing an acid decomposable group; and a structural unit derived from vinylbenzoic acid or a vinylbenzoic acid derivative in which at least a part of the hydrogen atom within —C(=O)—OH is protected with a substituent containing an acid decomposable group.

As the structural unit (a1), a structural unit derived from an acrylate ester which may have the hydrogen atom bonded to the carbon atom on the α-position substituted with a substituent is preferable. Specific examples of preferable structural units for the structural unit (a1) include structural units represented by general formula (a1-1) or (a1-2) shown below.

[Chemical Formula 29]

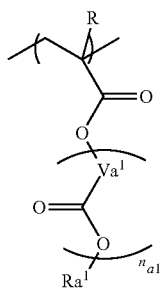

(a1-1)

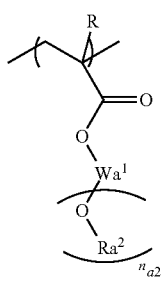

(a1-2)

In the formula, R represents a hydrogen atom, an alkyl group of 1 to 5 carbon atoms or a halogenated alkyl group of 1 to 5 carbon atoms; $Va^1$ represents a divalent hydrocarbon group optionally having an ether bond; $n_{a1}$ represents an integer of 0 to 2; $Ra^1$ represents an acid dissociable group represented by the aforementioned formula (a1-r-1) or (a1-r-2); $Wa^1$ represents a hydrocarbon group having a valency of $n_{a2}+1$; $n_{a2}$ represents an integer of 1 to 3; $Ra^2$ represents an acid dissociable group represented by the aforementioned formula (a1-r-1) or (a1-r-3).

In the aforementioned formula (a1-1), as the alkyl group of 1 to 5 carbon atoms for R, a linear or branched alkyl group of 1 to 5 carbon atoms is preferable, and specific examples thereof include a methyl group, an ethyl group, a propyl group, an isopropyl group, an n-butyl group, an isobutyl group, a tert-butyl group, a pentyl group, an isopentyl group and a neopentyl group. The halogenated alkyl group of 1 to 5 carbon atoms represented by R is a group in which part or all of the hydrogen atoms of the aforementioned alkyl group of 1 to 5 carbon atoms have been substituted with halogen atoms. As the halogen atom, a fluorine atom is most preferable.

As R, a hydrogen atom, an alkyl group of 1 to 5 carbon atoms or a fluorinated alkyl group of 1 to 5 carbon atoms is preferable, and a hydrogen atom or a methyl group is particularly desirable in terms of industrial availability.

In formula (a1-1), the divalent linking group for $Va^1$ is the same as defined for the divalent linking group for $Ya^{x0}$ described above in relation to $W^1$ in the aforementioned formula (a0-1).

In the aforementioned formula (a1-2), the hydrocarbon group for $Wa^1$ having a valency of $n_{a2}+1$ may be either an aliphatic hydrocarbon group or an aromatic hydrocarbon group. The aliphatic cyclic group refers to a hydrocarbon group that has no aromaticity, and may be either saturated or unsaturated, but is preferably saturated. Examples of the aliphatic hydrocarbon group include a linear or branched aliphatic hydrocarbon group, an aliphatic hydrocarbon group containing a ring in the structure thereof, and a combination of the linear or branched aliphatic hydrocarbon group and the aliphatic hydrocarbon group containing a ring in the structure thereof. The valency of $n_{a2}+1$ is preferably divalent, trivalent or tetravalent, and divalent or trivalent is more preferable.

Specific examples of structural unit represented by formula (a1-1) are shown below. In the formulae shown below, $R^α$ represents a hydrogen atom, a methyl group or a trifluoromethyl group.

[Chemical Formula 30]

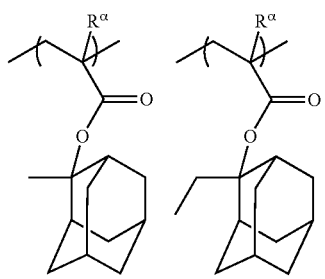

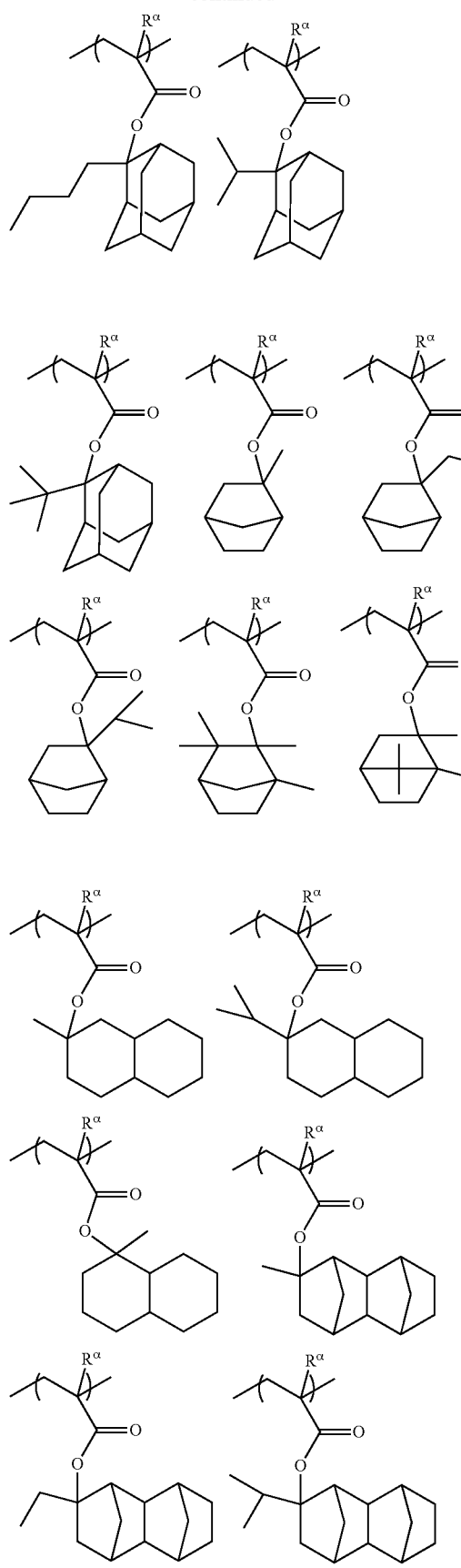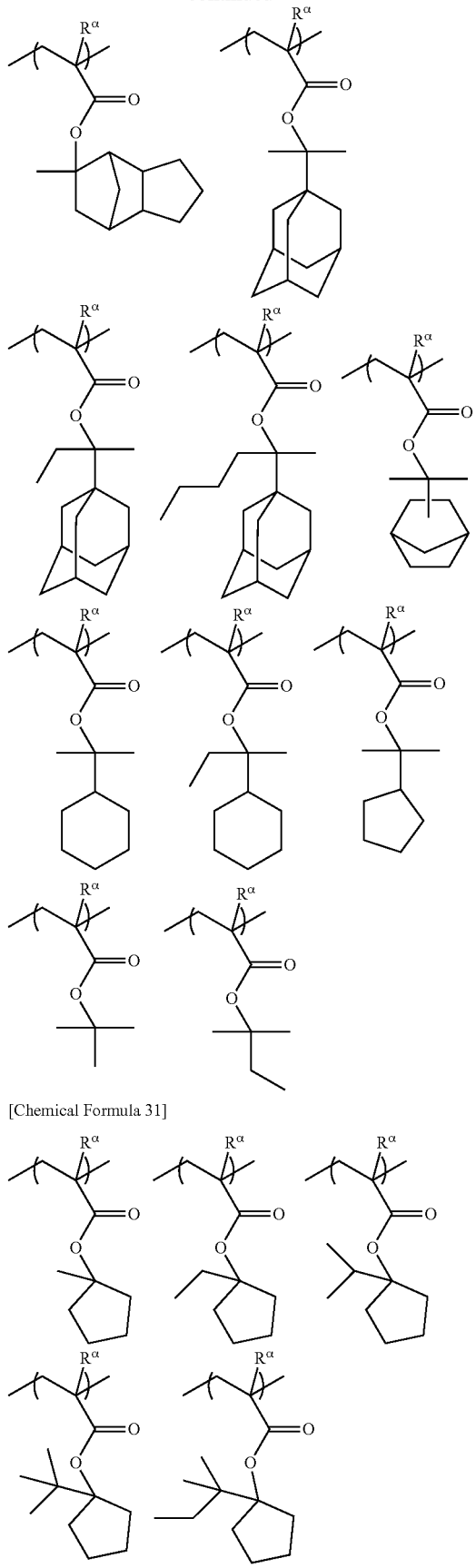
[Chemical Formula 31]

-continued

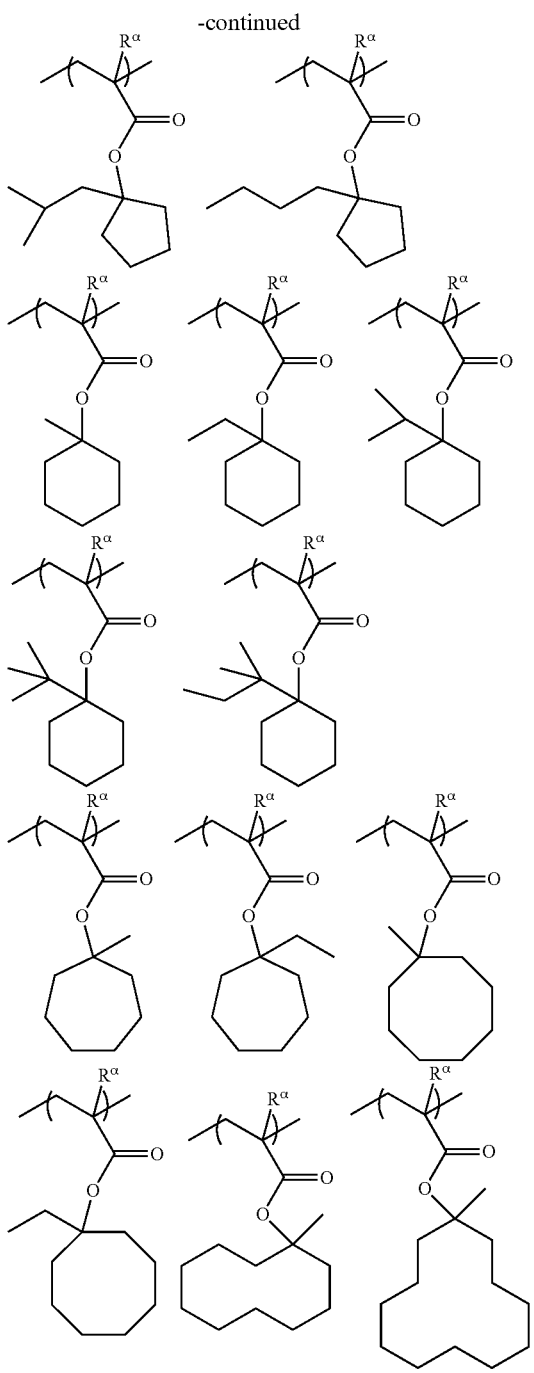

As the structural unit (a1) contained in the component (A1), 1 type of structural unit may be used, or 2 or more types may be used.

When the component (A1) includes the structural unit (a1), the amount of the structural unit (a1) based on the combined total of all structural units constituting the component (A1) (100 mol %) is preferably 1 to 50 mol %, more preferably 5 to 45 mol %, and still more preferably 5 to 30 mol %. When the amount of the structural unit (a1) is at least as large as the lower limit of the above-mentioned range, a resist pattern can be reliably obtained, and the sensitivity, resolution, roughness and various lithography properties such as EL margin are further improved. On the other hand, when the amount of the structural unit (a1) is no more than the upper limit of the above-mentioned range, a good balance can be achieved with the other structural units.

Structural Unit (a2):

The component (A1) may further include a structural unit (a2) which contains a lactone-containing cyclic group, an —$SO_2$— containing cyclic group or a carbonate-containing cyclic group.

When the component (A1) is used for forming a resist film, the lactone-containing cyclic group, the —$SO_2$— containing cyclic group or the carbonate-containing cyclic group within the structural unit (a2) is effective in improving the adhesion between the resist film and the substrate. In addition, by virtue of containing the structural unit (a2), for example, the acid diffusion length is appropriately adjusted, the adhesion of the resist film to the substrate is enhanced, or the solubility during development is appropriately adjusted. As a result, the lithography properties are enhanced.

The term "lactone-containing cyclic group" refers to a cyclic group including a ring containing a —O—C(=O)— structure (lactone ring). The term "lactone ring" refers to a single ring containing a —O—C(O)— structure, and this ring is counted as the first ring. A lactone-containing cyclic group in which the only ring structure is the lactone ring is referred to as a monocyclic group, and groups containing other ring structures are described as polycyclic groups regardless of the structure of the other rings. The lactone-containing cyclic group may be either a monocyclic group or a polycyclic group.

The lactone-containing cyclic group for the structural unit (a2) is not particularly limited, and an arbitrary structural unit may be used. Specific examples include groups represented by general formulae (a2-r-1) to (a2-r-7) shown below.

[Chemical Formula 32]

(a2-r-1)
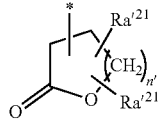

(a2-r-2)
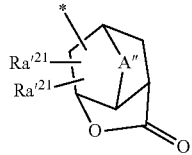

(a2-r-3)
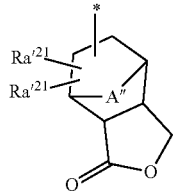

(a2-r-4)
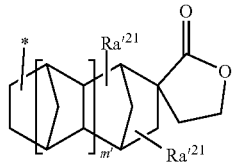

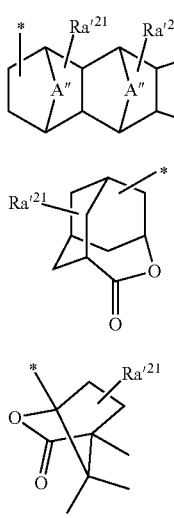

(a2-r-5)

(a2-r-6)

(a2-r-7)

In the formulae, each $Ra'^{21}$ independently represents a hydrogen atom, an alkyl group, an alkoxy group, a halogen atom, a halogenated alkyl group, a hydroxy group, —COOR", —OC(=O)R", a hydroxyalkyl group or a cyano group; R" represents a hydrogen atom, an alkyl group, a lactone-containing cyclic group, a carbonate-containing cyclic group or an —$SO_2$— containing cyclic group; A" represents an oxygen atom (—O—), a sulfur atom (—S—) or an alkylene group of 1 to 5 carbon atoms which may contain an oxygen atom or a sulfur atom; n' represents an integer of 0 to 2; and m' represents 0 or 1.

In formulae (a2-r-1) to (a2-r-7), the alkyl group for $Ra'^{21}$ is preferably an alkyl group of 1 to 6 carbon atoms. Further, the alkyl group is preferably a linear alkyl group or a branched alkyl group. Specific examples include a methyl group, an ethyl group, a propyl group, an isopropyl group, an n-butyl group, an isobutyl group, a tert-butyl group, a pentyl group, an isopentyl group, a neopentyl group and a hexyl group. Among these, a methyl group or ethyl group is preferable, and a methyl group is particularly desirable.

The alkoxy group for $Ra'^{21}$ is preferably an alkoxy group of 1 to 6 carbon atoms. Further, the alkoxy group is preferably a linear or branched alkoxy group. Specific examples of the alkoxy groups include the aforementioned alkyl groups for $Ra'^{21}$ having an oxygen atom (—O—) bonded thereto.

The halogen atom for $Ra'^{21}$ is preferably a fluorine atom.

Examples of the halogenated alkyl group for $Ra'^{21}$ include groups in which part or all of the hydrogen atoms within the aforementioned alkyl group for $Ra'^{21}$ has been substituted with the aforementioned halogen atoms. As the halogenated alkyl group, a fluorinated alkyl group is preferable, and a perfluoroalkyl group is particularly desirable.

With respect to —COOR" and —OC(=O)R" for $Ra'^{21}$, R" represents a hydrogen atom, an alkyl group, a lactone-containing cyclic group, a carbonate-containing cyclic group or an —$SO_2$— containing cyclic group.

The alkyl group for R" may be linear, branched or cyclic, and preferably has 1 to 15 carbon atoms.

When R" represents a linear or branched alkyl group, it is preferably an alkyl group of 1 to 10 carbon atoms, more preferably an alkyl group of 1 to 5 carbon atoms, and most preferably a methyl group or an ethyl group.

When R" is a cyclic alkyl group (cycloalkyl group), it preferably has 3 to 15 carbon atoms, more preferably 4 to 12 carbon atoms, and most preferably 5 to 10 carbon atoms. Specific examples include groups in which one or more hydrogen atoms have been removed from a monocycloalkane or a polycycloalkane such as a bicycloalkane, tricycloalkane or tetracycloalkane which may or may not be substituted with a fluorine atom or a fluorinated alkyl group. Specific examples include groups in which one or more hydrogen atoms have been removed from a monocycloalkane such as cyclopentane or cyclohexane; and groups in which one or more hydrogen atoms have been removed from a polycycloalkane such as adamantane, norbornane, isobornane, tricyclodecane or tetracyclododecane.

Examples of the lactone-containing cyclic group for R" include groups represented by the aforementioned general formulae (a2-r-1) to (a2-r-7).

The carbonate-containing cyclic group for R" is the same as defined for the carbonate-containing cyclic group described later. Specific examples of the carbonate-containing cyclic group include groups represented by general formulae (ax3-r-1) to (ax3-r-3).

The —$SO_2$— containing cyclic group for R" is the same as defined for the —$SO_2$— containing cyclic group described later. Specific examples of the —$SO_2$— containing cyclic group include groups represented by general formulae (a5-r-1) to (a5-r-4).

The hydroxyalkyl group for $Ra'^{21}$ preferably has 1 to 6 carbon atoms, and specific examples thereof include the alkyl groups for $Ra'^{21}$ in which at least one hydrogen atom has been substituted with a hydroxy group.

In formulae (a2-r-2), (a2-r-3) and (a2-r-5), as the alkylene group of 1 to 5 carbon atoms represented by A", a linear or branched alkylene group is preferable, and examples thereof include a methylene group, an ethylene group, an n-propylene group and an isopropylene group. Examples of alkylene groups that contain an oxygen atom or a sulfur atom include the aforementioned alkylene groups in which —O— or —S— is bonded to the terminal of the alkylene group or present between the carbon atoms of the alkylene group. Specific examples of such alkylene groups include O—$CH_2$—, —$CH_2$—O—$CH_2$—, —S—$CH_2$—, and —$CH_2$—S—$CH_2$—. As A", an alkylene group of 1 to 5 carbon atoms or —O— is preferable, more preferably an alkylene group of 1 to 5 carbon atoms, and most preferably a methylene group.

Specific examples of the groups represented by the aforementioned general formulae (a2-r-1) to (a2-r-7) are shown below.

[Chemical Formula 33]

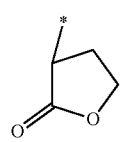

(r-lc-1-1)

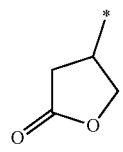

(r-lc-1-2)

-continued
(r-lc-1-3)
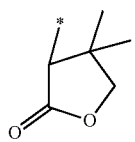
(r-lc-1-4)
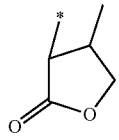
(r-lc-1-5)
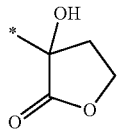
(r-lc-1-6)
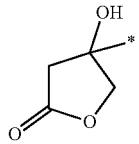
(r-lc-1-7)
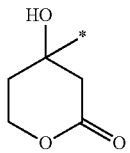
(r-lc-2-1)
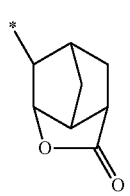
(r-lc-2-2)
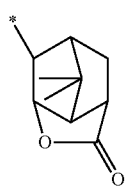
(r-lc-2-3)
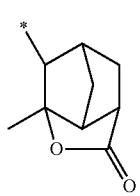
(r-lc-2-4)
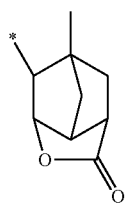
-continued
(r-lc-2-5)
(r-lc-2-6)
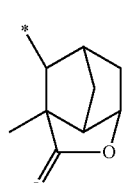
(r-lc-2-7)
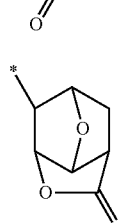
(r-lc-2-8)
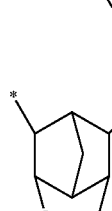
(r-lc-2-9)
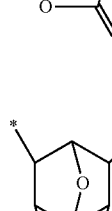
(r-lc-2-10)
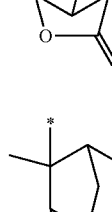
(r-lc-2-11)
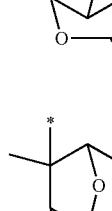
(r-lc-2-12)
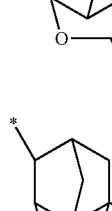
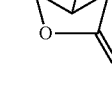

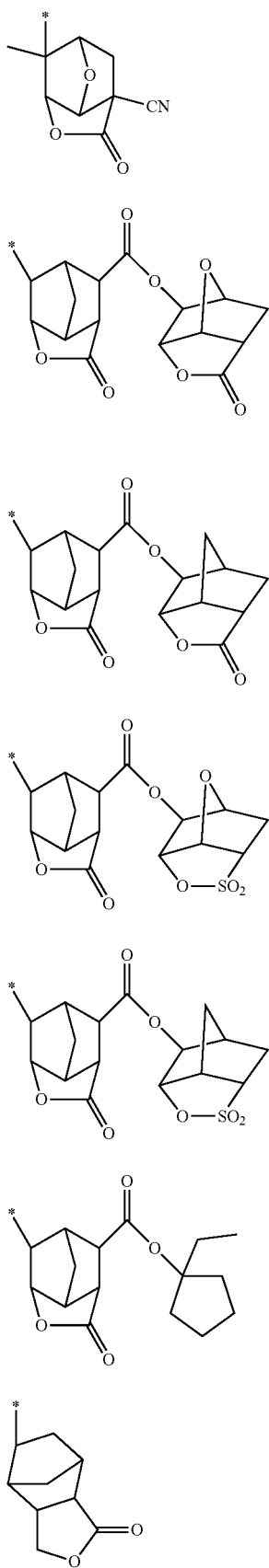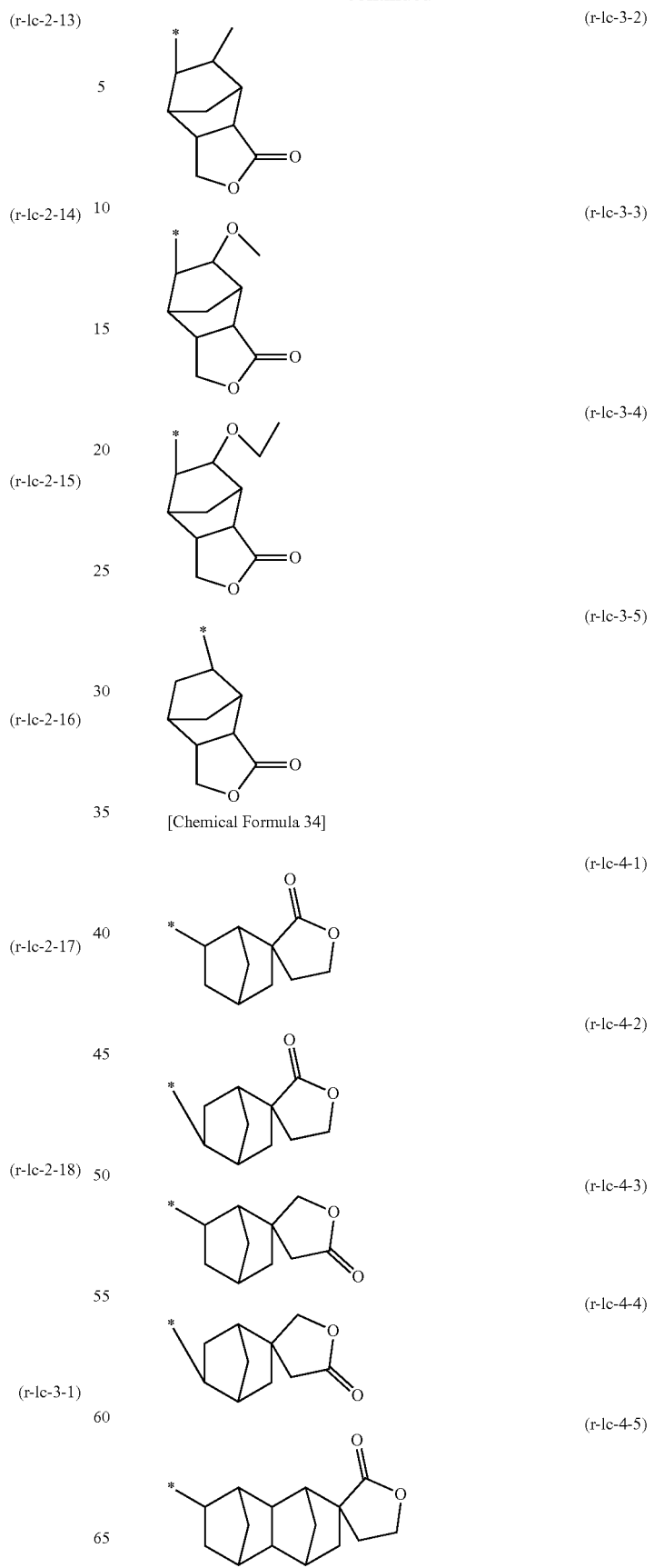
[Chemical Formula 34]

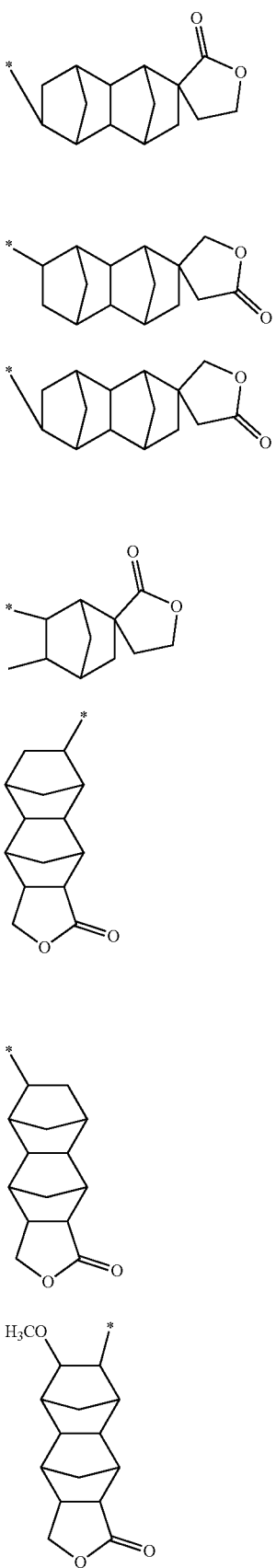

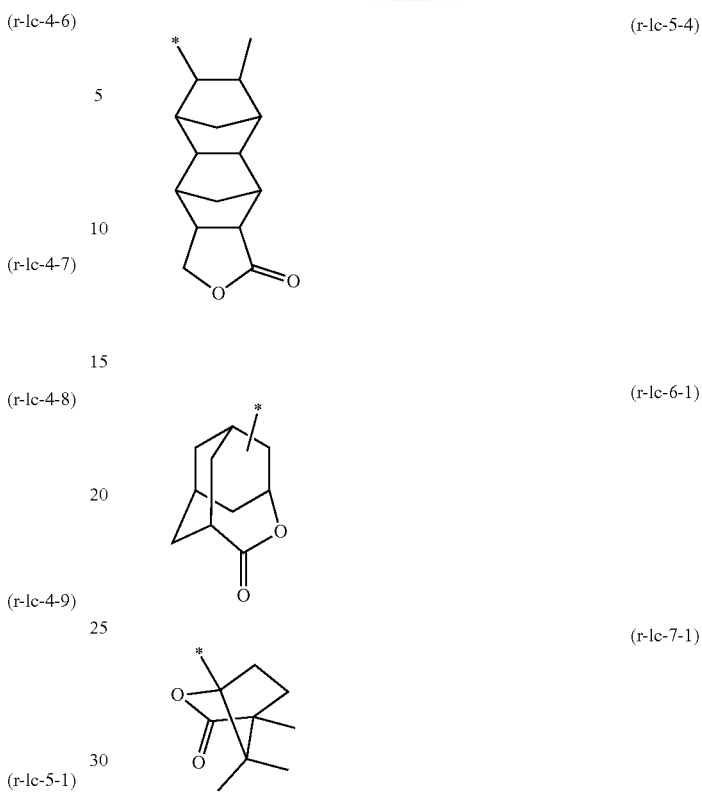

An "—SO₂— containing cyclic group" refers to a cyclic group having a ring containing —SO₂— within the ring structure thereof, i.e., a cyclic group in which the sulfur atom (S) within —SO₂— forms part of the ring skeleton of the cyclic group. The ring containing —SO₂— within the ring skeleton thereof is counted as the first ring. A cyclic group in which the only ring structure is the ring that contains —SO₂— in the ring skeleton thereof is referred to as a monocyclic group, and a group containing other ring structures is described as a polycyclic group regardless of the structure of the other rings. The —SO₂— containing cyclic group may be either a monocyclic group or a polycyclic group. As the —SO₂— containing cyclic group, a cyclic group containing —O—SO₂— within the ring skeleton thereof, i.e., a cyclic group containing a sultone ring in which —O—S— within the —O—SO₂— group forms part of the ring skeleton thereof is particularly desirable.

More specific examples of the —SO₂— containing cyclic group include groups represented by general formulas (a5-r-1) to (a5-r-4) shown below.

[Chemical Formla 35]

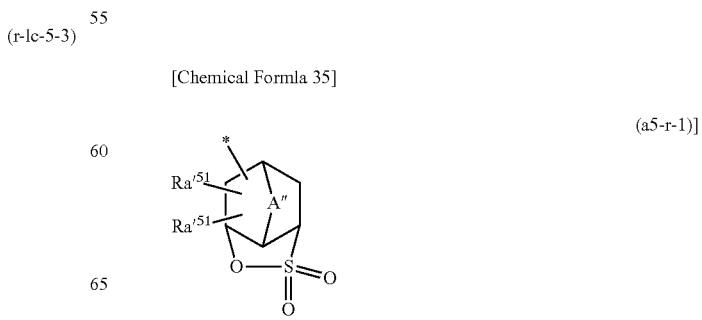

-continued (a5-r-2)
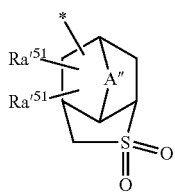

(a5-r-3)
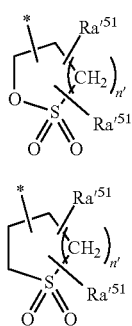

(a5-r-4)

In the formulae, each $Ra'^{51}$ independently represents a hydrogen atom, an alkyl group, an alkoxy group, a halogen atom, a halogenated alkyl group, a hydroxy group, —COOR", —OC(═O)R", a hydroxyalkyl group or a cyano group; R" represents a hydrogen atom, an alkyl group, a lactone-containing cyclic group, a carbonate-containing cyclic group or an —SO$_2$— containing cyclic group; A" represents an oxygen atom, a sulfur atom or an alkylene group of 1 to 5 carbon atoms which may contain an oxygen atom or a sulfur atom; and n' represents an integer of 0 to 2.

In general formulae (a5-r-1) and (a5-r-2), A" is the same as defined for A" in general formulae (a2-r-2), (a2-r-3) and (a2-r-5).

Examples of the alkyl group, alkoxy group, halogen atom, halogenated alkyl group, —COOR", —OC(═O)R" and hydroxyalkyl group for $Ra'^{21}$ include the same groups as those described above in the explanation of $Ra'^{21}$ in the general formulas (a2-r-1) to (a2-r-7).

Specific examples of the groups represented by the aforementioned general formulae (a5-r-1) to (a5-r-4) are shown below. In the formulae shown below, "Ac" represents an acetyl group.

[Chemical Formula 36]

(r-sl-1-1)
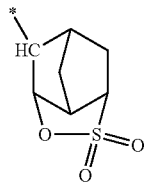

(r-sl-1-2)
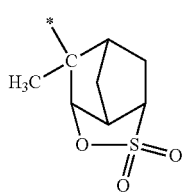

(r-sl-1-3)
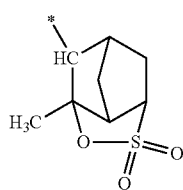

(r-sl-1-4)
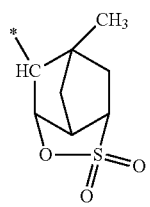

(r-sl-1-5)
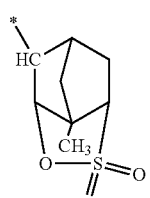

(r-sl-1-6)
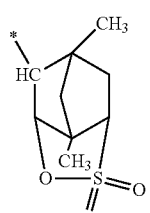

(r-sl-1-7)
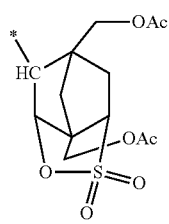

(r-sl-1-8)

(r-sl-1-9)
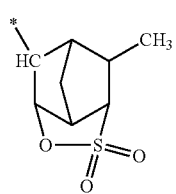

| | |
|---|---|
| 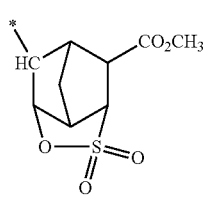 (r-sl-1-10) | 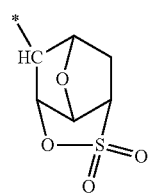 (r-sl-1-18) |
| 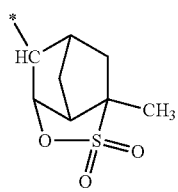 (r-sl-1-11) | 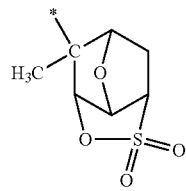 (r-sl-1-19) |
| 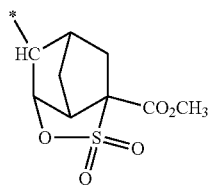 (r-sl-1-12) | 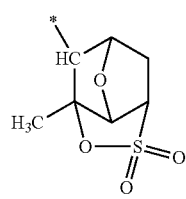 (r-sl-1-20) |
| 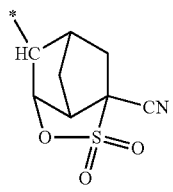 (r-sl-1-13) | 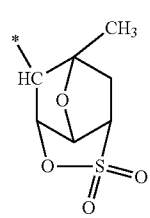 (r-sl-1-21) |
| 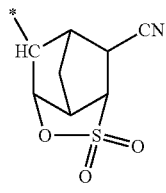 (r-sl-1-14) | |
[Chemical Formula 37]
| | |
|---|---|
| 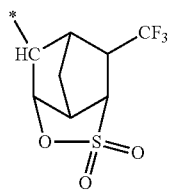 (r-sl-1-15) | 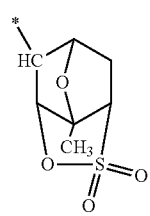 (r-sl-1-22) |
| 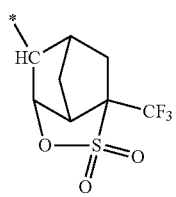 (r-sl-1-16) | 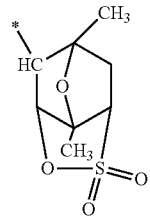 (r-sl-1-23) |
| 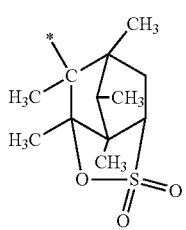 (r-sl-1-17) | 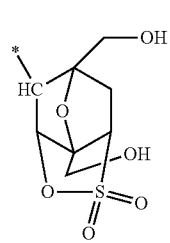 (r-sl-1-24) |

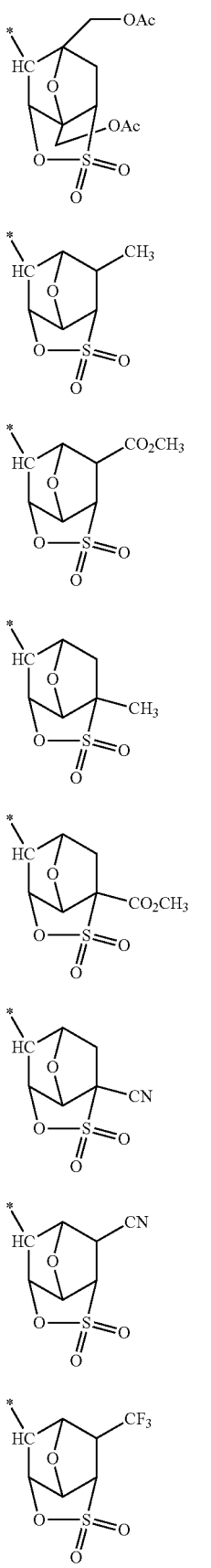
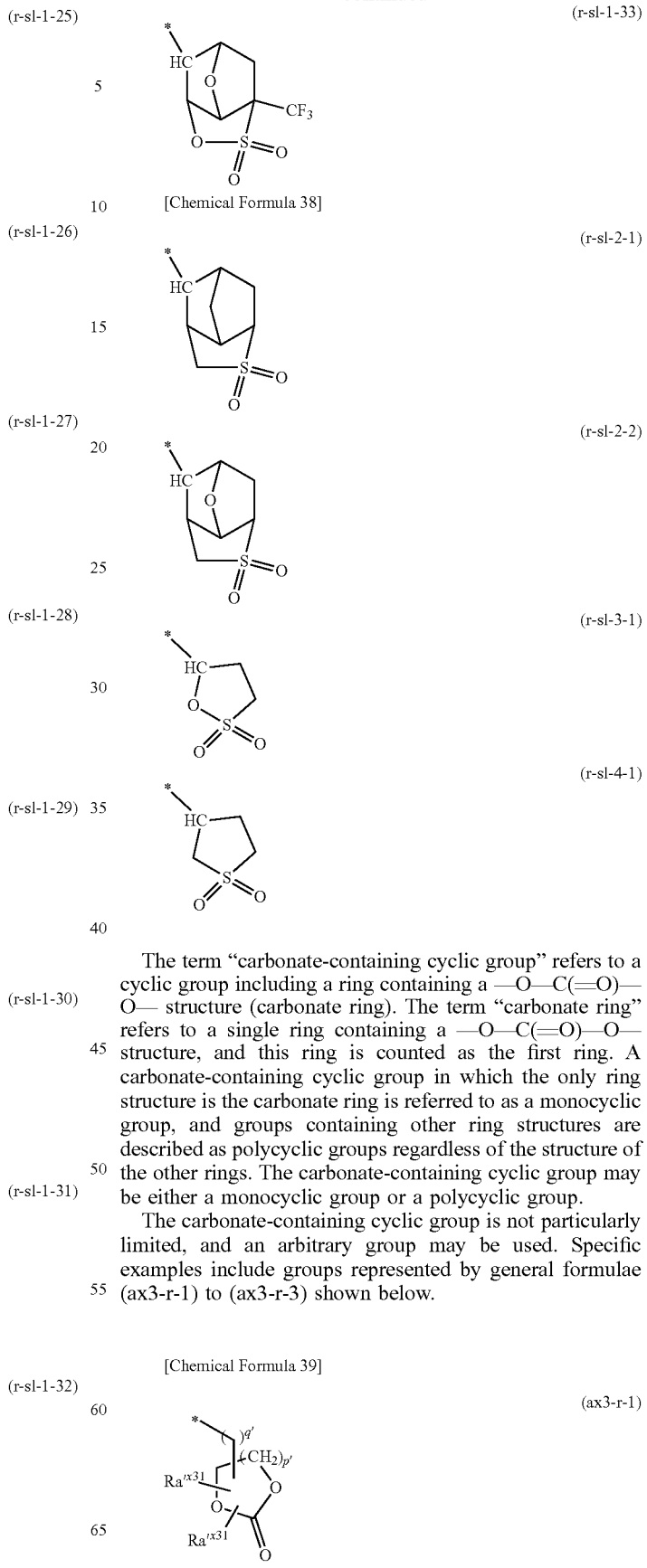

The term "carbonate-containing cyclic group" refers to a cyclic group including a ring containing a —O—C(=O)—O— structure (carbonate ring). The term "carbonate ring" refers to a single ring containing a —O—C(=O)—O— structure, and this ring is counted as the first ring. A carbonate-containing cyclic group in which the only ring structure is the carbonate ring is referred to as a monocyclic group, and groups containing other ring structures are described as polycyclic groups regardless of the structure of the other rings. The carbonate-containing cyclic group may be either a monocyclic group or a polycyclic group.

The carbonate-containing cyclic group is not particularly limited, and an arbitrary group may be used. Specific examples include groups represented by general formulae (ax3-r-1) to (ax3-r-3) shown below.

[Chemical Formula 39]

-continued

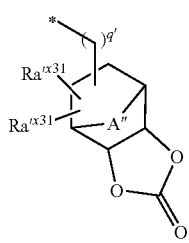
(ax3-r-2)

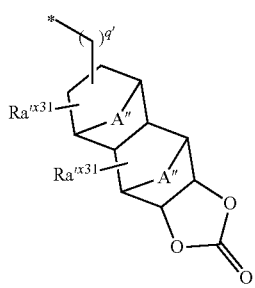
(ax3-r-3)

In the formulae, each Ra'$^{x31}$ independently represents a hydrogen atom, an alkyl group, an alkoxy group, a halogen atom, a halogenated alkyl group, a hydroxy group, —COOR", —OC(=O)R", a hydroxyalkyl group or a cyano group; R" represents a hydrogen atom, an alkyl group, a lactone-containing cyclic group, a carbonate-containing cyclic group or an —SO$_2$— containing cyclic group; A" represents an oxygen atom, a sulfur atom or an alkylene group of 1 to 5 carbon atoms which may contain an oxygen atom or a sulfur atom; p' represents an integer of 0 to 3; and q' represents 0 or 1.

In general formulae (ax3-r-2) and (ax3-r-3), A" is the same as defined for A" in general formulae (a2-r-2), (a2-r-3) and (a2-r-5).

Examples of the alkyl group, alkoxy group, halogen atom, halogenated alkyl group, —COOR", —OC(=O)R" and hydroxyalkyl group for Ra'$^{31}$ include the same groups as those described above in the explanation of Ra'$^{21}$ in the general formulas (a2-r-1) to (a2-r-7).

Specific examples of the groups represented by the aforementioned general formulae (ax3-r-1) to (ax3-r-3) are shown below.

[Chemical Formula 40]

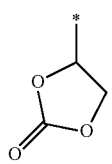
(r-cr-1-1)

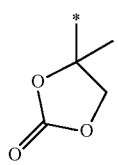
(r-cr-1-2)

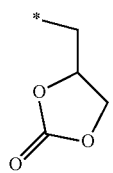
(r-cr-1-3)

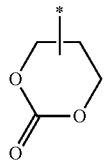
(r-cr-1-4)

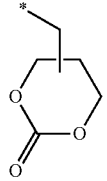
(r-cr-1-5)

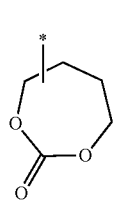
(r-cr-1-6)

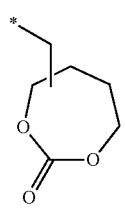
(r-cr-1-7)

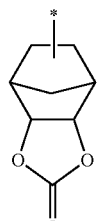
(r-cr-2-1)

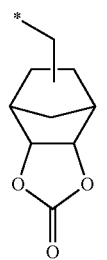
(r-cr-2-2)

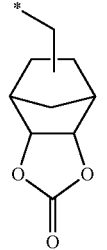

(r-cr-2-3)

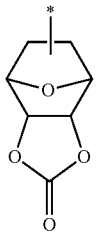

(r-cr-2-4)

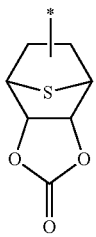

(r-cr-3-1)

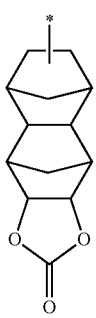

(r-cr-3-2)

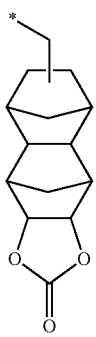

(r-cr-3-3)

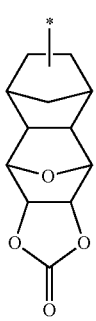

(r-cr-3-4)

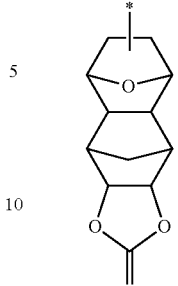

(r-cr-3-5)

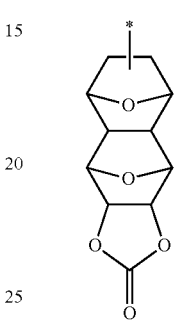

As the structural unit (a2), a structural unit derived from an acrylate ester which may have the hydrogen atom bonded to the carbon atom on the α-position substituted with a substituent is preferable.

The structural unit (a2) is preferably a structural unit represented by general formula (a2-1) shown below.

[Chemical Formula 41]

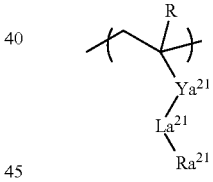

(a2-1)

In the formula, R represents a hydrogen atom, an alkyl group of 1 to 5 carbon atoms or a halogenated alkyl group of 1 to 5 carbon atoms; $Ya^{21}$ represents a single bond or a divalent linking group; $La^{21}$ represents —O—, —COO—, —CON(R')—, —OCO—, —CONHCO— or —CONHCS—; and R' represents a hydrogen atom or a methyl group; provided that, when $La^{21}$ represents —O—, $Ya^{21}$ does not represents —CO—; and $Ra^{21}$ represents a lactone-containing cyclic group, a carbonate-containing cyclic group or an —$SO_2$— containing cyclic group.

In the formula (a2-1), R is the same as defined above. As R, a hydrogen atom, an alkyl group of 1 to 5 carbon atoms or a fluorinated alkyl group of 1 to 5 carbon atoms is preferable, and a hydrogen atom or a methyl group is particularly desirable in terms of industrial availability.

In the formula (a2-1), the divalent linking group for $Ya^{21}$ is not particularly limited, and preferable examples thereof include a divalent hydrocarbon group which may have a substituent and a divalent linking group containing a hetero atom.

—Divalent Hydrocarbon Group which May have a Substituent:

In the case where $Ya^{21}$ is a divalent linking group which may have a substituent, the hydrocarbon group may be either an aliphatic hydrocarbon group or an aromatic hydrocarbon group.

—Aliphatic Hydrocarbon Group for $Ya^{21}$

An "aliphatic hydrocarbon group" refers to a hydrocarbon group that has no aromaticity. The aliphatic hydrocarbon group may be saturated or unsaturated. In general, the aliphatic hydrocarbon group is preferably saturated. Examples of the aliphatic hydrocarbon group include a linear or branched aliphatic hydrocarbon group, and an aliphatic hydrocarbon group containing a ring in the structure thereof can be given.

—Linear or Branched Aliphatic Hydrocarbon Group

The linear aliphatic hydrocarbon group preferably has 1 to 10 carbon atoms, more preferably 1 to 6, still more preferably 1 to 4, and most preferably 1 to 3.

As the linear aliphatic hydrocarbon group, a linear alkylene group is preferable. Specific examples thereof include a methylene group [—$CH_2$—], an ethylene group [—$(CH_2)_2$—], a trimethylene group [—$(CH_2)_3$—], a tetramethylene group [—$(CH_2)_4$—] and a pentamethylene group [—$(CH_2)_5$—].

The branched aliphatic hydrocarbon group preferably has 2 to 10 carbon atoms, more preferably 3 to 6, still more preferably 3 or 4, and most preferably 3.

As the branched aliphatic hydrocarbon group, branched alkylene groups are preferred, and specific examples include various alkylalkylene groups, including alkylmethylene groups such as —$CH(CH_3)$—, —$CH(CH_2CH_3)$—, —$C(CH_3)_2$—, —$C(CH_3)(CH_2CH_3)$—, —$C(CH_3)(CH_2CH_2CH_3)$—, and —$C(CH_2CH_3)_2$—; alkylethylene groups such as —$CH(CH_3)CH_2$—, —$CH(CH_3)CH(CH_3)$—, —$C(CH_3)_2CH_2$—, —$CH(CH_2CH_3)CH_2$—, and —$C(CH_2CH_3)_2$—$CH_2$—; alkyltrimethylene groups such as —$CH(CH_3)CH_2CH_2$—, and —$CH_2CH(CH_3)CH_2$—; and alkyltetramethylene groups such as —$CH(CH_3)CH_2CH_2CH_2$—, and —$CH_2CH(CH_3)CH_2CH_2$—. As the alkyl group within the alkylalkylene group, a linear alkyl group of 1 to 5 carbon atoms is preferable.

The linear or branched aliphatic hydrocarbon group may or may not have a substituent. Examples of the substituent include a fluorine atom, a fluorinated alkyl group of 1 to 5 carbon atoms, and a carbonyl group.

—Aliphatic Hydrocarbon Group Containing a Ring in the Structure Thereof

As examples of the hydrocarbon group containing a ring in the structure thereof, a cyclic aliphatic hydrocarbon group containing a hetero atom in the ring structure thereof and may have a substituent (a group in which two hydrogen atoms have been removed from an aliphatic hydrocarbon ring), a group in which the cyclic aliphatic hydrocarbon group is bonded to the terminal of the aforementioned chain-like aliphatic hydrocarbon group, and a group in which the cyclic aliphatic group is interposed within the aforementioned linear or branched aliphatic hydrocarbon group, can be given. As the linear or branched aliphatic hydrocarbon group, the same groups as those described above can be used.

The cyclic aliphatic hydrocarbon group preferably has 3 to 20 carbon atoms, and more preferably 3 to 12 carbon atoms.

The cyclic aliphatic hydrocarbon group may be either a polycyclic group or a monocyclic group. As the monocyclic aliphatic hydrocarbon group, a group in which 2 hydrogen atoms have been removed from a monocycloalkane is preferable. The monocycloalkane preferably has 3 to 6 carbon atoms, and specific examples thereof include cyclopentane and cyclohexane. As the polycyclic group, a group in which 2 hydrogen atoms have been removed from a polycycloalkane is preferable, and the polycyclic group preferably has 7 to 12 carbon atoms. Examples of the polycycloalkane include adamantane, norbornane, isobornane, tricyclodecane and tetracyclododecane.

The cyclic aliphatic hydrocarbon group may or may not have a substituent. Examples of the substituent include an alkyl group, an alkoxy group, a halogen atom, a halogenated alkyl group, a hydroxyl group and a carbonyl group.

The alkyl group as the substituent is preferably an alkyl group of 1 to 5 carbon atoms, and more preferably a methyl group, an ethyl group, a propyl group, an n-butyl group or a tert-butyl group.

The alkoxy group as the substituent is preferably an alkoxy group having 1 to 5 carbon atoms, more preferably a methoxy group, ethoxy group, n-propoxy group, isopropoxy group, n-butoxy group or tert-butoxy group, and still more preferably a methoxy group or an ethoxy group.

The halogen atom as the substituent is preferably a fluorine atom.

Examples of the halogenated alkyl group for the substituent include groups in which part or all of the hydrogen atoms within the aforementioned alkyl groups has been substituted with the aforementioned halogen atoms.

The cyclic aliphatic hydrocarbon group may have part of the carbon atoms constituting the ring structure thereof substituted with a substituent containing a hetero atom. As the substituent containing a hetero atom, —O—, —C(=O)—O—, —S—, —S(=O)$_2$— or —S(=O)$_2$—O— is preferable.

—Aromatic Hydrocarbon Group for $Ya^{21}$

The aromatic hydrocarbon group is a hydrocarbon group having at least one aromatic ring.

The aromatic ring is not particularly limited, as long as it is a cyclic conjugated compound having $(4n+2)\pi$ electrons, and may be either monocyclic or polycyclic. The aromatic ring preferably has 5 to 30 carbon atoms, more preferably 5 to 20 carbon atoms, and still more preferably 6 to 15 carbon atoms, and most preferably 6 to 12 carbon atoms. Here, the number of carbon atoms within a substituent(s) is not included in the number of carbon atoms of the aromatic hydrocarbon group.

Examples of the aromatic ring include aromatic hydrocarbon rings, such as benzene, naphthalene, anthracene and phenanthrene; and aromatic hetero rings in which part of the carbon atoms constituting the aforementioned aromatic hydrocarbon rings has been substituted with a hetero atom. Examples of the hetero atom within the aromatic hetero rings include an oxygen atom, a sulfur atom and a nitrogen atom. Specific examples of the aromatic hetero ring include a pyridine ring and a thiophene ring.

Specific examples of the aromatic hydrocarbon group include a group in which two hydrogen atoms have been removed from the aforementioned aromatic hydrocarbon ring or aromatic hetero ring (arylene group or heteroarylene group); a group in which two hydrogen atoms have been removed from an aromatic compound having two or more aromatic rings (biphenyl, fluorene or the like); and a group in which one hydrogen atom of the aforementioned aromatic hydrocarbon ring or aromatic hetero ring has been substituted with an alkylene group (a group in which one hydrogen atom has been removed from the aryl group within the aforementioned arylalkyl group such as a benzyl group, a phenethyl group, a 1-naphthylmethyl group, a 2-naphthylmethyl group, a 1-naphthylethyl group, or a 2-naphthylethyl group, or a heteroarylalkyl group). The alkylene group which is bonded to the aforementioned aryl group or heteroaryl group preferably has 1 to 4 carbon atoms, more preferably 1 or 2 carbon atoms, and most preferably 1 carbon atom.

With respect to the aromatic hydrocarbon group, the hydrogen atom within the aromatic hydrocarbon group may be substituted with a substituent. For example, the hydrogen atom bonded to the aromatic ring within the aromatic hydrocarbon group may be substituted with a substituent. Examples of substituents include an alkyl group, an alkoxy group, a halogen atom, a halogenated alkyl group, and a hydroxyl group.

The alkyl group as the substituent is preferably an alkyl group of 1 to 5 carbon atoms, and more preferably a methyl group, an ethyl group, a propyl group, an n-butyl group or a tert-butyl group.

As the alkoxy group, the halogen atom and the halogenated alkyl group for the substituent, the same groups as the aforementioned substituent groups for substituting a hydrogen atom within the cyclic aliphatic hydrocarbon group can be used.

—Divalent Linking Group Containing a Hetero Atom

In the case where $Ya^{21}$ is a divalent linking group containing a hetero atom, examples of the linking group include —O—, —C(=O)—O—, —O—C(=O)—, —C(=O)—, —O—C(=O)—O—, —C(=O)—NH—, —NH—, —NH—C(=NH)— (H may be substituted with a substituent such as an alkyl group or an acyl group), —S—, —S(=O)$_2$—, —S(=O)$_2$—O—, and a group represented by general formula —$Y^{21}$—O—$Y^{22}$—, —$Y^{21}$—O—, —$Y^{21}$—C(=O)—O—, —C(=O)—O—$Y^{21}$—, —[$Y^{21}$—C(=O)—O]$_{m''}$—$Y^{22}$—, —$Y^{21}$—O—C(=O)—$Y^{22}$— or —$Y^{21}$—S(=O)$_2$—O—$Y^{22}$— [in the formulae, $Y^{21}$ and $Y^{22}$ each independently represents a divalent hydrocarbon group which may have a substituent, O represents an oxygen atom, and m'' represents an integer of 0 to 3.

In the case where the divalent linking group containing a hetero atom is —C(=O)—NH—, —C(=O)—NH—C(=O)—, —NH— or —NH—C(=NH)—, H may be substituted with a substituent such as an alkyl group, an acyl group or the like. The substituent (an alkyl group, an acyl group or the like) preferably has 1 to 10 carbon atoms, more preferably 1 to 8, and most preferably 1 to 5.

In general formulae —$Y^{21}$—O—$Y^{22}$—, —$Y^{21}$—O—, —$Y^{21}$—C(=O)—O—, —C(=O)—O—$Y^{21}$—, —[$Y^{21}$—C(=O)—O]$_{m''}$—$Y^{22}$—, —$Y^{21}$—O—C(=O)—$Y^{22}$— or —$Y^{21}$—S(=O)$_2$—O—$Y^{22}$—, $Y^{21}$ and $Y^{22}$ each independently represents a divalent hydrocarbon group which may have a substituent. Examples of the divalent hydrocarbon group include the same groups as those described above as the "divalent hydrocarbon group which may have a substituent" in the explanation of the aforementioned divalent linking group for $Ya^{21}$.

As $Y^{21}$, a linear aliphatic hydrocarbon group is preferable, more preferably a linear alkylene group, still more preferably a linear alkylene group of 1 to 5 carbon atoms, and a methylene group or an ethylene group is particularly desirable.

As $Y^{22}$, a linear or branched aliphatic hydrocarbon group is preferable, and a methylene group, an ethylene group or an alkylmethylene group is more preferable. The alkyl group within the alkylmethylene group is preferably a linear alkyl group of 1 to 5 carbon atoms, more preferably a linear alkyl group of 1 to 3 carbon atoms, and most preferably a methyl group.

In the group represented by the formula —[$Y^{21}$—C(=O)—O]$_{m''}$—$Y^{22}$—, m'' represents an integer of 0 to 3, preferably an integer of 0 to 2, more preferably 0 or 1, and most preferably 1. Namely, it is particularly desirable that the group represented by the formula —[$Y^{21}$—C(=O)—O]$_{m''}$—$Y^{22}$— is a group represented by the formula —$Y^{21}$—C(=O)—O—$Y^{22}$—. Among these, a group represented by the formula —(CH$_2$)$_{a'}$—C(=O)—O—(CH$_2$)$_{b'}$— is preferable. In the formula, a' is an integer of 1 to 10, preferably an integer of 1 to 8, more preferably an integer of 1 to 5, still more preferably 1 or 2, and most preferably 1. b' is an integer of 1 to 10, preferably an integer of 1 to 8, more preferably an integer of 1 to 5, still more preferably 1 or 2, and most preferably 1.

Among these examples, as $Ya^{21}$, a single bond, an ester bond [—C(=O)—O—], an ether bond (—O—), a linear or branched alkylene group, or a combination thereof is preferable.

In the formula (a2-1), $Ra^{21}$ represents a lactone-containing cyclic group, an —SO$_2$— containing cyclic group or a carbonate-containing cyclic group.

Preferable examples of the lactone-containing cyclic group, the —SO$_2$— containing cyclic group and the carbonate-containing cyclic group for $Ra^{21}$ include groups represented by general formulae (a2-r-1) to (a2-r-7), groups represented by general formulae (a5-r-1) to (a5-r-4) and groups represented by general formulae (ax3-r-1) to (ax3-r-3).

Among the above examples, a lactone-containing cyclic group or a —SO$_2$— containing cyclic group is preferable, and a group represented by general formula (a2-r-1), (a2-r-2), (a2-r-6) or (a5-r-1) is more preferable. Specifically, a group represented by any of chemical formulae (r-lc-1-1) to (r-lc-1-7), (r-lc-2-1) to (r-lc-2-18), (r-lc-6-1), (r-sl-1-1) and (r-sl-1-18) is still more preferable.

As the structural unit (a2) contained in the component (A1), 1 kind of structural unit may be used, or 2 or more kinds may be used.

When the component (A1) includes the structural unit (a2), the amount of the structural unit (a2) based on the combined total (100 mol %) of all structural units constituting the component (A1) is preferably 5 to 60 mol %, more preferably 10 to 60 mol %, and still more preferably 20 to 50 mol %.

When the amount of the structural unit (a2) is within the above-mentioned preferable range, solubility in a developing solution may be reliably assured, and the effects of the present invention may be more reliably achieved.

Structural Unit (a3):

The component (A1) may further include a structural unit (a3) containing a polar group-containing aliphatic hydrocarbon group. When the component (A1) includes the structural unit (a3), the hydrophilicity of the component (A1) is enhanced, thereby contributing to improvement in resolution. Further, the acid diffusion length may be appropriately adjusted.

Examples of the polar group include a hydroxyl group, cyano group, carboxyl group, or hydroxyalkyl group in which part of the hydrogen atoms of the alkyl group have been substituted with fluorine atoms, although a hydroxyl group is particularly desirable.

Examples of the aliphatic hydrocarbon group include linear or branched hydrocarbon groups (preferably alkylene groups) of 1 to 10 carbon atoms, and cyclic aliphatic hydrocarbon groups (cyclic groups). These cyclic groups can be selected appropriately from the multitude of groups that have been proposed for the resins of resist compositions designed for use with ArF excimer lasers.

In the case where the cyclic group is a monocyclic group, the monocyclic group preferably has 3 to 10 carbon atoms. Of the various possibilities, structural units derived from an acrylate ester that include an aliphatic monocyclic group that contains a hydroxyl group, cyano group, carboxyl group or a hydroxyalkyl group in which part of the hydrogen atoms of the alkyl group have been substituted with fluorine atoms are particularly desirable. Examples of the monocyclic groups include groups in which two or more hydrogen atoms have been removed from a monocycloalkane. Specific examples include groups in which two or more hydrogen atoms have been removed from a monocycloalkane such as cyclopentane, cyclohexane or cyclooctane. Of these polycyclic groups, groups in which two or more hydrogen atoms have been removed from cyclopentane or cyclohexane are preferred industrially.

In the case where the cyclic group is a polycyclic group, the polycyclic group preferably has 7 to 30 carbon atoms. Of the various possibilities, structural units derived from an acrylate ester that include an aliphatic polycyclic group that contains a hydroxyl group, cyano group, carboxyl group or a hydroxyalkyl group in which part of the hydrogen atoms of the alkyl group have been substituted with fluorine atoms are particularly desirable. Examples of the polycyclic group include groups in which two or more hydrogen atoms have been removed from a bicycloalkane, tricycloalkane, tetracycloalkane or the like. Specific examples include groups in which two or more hydrogen atoms have been removed from a polycycloalkane such as adamantane, norbornane, isobornane, tricyclodecane or tetracyclododecane. Of these polycyclic groups, groups in which two or more hydrogen atoms have been removed from adamantane, norbornane or tetracyclododecane are preferred industrially.

As the structural unit (a3), there is no particular limitation as long as it is a structural unit containing a polar group-containing aliphatic hydrocarbon group, and an arbitrary structural unit may be used.

The structural unit (a3) is preferably a structural unit derived from an acrylate ester which may have the hydrogen atom bonded to the carbon atom on the α-position substituted with a substituent and contains a polar group-containing aliphatic hydrocarbon group.

When the aliphatic hydrocarbon group within the polar group-containing aliphatic hydrocarbon group is a linear or branched hydrocarbon group of 1 to 10 carbon atoms, the structural unit (a3) is preferably a structural unit derived from a hydroxyethyl ester of acrylic acid.

On the other hand, in the structural unit (a3), when the hydrocarbon group within the polar group-containing aliphatic hydrocarbon group is a polycyclic group, structural units represented by formulas (a3-1), (a3-2), (a3-3) and (a3-4) shown below are preferable.

[Chemical Formula 42]

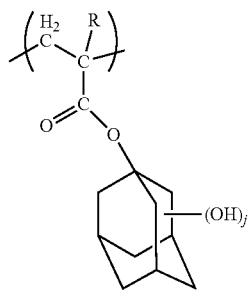
(a3-1)

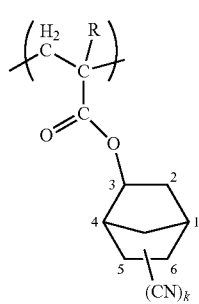
(a3-2)

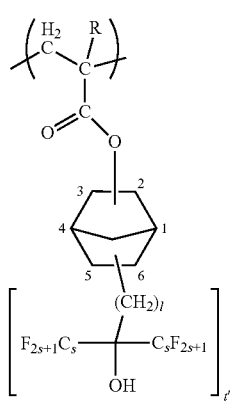
(a3-3)

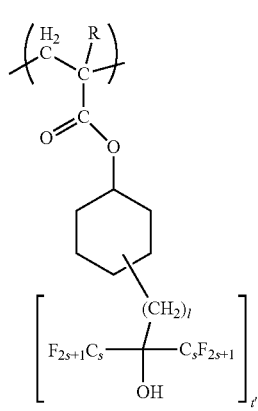
(a3-4)

In the formulas, R is the same as defined above; j is an integer of 1 to 3; k is an integer of 1 to 3; t' is an integer of 1 to 3; l is an integer of 0 to 5; and s is an integer of 1 to 3.

In formula (a3-1), j is preferably 1 or 2, and more preferably 1. When j is 2, it is preferable that the hydroxyl groups be bonded to the 3rd and 5th positions of the adamantyl group. When j is 1, it is preferable that the hydroxyl group be bonded to the 3rd position of the adamantyl group. j is preferably 1, and it is particularly desirable that the hydroxyl group be bonded to the 3rd position of the adamantyl group.

In formula (a3-2), k is preferably 1. The cyano group is preferably bonded to the 5th or 6th position of the norbornyl group.

In formula (a3-3), t' is preferably 1. l is preferably 1. s is preferably 1. Further, it is preferable that a 2-norbornyl group or 3-norbornyl group be bonded to the terminal of the carboxy group of the acrylic acid. The fluorinated alkyl alcohol is preferably bonded to the 5th or 6th position of the norbornyl group.

In formula (a3-4), t' is preferably 1 or 2. l is preferably 0 or 1. s is preferably 1. The fluorinated alkyl alcohol is preferably bonded to the 3rd or 5th position of the cyclohexyl group.

As the structural unit (a3) contained in the component (A1), 1 type of structural unit may be used, or 2 or more types may be used.

When the component (A1) includes the structural unit (a3), the amount of the structural unit (a3) based on the combined total (100 mol %) of all structural units constituting the component (A1) is preferably 1 to 30 mol %, more preferably 2 to 25 mol %, and still more preferably 5 to 20 mol %.

When the amount of the structural unit (a3) is at least as large as the lower limit of the above preferable range, the effect of using the structural unit (a3) may be satisfactorily achieved due to the aforementioned effects. On the other hand, when the amount of the structural unit (a3) is no more than the upper limit of the above preferable range, a good balance may be achieved with the other structural units, and various lithography properties may be improved.

Structural Unit (a4):

The component (A1) may further include a structural unit (a4) containing an acid non-dissociable, aliphatic cyclic group.

When the component (A1) includes the structural unit (a4), dry etching resistance of the resist pattern to be formed is improved. Further, the hydrophobicity of the component (A) is further improved. Increase in the hydrophobicity contributes to improvement in terms of resolution, shape of the resist pattern and the like, particularly in a solvent developing process. An "acid non-dissociable, aliphatic cyclic group" in the structural unit (a4) refers to a cyclic group which is not dissociated by the action of the acid (e.g., acid generated from a structural unit which generates acid upon exposure or acid generated from the component (B)) upon exposure, and remains in the structural unit.

As the structural unit (a4), a structural unit which contains a non-acid-dissociable aliphatic cyclic group, and is also derived from an acrylate ester is preferable. As the cyclic group, any of the multitude of conventional polycyclic groups used within the resin component of resist compositions for ArF excimer lasers or KrF excimer lasers (and particularly for ArF excimer lasers) can be used.

As the aliphatic polycyclic group, at least one polycyclic group selected from amongst a tricyclodecyl group, adamantyl group, tetracyclododecyl group, isobornyl group, and norbornyl group is particularly desirable in consideration of industrial availability and the like. These polycyclic groups may be substituted with a linear or branched alkyl group of 1 to 5 carbon atoms.

Specific examples of the structural unit (a4) include structural units represented by general formulae (a4-1) to (a4-7) shown below.

[Chemical Formula 43]

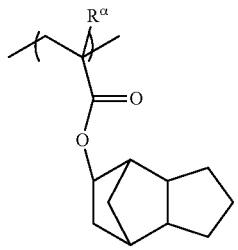

(a4-1)

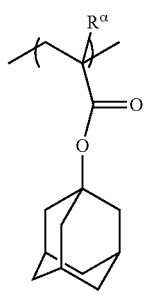

(a4-2)

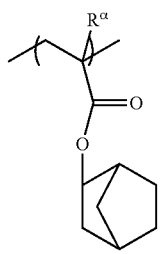

(a4-3)

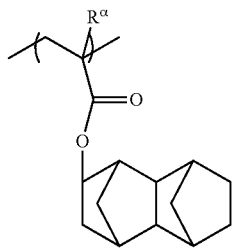

(a4-4)

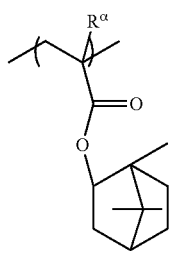

(a4-5)

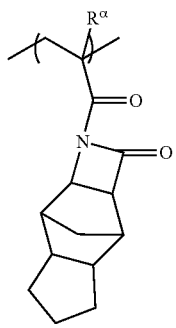
(a4-6)

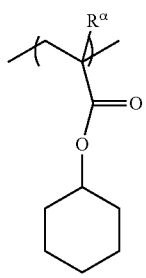
(a4-7)

In the formulae, $R^\alpha$ is the same as defined above.

As the structural unit (a4) contained in the component (A1), 1 type of structural unit may be used, or 2 or more types may be used.

When the component (A1) contains the structural unit (a4), the amount of the structural unit (a4) based on the combined total (100 mol %) of all structural units constituting the component (A) is preferably 1 to 40 mol %, and more preferably 5 to 20 mol %.

When the amount of the structural unit (a4) is at least as large as the lower limit of the above-mentioned preferable range, the effect of using the structural unit (a4) can be satisfactorily achieved. On the other hand, when the amount of the structural unit (a4) is no more than the upper limit of the above-mentioned preferable range, a good balance can be achieved with the other structural units.

—Structural Unit (St)

The structural unit (st) is a structural unit derived from styrene or a styrene derivative. A "structural unit derived from styrene" refers to a structural unit that is formed by the cleavage of the ethylenic double bond of styrene. A "structural unit derived from a styrene derivative" refers to a structural unit that is formed by the cleavage of the ethylenic double bond of a styrene derivative (provided that structural units which fall under the definition of the structural unit (a10) is excluded).

A "styrene derivative" refers to a compound in which at least part of the hydrogen atoms of styrene has been substituted with a substituent. Examples of the styrene derivative include a compound in which the hydrogen at the α-position of styrene has been substituted with a substituent, a compound in which at least one hydrogen atom on the benzene ring of styrene has been substituted with a substituent, and a compound in which the hydrogen at the α-position of styrene and at least one hydrogen atom on the benzene ring of styrene has been substituted with a substituent.

Examples of the substituent which substitutes the hydrogen atom at the α-position of styrene include an alkyl group having 1 to 5 carbon atoms, and a halogenated alkyl group having 1 to 5 carbon atoms.

The alkyl group of 1 to 5 carbon atoms is preferably a linear or branched alkyl group of 1 to 5 carbon atoms, and specific examples include a methyl group, an ethyl group, a propyl group, an isopropyl group, an n-butyl group, an isobutyl group, a tert-butyl group, a pentyl group, an isopentyl group, and a neopentyl group.

The halogenated alkyl group of 1 to 5 carbon atoms is a group in which part or all of the hydrogen atoms of the aforementioned alkyl group of 1 to 5 carbon atoms have been substituted with halogen atom(s). As the halogen atom, a fluorine atom is most preferable.

As the substituent which substitutes the hydrogen atom at the α-position of styrene, an alkyl group having 1 to 5 carbon atoms or a fluorinated alkyl group having 1 to 5 carbon atoms is preferable, an alkyl group having 1 to 3 carbon atoms or a fluorinated alkyl group having 1 to 3 carbon atoms is more preferable, and in terms of industrial availability, a methyl group is more preferable.

Examples of the substituent which substitutes a hydrogen atom on the benzene ring of styrene include an alkyl group, an alkoxy group, a halogen atom, and a halogenated alkyl group.

The alkyl group as the substituent is preferably an alkyl group of 1 to 5 carbon atoms, and more preferably a methyl group, an ethyl group, a propyl group, an n-butyl group or a tert-butyl group.

The alkoxy group as the substituent is preferably an alkoxy group having 1 to 5 carbon atoms, more preferably a methoxy group, ethoxy group, n-propoxy group, isopropoxy group, n-butoxy group or tert-butoxy group, and still more preferably a methoxy group or an ethoxy group.

The halogen atom as the substituent is preferably a fluorine atom.

Examples of the halogenated alkyl group for the substituent include groups in which part or all of the hydrogen atoms within the aforementioned alkyl groups has been substituted with the aforementioned halogen atoms.

As the substituent which substitutes a hydrogen atom on the benzene ring of styrene, an alkyl group having 1 to 5 carbon atoms is preferable, a methyl group or an ethyl group is more preferable, and a methyl group is still more preferable.

As the structural unit (st), a structural unit derived from styrene or a structural unit derived from a styrene derivative in which the hydrogen atom at the α-position of styrene has been substituted with an alkyl group having 1 to 5 carbon atoms or a halogenated alkyl group having 1 to 5 carbon atoms is preferable, a structural unit derived from styrene or a structural unit derived from a styrene derivative in which the hydrogen atom at the α>-position of styrene has been substituted with a methyl group is more preferable, and a structural unit derived from styrene is still more preferable.

As the structural unit (st) contained in the component (A1), 1 kind of structural unit may be used, or 2 or more kinds of structural units may be used.

When the component (A1) includes the structural unit (st), the amount of the structural unit (st) based on the combined total of all structural units constituting the component (A1) (100 mol %) is preferably 1 to 30 mol %, and more preferably 3 to 20 mol %.

In the resist composition, as the component (A), one kind of compound may be used, or two or more kinds of compounds may be used in combination.

In the resist composition of the present embodiment, examples of the component (A1) include a polymeric compound (A10) having a repeating structure of the structural unit (a0).

Preferable examples of the component (A1) include a polymeric compound (A11) having a repeating structure of the structural units (a0) and (a10); and a polymeric compound (A12) having a repeating structure of the structural units (a0), (a2) and (a3).

In the polymeric compound (A10), the polymeric compound (A11) and the polymeric compound (A12), the amount of the structural unit (a0) based on the combined total (100 mol %) of all the structural units that constitute the polymeric compound (A10), the polymeric compound (A11) and the polymeric compound (A12) is preferably 40 to 70 mol %, and more preferably 45 to 65 mol %.

When the amount of the structural unit (a0) is within the above-mentioned preferable range, efficiency of the deprotection reaction and solubility in a developing solution may be reliably assured, and the effects of the present invention may be more reliably achieved.

The component (A1) may be produced, for example, by dissolving the monomers corresponding with each of the structural units in a polymerization solvent, followed by addition of a radical polymerization initiator such as azobisisobutyronitrile (AIBN) or dimethyl-2,2'-azobisisoutyrate (e.g., V-601).

Alternatively, the component (A1) may be prepared by dissolving a monomer from which the structural unit (a0) is derived, and a monomer from which the structural unit other than the structural unit (a0) is derived in a polymerization solvent, polymerizing the dissolved monomers using the radical polymerization initiator described above, followed by performing a deprotection reaction.

In the polymerization, a chain transfer agent such as HS—$CH_2$—$CH_2$—$CH_2$—$C(CF_3)_2$—OH may be used to introduce a —$C(CF_3)_2$—OH group at the terminal(s) of the polymer. Such a copolymer having introduced a hydroxyalkyl group in which some of the hydrogen atoms of the alkyl group are substituted with fluorine atoms is effective in reducing developing defects and LER (line edge roughness: unevenness of the side walls of a line pattern).

The weight average molecular weight (Mw) (the polystyrene equivalent value determined by gel permeation chromatography (GPC)) of the component (A1) is not particularly limited, but is preferably 1,000 to 50,000, more preferably 2,000 to 30,000, and still more preferably 3,000 to 20,000.

When the Mw of the component (A1) is no more than the upper limit of the above-mentioned preferable range, the resist composition exhibits a satisfactory solubility in a resist solvent. On the other hand, when the Mw of the component (A1) is at least as large as the lower limit of the above-mentioned preferable range, dry etching resistance and the cross-sectional shape of the resist pattern becomes satisfactory.

The dispersity (Mw/Mn) of the component (A1) is not particularly limited, but is preferably 1.0 to 4.0, more preferably 1.0 to 3.0, and most preferably 1.0 to 2.0. Here, Mn is the number average molecular weight.

—Component (A2)

In the resist composition of the present embodiment, as the component (A), "a base component which exhibits changed solubility in a developing solution under action of acid" other than the component (A1) (hereafter, referred to as "component (A2)") may be used in combination.

As the component (A2), there is no particular limitation, and any of the multitude of conventional base resins used within chemically amplified resist compositions may be arbitrarily selected for use.

As the component (A2), one kind of a polymer or a low molecular weight compound may be used, or a combination of two or more kinds may be used.

In the component (A), the amount of the component (A1) based on the total weight of the component (A) is preferably 25% by weight or more, more preferably 50% by weight or more, still more preferably 75% by weight or more, and may be even 100% by weight. When the amount of the component (A1) is 25% by weight or more, a resist pattern with improved lithography properties such as improvement in roughness may be reliably formed.

In the resist composition of the present embodiment, the amount of the component (A) may be appropriately adjusted depending on the thickness of the resist film to be formed, and the like.

<Compound (D0)>

In the resist composition of the present embodiment, the component (D0) is a compound represented by general formula (d0) shown below having an anion moiety and a cation moiety. In the resist composition of the present embodiment, the component (D0) is used as a basic component which suppresses diffusion of acid generated upon exposure.

[Chemical Formula 44]

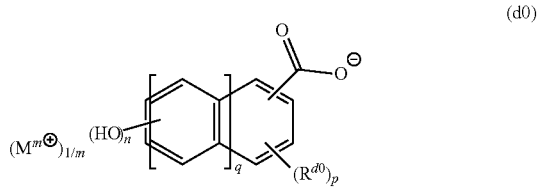

In the formula, $M^{m+}$ represents an m-valent organic cation; m represents an integer of 1 or more. $R^{d0}$ represents a substituent; p represents an integer of 0 to 2; when p is 2, the plurality of $R^{d0}$ may be the same or different from each other; q represents an integer of 0 to 3; n represents an integer of 2 or more; provided that n+p≤(q×2)+5.

{Anion Moiety}

In formula (d0), $R^{d0}$ represents a substituent. Examples of the substituent include a hydrocarbon group, an alkoxy group, an acyl group, and a hydroxyalkyl group.

Examples of the hydrocarbon group as the substituent include a linear or branched alkyl group, an aliphatic cyclic hydrocarbon group, and an aromatic hydrocarbon group.

As the linear or branched alkyl group, a linear or branched alkyl group of 1 to 5 carbon atoms is preferable, and specific examples thereof include a methyl group, an ethyl group, a propyl group, an n-butyl group, a tert-butyl group and a pentyl group.

As the aliphatic cyclic hydrocarbon group, an aliphatic cyclic hydrocarbon group having 3 to 6 carbon atoms is preferable, and specific examples thereof include a cyclopropyl group, a cyclobutyl group, a cyclopentyl group, and a cyclohexyl group.

As the aromatic hydrocarbon group, an aromatic hydrocarbon group having 6 to 30 carbon atoms is preferable, and specific examples thereof include a group in which 1 hydrogen atom has been removed from an aromatic hydrocarbon ring such as benzene, biphenyl, fluorene, naphthalene, anthracene or phenanthrene. Among these examples, a group in which 1 hydrogen atom has been removed from benzene (phenyl group) is preferable.

The alkoxy group as the substituent is preferably an alkoxy group having 1 to 5 carbon atoms, and specific examples thereof include a methoxy group, an ethoxy group, a propoxy group, an n-butoxy group, a tert-butoxy group, and a pentyloxy group. Among these examples, a methoxy group is preferable.

The acyl group as the substituent is preferably an acyl group having 1 to 3 carbon atoms, and specific examples thereof include a formyl group, an acetyl group, and a propionyl group.

The hydroxyalkyl group as the substituent is preferably a hydroxyalkyl group having 1 to 5 carbon atoms, and specific examples thereof include a hydroxymethyl group, a hydroxyethyl group, a hydroxypropyl group, a hydroxybutyl group, and a hydroxypentyl group.

In formula (d0), p represents an integer of 0 to 2. When p is 2, the plurality of $R^{d0}$ may be the same or different from each other.

In formula (d0), q represents an integer of 0 to 3. That is, the anion moiety of formula (d0), when q is 0, becomes a benzene structure; when q is 1, becomes a naphthalene structure; when q is 2, becomes an anthracene structure; and when q is 3, becomes a tetracene structure.

Further, $n+p \leq (q \times 2)+5$. That is, in the above benzene structure, naphthalene structure, anthracene structure or tetracene structure, all hydrogen atoms other than the hydrogen atom substituted with a carboxylate group may be substituted with the aforementioned substituent or a hydroxy group. However, the anion moiety of formula (d0) has at least 2 hydroxy groups.

Specific examples of preferable anion moieties for the component (D0) are shown below.

[Chemical Formula 45]

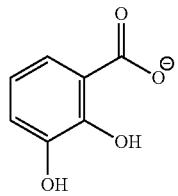
(an-d0-1)

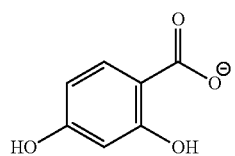
(an-d0-2)

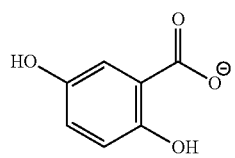
(an-d0-3)

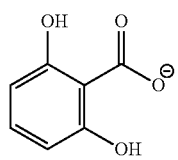
(an-d0-4)

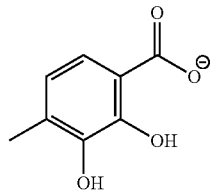
(an-d0-5)

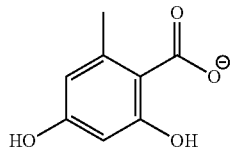
(an-d0-6)

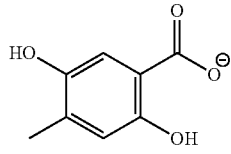
(an-d0-7)

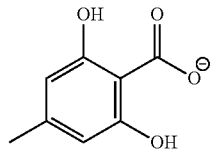
(an-d0-8)

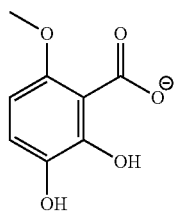
(an-d0-9)

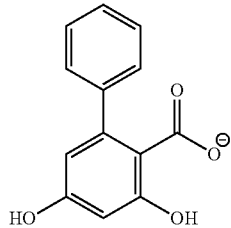
(an-d0-10)

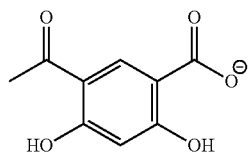
(an-d0-11)

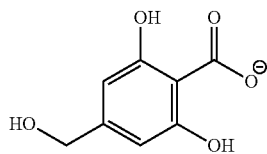
(an-d0-12)

[Chemical Formula 46]
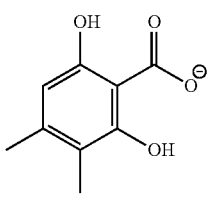 (an-d0-13)
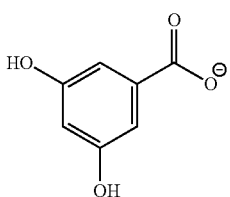 (an-d0-14)
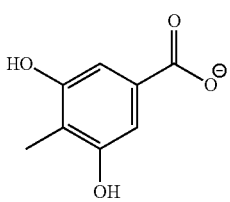 (an-d0-15)
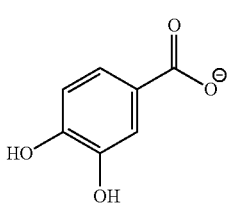 (an-d0-16)
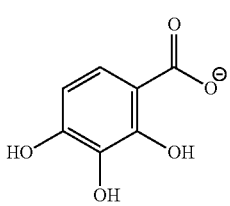 (an-d0-17)
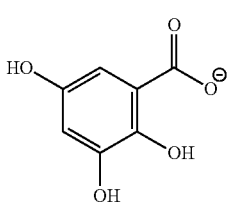 (an-d0-18)
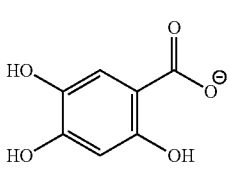 (an-d0-19)
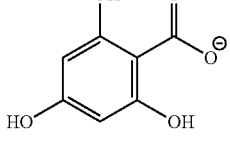 (an-d0-20)
[Chemical Formula 47]
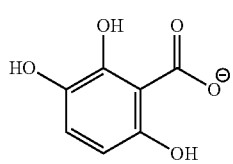 (an-d0-21)
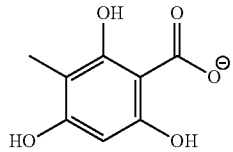 (an-d0-22)
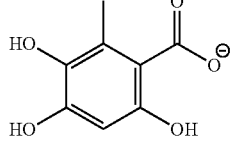 (an-d0-23)
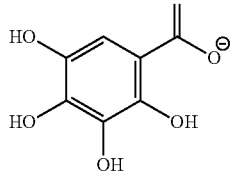 (an-d0-24)
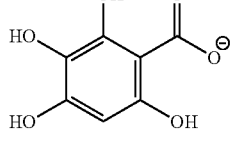 (an-d0-25)
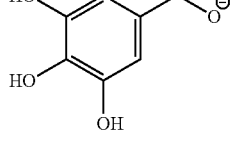 (an-d0-26)
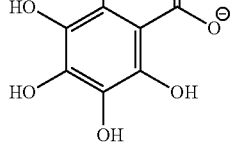 (an-d0-27)
[Chemical Formula 48]
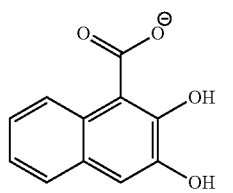 (an-d0-28)

(an-d0-29)
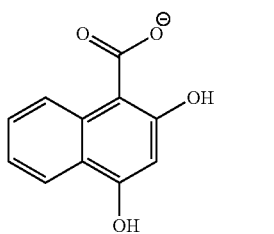
(an-d0-30)
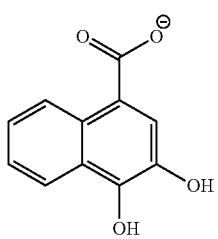
(an-d0-31)
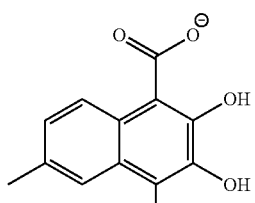
(an-d0-32)
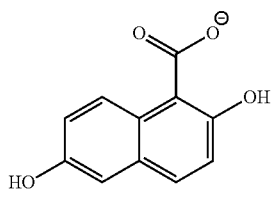
(an-d0-33)
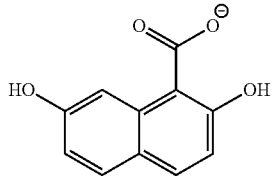
(an-d0-34)
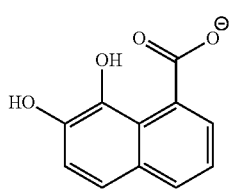
(an-d0-35)
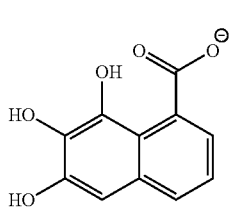
(an-d0-36)
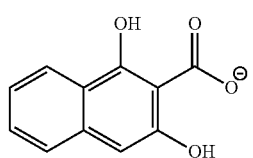
(an-d0-37)
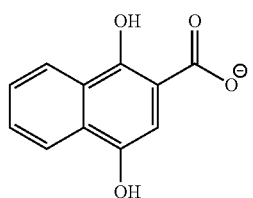
(an-d0-38)
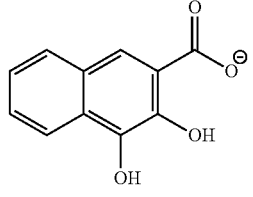
[Chemical Formula 49]
(an-d0-39)
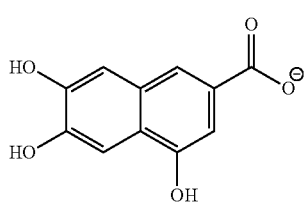
(an-d0-40)
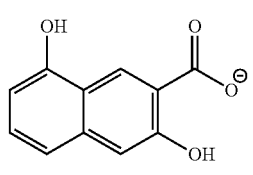
(an-d0-41)
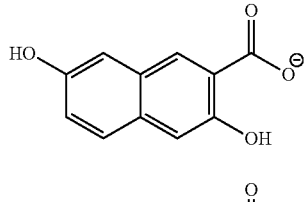
(an-d0-42)
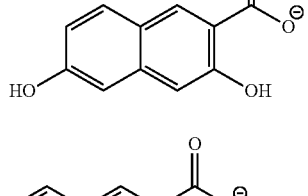
(an-d0-43)
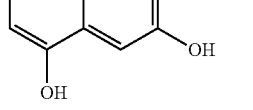

-continued

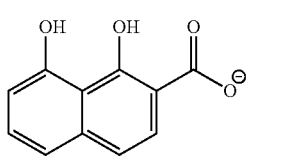
(an-d0-44)

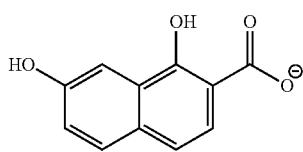
(an-d0-45)

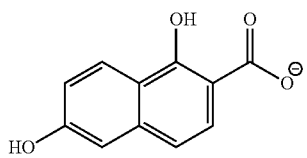
(an-d0-46)

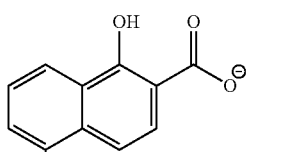
(an-d0-47)

[Chemical Formula 50]

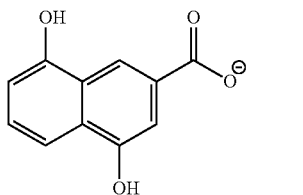
(an-d0-48)

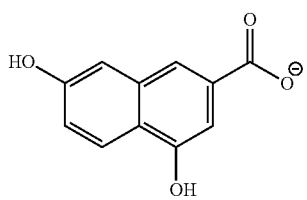
(an-d0-49)

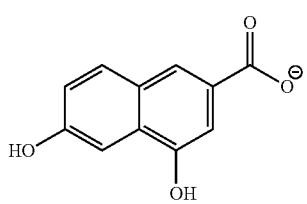
(an-d0-50)

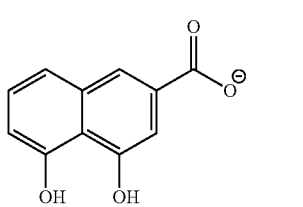
(an-d0-51)

{Cation Moiety}

In general formula (d0), $M^{m+}$ represents an m-valent onium cation. Among these, a sulfonium cation or a iodonium cation is preferable.

m represents an integer of 1 or more.

As preferable examples of the cation moiety $((M^{m+})_{1/m})$, organic cations represented by general formulae (ca-1) to (ca-5) shown below may be given.

[Chemical Formula 51]

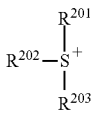
(ca-1)

(ca-2)

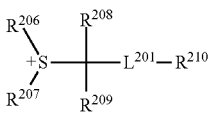
(ca-3)

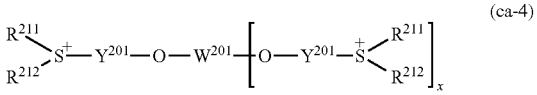
(ca-4)

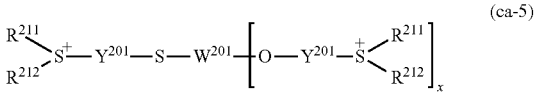
(ca-5)

In the formulae, $R^{201}$ to $R^{207}$, $R^{211}$ and $R^{212}$ each independently represents an aryl group which may have a substituent, an alkyl group which may have a substituent, or an alkenyl group which may have a substituent. $R^{201}$ to $R^{203}$, $R^{206}$ and $R^{207}$, and $R^{211}$ and $R^{212}$ may be mutually bonded to form a ring with the sulfur atom. $R^{208}$ and $R^{209}$ each independently represents a hydrogen atom or an alkyl group of 1 to 5 carbon atoms. $R^{210}$ represents an aryl group which may have a substituent, an alkyl group which may have a substituent, an alkenyl group which may have a substituent, or an —$SO_2$— containing cyclic group which may have a substituent. $L^{201}$ represents —C(=O)— or —C(=O)—O—. Each $Y^{201}$ independently represents an arylene group, an alkylene group or an alkenylene group. x represents 1 or 2. $W^{201}$ represents an (x+1) valent linking group.

In formulae (ca-1) to (ca-5), as the aryl group for $R^{201}$ to $R^{207}$, $R^{211}$ and $R^{212}$, an unsubstituted aryl group of 6 to 20 carbon atoms can be mentioned, and a phenyl group or a naphthyl group is preferable.

The alkyl group for $R^{201}$ to $R^{207}$, $R^{211}$ and $R^{212}$ is preferably a chain-like or cyclic alkyl group having 1 to 30 carbon atoms.

The alkenyl group for $R^{201}$ to $R^{207}$, $R^{211}$ and $R^{212}$ preferably has 2 to 10 carbon atoms.

Specific examples of the substituent which $R^{201}$ to $R^{207}$ and $R^{210}$ to $R^{212}$ may have include an alkyl group, a halogen atom, a halogenated alkyl group, a carbonyl group, a cyano group, an amino group, an aryl group, and groups represented by general formulae (ca-r-1) to (ca-r-7) shown below.

[Chemical Formula 52]

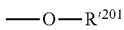
[ca-r-1]

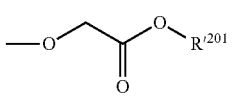
[ca-r-2]

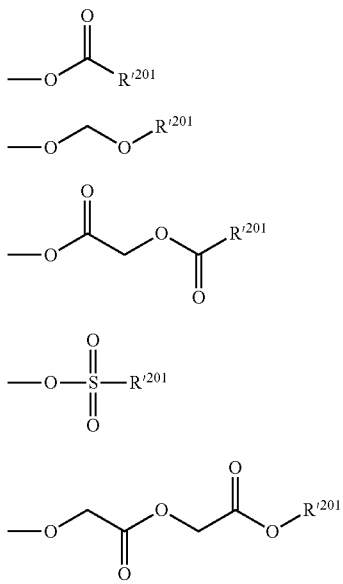

In the formulae, each $R'^{201}$ independently represents a hydrogen atom, a cyclic group which may have a substituent, a chain-like alkyl group which may have a substituent, or a chain-like alkenyl group which may have a substituent.

Cyclic Group which May have a Substituent:

The cyclic group is preferably a cyclic hydrocarbon group, and the cyclic hydrocarbon group may be either an aromatic hydrocarbon group or an aliphatic hydrocarbon group. An "aliphatic hydrocarbon group" refers to a hydrocarbon group that has no aromaticity. The aliphatic hydrocarbon group may be either saturated or unsaturated, but in general, the aliphatic hydrocarbon group is preferably saturated.

The aromatic hydrocarbon group for $R'^{201}$ is a hydrocarbon group having an aromatic ring. The aromatic hydrocarbon group preferably has 3 to 30 carbon atoms, more preferably 5 to 30 carbon atoms, still more preferably 5 to 20 carbon atoms, still more preferably 6 to 15 carbon atoms, and most preferably 6 to 10 carbon atoms. Here, the number of carbon atoms within a substituent(s) is not included in the number of carbon atoms of the aromatic hydrocarbon group.

Examples of the aromatic ring contained in the aromatic hydrocarbon group for $R'^{201}$ include benzene, fluorene, naphthalene, anthracene, phenanthrene, biphenyl, or an aromatic hetero ring in which part of the carbon atoms constituting the aromatic ring has been substituted with a hetero atom. Examples of the hetero atom within the aromatic hetero rings include an oxygen atom, a sulfur atom and a nitrogen atom.

Specific examples of the aromatic hydrocarbon group for $R'^{201}$ include a group in which 1 hydrogen atom has been removed from the aforementioned aromatic ring (an aryl group, such as a phenyl group or a naphthyl group), and a group in which 1 hydrogen atom of the aforementioned aromatic ring has been substituted with an alkylene group (an arylalkyl group, such as a benzyl group, a phenethyl group, a 1-naphthylmethyl group, a 2-naphthylmethyl group, a 1-naphthylethyl group, or a 2-naphthylethyl group). The alkylene group (alkyl chain within the arylalkyl group) preferably has 1 to 4 carbon atom, more preferably 1 or 2, and most preferably 1.

Examples of the cyclic aliphatic hydrocarbon group for $R'^{201}$ include aliphatic hydrocarbon groups containing a ring in the structure thereof.

As examples of the hydrocarbon group containing a ring in the structure thereof, an alicyclic hydrocarbon group (a group in which one hydrogen atom has been removed from an aliphatic hydrocarbon ring), a group in which the alicyclic hydrocarbon group is bonded to the terminal of the aforementioned chain-like aliphatic hydrocarbon group, and a group in which the alicyclic group is interposed within the aforementioned linear or branched aliphatic hydrocarbon group, can be given.

The alicyclic hydrocarbon group preferably has 3 to 20 carbon atoms, and more preferably 3 to 12 carbon atoms.

The alicyclic hydrocarbon group may be either a polycyclic group or a monocyclic group. As the monocyclic alicyclic hydrocarbon group, a group in which one or more hydrogen atoms have been removed from a monocycloalkane is preferable. The monocycloalkane preferably has 3 to 6 carbon atoms, and specific examples thereof include cyclopentane and cyclohexane. As the polycyclic alicyclic hydrocarbon group, a group in which one or more hydrogen atoms have been removed from a polycycloalkane is preferable, and the polycyclic group preferably has 7 to 30 carbon atoms. Among polycycloalkanes, a polycycloalkane having a bridged ring polycyclic skeleton, such as adamantane, norbornane, isobornane, tricyclodecane or tetracyclododecane, and a polycycloalkane having a condensed ring polycyclic skeleton, such as a cyclic group having a steroid skeleton are preferable.

Among these examples, as the cyclic aliphatic hydrocarbon group for $R'^{201}$, a group in which one or more hydrogen atoms have been removed from a monocycloalkane or a polycycloalkane is preferable, a group in which one or more hydrogen atoms have been removed from a polycycloalkane is more preferable, an adamantyl group or a norbornyl group is still more preferable, and an adamantyl group is most preferable.

The linear or branched aliphatic hydrocarbon group which may be bonded to the alicyclic hydrocarbon group preferably has 1 to 10 carbon atoms, more preferably 1 to 6 carbon atoms, still more preferably 1 to 4 carbon atoms, and most preferably 1 to 3 carbon atoms.

As the linear aliphatic hydrocarbon group, a linear alkylene group is preferable. Specific examples thereof include a methylene group [—$CH_2$—], an ethylene group [—$(CH_2)_2$—], a trimethylene group [—$(CH_2)_3$—], a tetramethylene group [—$(CH_2)_4$—] and a pentamethylene group [—$(CH_2)_5$—].

As the branched aliphatic hydrocarbon group, branched alkylene groups are preferred, and specific examples include various alkylalkylene groups, including alkylmethylene groups such as —$CH(CH_3)$—, —$CH(CH_2CH_3)$—, —$C(CH_3)_2$—, —$C(CH_3)(CH_2CH_3)$—, —$C(CH_3)(CH_2CH_2CH_3)$—, and —$C(CH_2CH_3)_2$—; alkylethylene groups such as —$CH(CH_3)CH_2$—, —$CH(CH_3)CH(CH_3)$—, —$C(CH_3)_2CH_2$—, —$CH(CH_2CH_3)CH_2$—, and —$C(CH_2CH_3)_2$—$CH_2$—; alkyltrimethylene groups such as —$CH(CH_3)CH_2CH_2$—, and —$CH_2CH(CH_3)CH_2$—; and alkyltetramethylene groups such as —$CH(CH_3)CH_2CH_2CH_2$—, and —$CH_2CH(CH_3)CH_2CH_2$—. As the alkyl group within the alkylalkylene group, a linear alkyl group of 1 to 5 carbon atoms is preferable.

The cyclic hydrocarbon group for $R'^{201}$ may contain a hetero atom such as a heterocycle. Specific examples include lactone-containing cyclic groups represented by the aforementioned general formulae (a2-r-1) to (a2-r-7), the —$SO_2$— containing cyclic group represented by the aforementioned formulae (a5-r-1) to (a5-r-4), and other heterocyclic groups represented by the aforementioned chemical formulae (r-hr-1) to (r-hr-16).

As the substituent for the cyclic group for $R'^{201}$, an alkyl group, an alkoxy group, a halogen atom, a halogenated alkyl group, a hydroxyl group, a carbonyl group, a nitro group or the like can be used.

The alkyl group as the substituent is preferably an alkyl group of 1 to 5 carbon atoms, and a methyl group, an ethyl group, a propyl group, an n-butyl group or a tert-butyl group is particularly desirable.

The alkoxy group as the substituent is preferably an alkoxy group having 1 to 5 carbon atoms, more preferably a methoxy group, ethoxy group, n-propoxy group, iso-propoxy group, n-butoxy group or tert-butoxy group, and most preferably a methoxy group or an ethoxy group.

The halogen atom as the substituent is preferably a fluorine atom.

Example of the aforementioned halogenated alkyl group includes a group in which a part or all of the hydrogen atoms within an alkyl group of 1 to 5 carbon atoms (e.g., a methyl group, an ethyl group, a propyl group, an n-butyl group or a tert-butyl group) have been substituted with the aforementioned halogen atoms.

The carbonyl group as the substituent is a group that substitutes a methylene group (—$CH_2$—) constituting the cyclic hydrocarbon group.

Chain Alkyl Group which May have a Substituent:

The chain alkyl group for $R'^{201}$ may be linear or branched.

The linear alkyl group preferably has 1 to 20 carbon atoms, more preferably 1 to 15 carbon atoms, and still more preferably 1 to 10 carbon atoms.

The branched alkyl group preferably has 3 to 20 carbon atoms, more preferably 3 to 15 carbon atoms, and still more preferably 3 to 10 carbon atoms. Specific examples include a 1-methylethyl group, a 1-methylpropyl group, a 2-methylpropyl group, a 1-methylbutyl group, a 2-methylbutyl group, a 3-methylbutyl group, a 1-ethylbutyl group, a 2-ethylbutyl group, a 1-methylpentyl group, a 2-methylpentyl group, a 3-methylpentyl group and a 4-methylpentyl group.

Chain Alkenyl Group which May have a Substituent:

The chain alkenyl group for $R'^{201}$ may be linear or branched, and preferably has 2 to 10 carbon atoms, more preferably 2 to 5 carbon atoms, still more preferably 2 to 4 carbon atoms, and most preferably 3 carbon atoms. Examples of linear alkenyl groups include a vinyl group, a propenyl group (an allyl group) and a butynyl group. Examples of branched alkenyl groups include a 1-methylvinyl group, a 2-methylvinyl group, a 1-methylpropenyl group and a 2-methylpropenyl group.

Among these examples, as the chain-like alkenyl group, a linear alkenyl group is preferable, a vinyl group or a propenyl group is more preferable, and a vinyl group is most preferable.

As the substituent for the chain-like alkyl group or alkenyl group for $R'^{201}$, an alkoxy group, a halogen atom, a halogenated alkyl group, a hydroxyl group, a carbonyl group, a nitro group, an amino group, a cyclic group for $R'^{201}$ or the like may be used.

As the cyclic group which may have a substituent, the chain alkyl group which may have a substituent and the chain alkenyl group which may have a substituent for $R'^{201}$, the same groups as those described above may be mentioned. As the cyclic group which may have a substituent and chain alkyl group which may have a substituent, the same groups as those described above for the acid dissociable group represented by the aforementioned formula (a1-r-2) may be also mentioned.

Among these examples, as $R'^{201}$, a cyclic group which may have a substituent is preferable, and a cyclic hydrocarbon group which may have a substituent is more preferable. Specifically, for example, a phenyl group, a naphthyl group, a group in which one or more hydrogen atoms have been removed from a polycycloalkane, a lactone-containing cyclic group represented by any one of the aforementioned formula (a2-r-1) to (a2-r-7), and an —$SO_2$— containing cyclic group represented by any one of the aforementioned formula (a5-r-1) to (a5-r-4) are preferable.

In formulae (ca-1) to (ca-5), in the case where $R^{201}$ to $R^{203}$, $R^{206}$ and $R^{207}$, or $R^{21}$ and $R^{212}$ are mutually bonded to form a ring with the sulfur atom, these groups may be mutually bonded via a hetero atom such as a sulfur atom, an oxygen atom or a nitrogen atom, or a functional group such as a carbonyl group, —SO—, —$SO_2$—, —$SO_3$—, —COO—, —CONH— or —N($R_N$)— ($R_N$ represents an alkyl group of 1 to 5 carbon atoms). The ring containing the sulfur atom in the skeleton thereof is preferably a 3 to 10-membered ring, and most preferably a 5 to 7-membered ring. Specific examples of the ring formed include a thiophene ring, a thiazole ring, a benzothiophene ring, a dibenzothiophene ring, a 9H-thioxanthene ring, a thioxanthene ring, a thianthrene ring, a phenoxathiin ring, a tetrahydrothiophenium ring, and a tetrahydrothiopyranium ring.

$R^{208}$ and $R^{209}$ each independently represents a hydrogen atom or an alkyl group of 1 to 5 carbon atoms, preferably a hydrogen atom or an alkyl group of 1 to 3 carbon atoms, and when $R^{208}$ and $R^{209}$ each represents an alkyl group, $R^{208}$ and $R^{209}$ may be mutually bonded to form a ring.

$R^{210}$ represents an aryl group which may have a substituent, an alkyl group which may have a substituent, an alkenyl group which may have a substituent, or an 502-containing cyclic group which may have a substituent.

Examples of the aryl group for $R^{210}$ include an unsubstituted aryl group of 6 to 20 carbon atoms, and a phenyl group or a naphthyl group is preferable.

As the alkyl group for $R^{210}$, a chain-like or cyclic alkyl group having 1 to 30 carbon atoms is preferable.

The alkenyl group for $R^{210}$ preferably has 2 to 10 carbon atoms. As the —$SO_2$-containing cyclic group for $R^{210}$ which may have a substituent, an "—$SO_2$-containing polycyclic group" is preferable, and a group represented by the aforementioned general formula (a5-r-1) is more preferable.

Each $Y^{201}$ independently represents an arylene group, an alkylene group or an alkenylene group.

Examples of the arylene group for $Y^{201}$ include groups in which one hydrogen atom has been removed from an aryl group given as an example of the aromatic hydrocarbon group for the aforementioned $Ya^{x0}$.

Examples of the alkylene group and alkenylene group for $Y^{201}$ include groups in which one hydrogen atom has been removed from the chain alkyl group or the chain alkenyl group given as an example of $R'^{201}$.

In the formula (ca-4), x represents 1 or 2.

$W^{201}$ represents a linking group having a valency of (x+1), i.e., a divalent or trivalent linking group.

As the divalent linking group for $W^{201}$, a divalent hydrocarbon group which may have a substituent is preferable, and as examples thereof, the same hydrocarbon groups (which may have a substituent) as those described above for $Ya^{21}$ in the general formula (a2-1) can be mentioned. The divalent linking group for $W^{201}$ may be linear, branched or cyclic, and cyclic is more preferable. Among these, an arylene group having two carbonyl groups, each bonded to the terminal thereof is preferable. Examples of the arylene group include a phenylene group and a naphthylene group, and a phenylene group is particularly desirable.

As the trivalent linking group for $W^{201}$, a group in which one hydrogen atom has been removed from the aforementioned divalent linking group for $W^{201}$ and a group in which the divalent linking group has been bonded to another divalent linking group can be mentioned. The trivalent linking group for $W^{201}$ is preferably a group in which 2 carbonyl groups are bonded to an arylene group.

Specific examples of preferable cations represented by formula (ca-1) are shown below.

[Chemical Formula 53]

(ca-1-1)

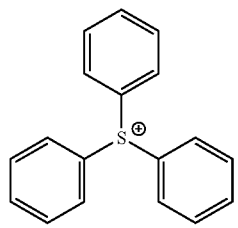

(ca-1-2)

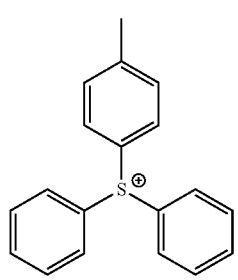

(ca-1-3)

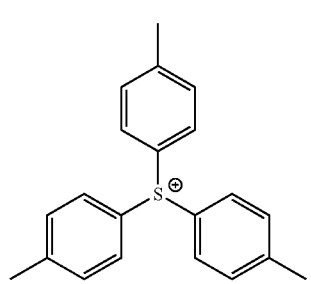

(ca-1-4)

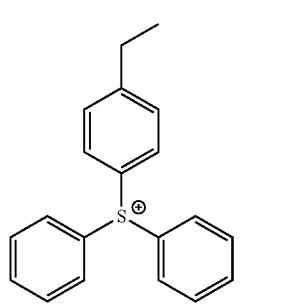

(ca-1-5)

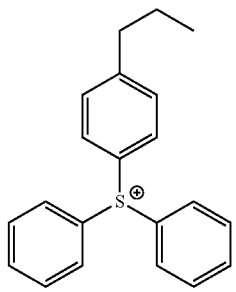

(ca-1-6)

(ca-1-7)

(ca-1-8)

(ca-1-9)

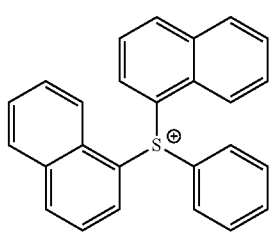

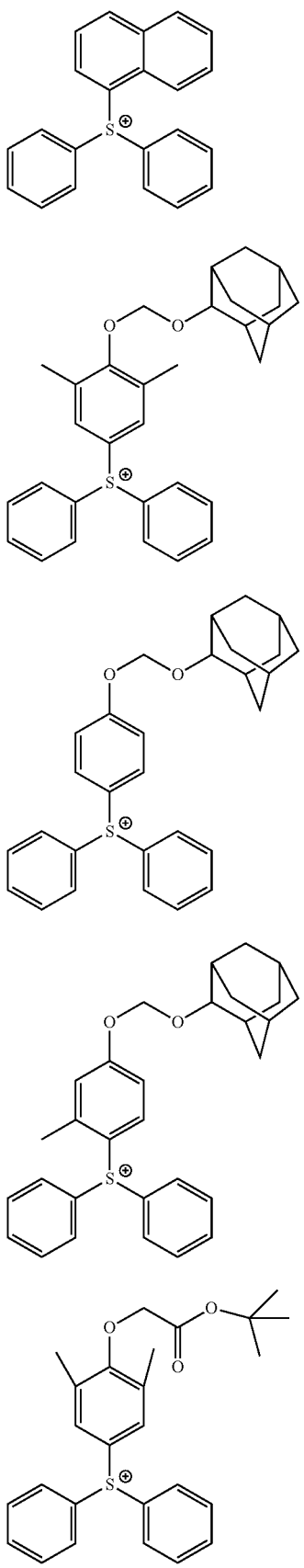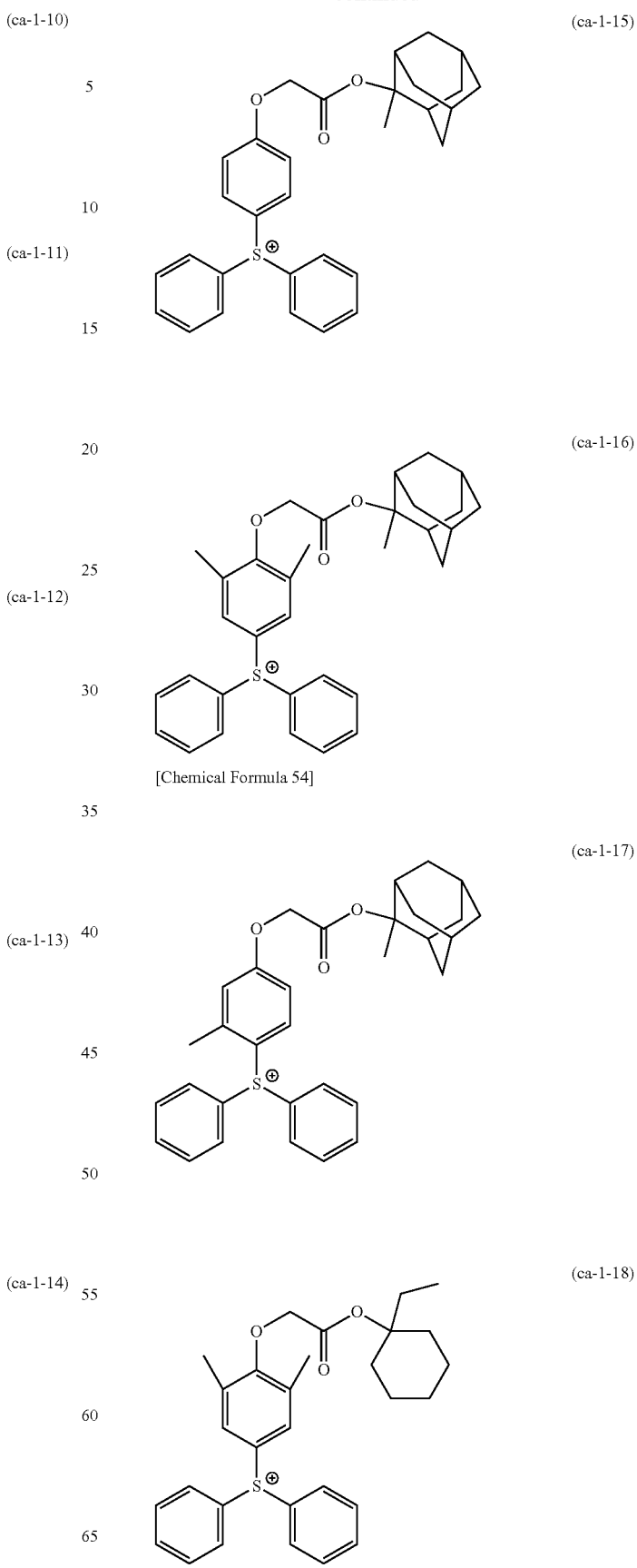

(ca-1-19)
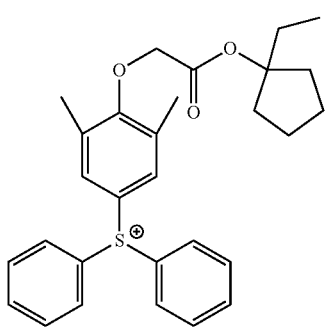
(ca-1-20)
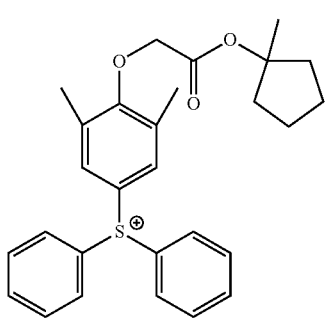
(ca-1-21)
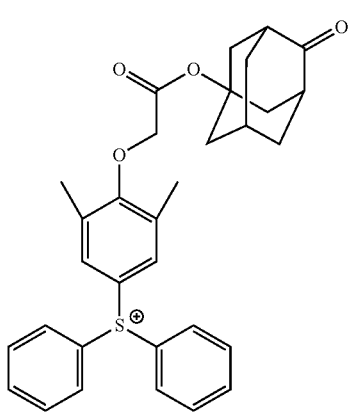
(ca-1-22)
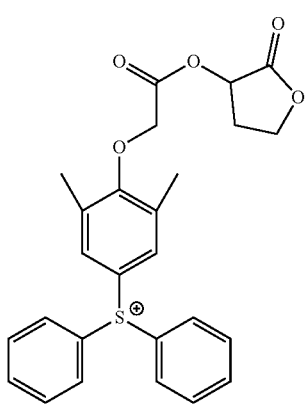
(ca-1-23)
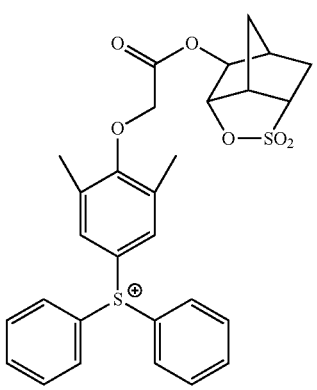
(ca-1-24)
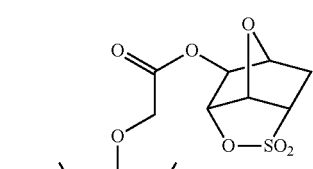
(ca-1-25)
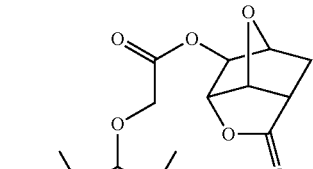
(ca-1-26)
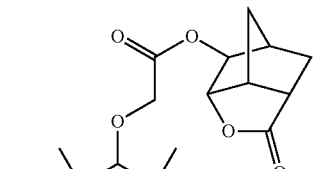

(ca-1-27)
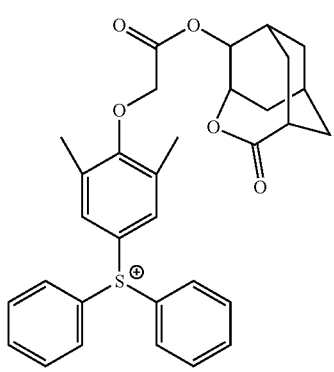
(ca-1-32)
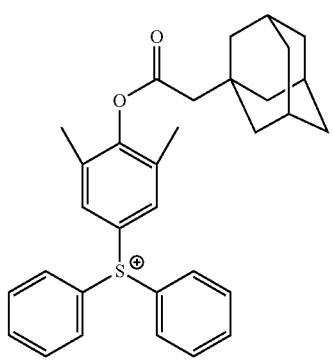
(ca-1-28)
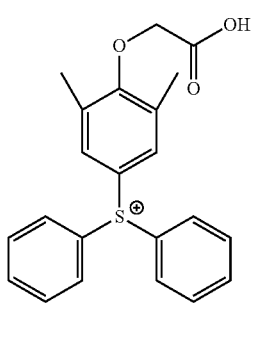
(ca-1-33)
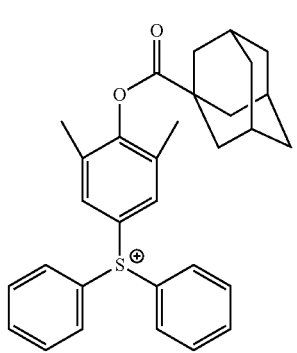
(ca-1-29)
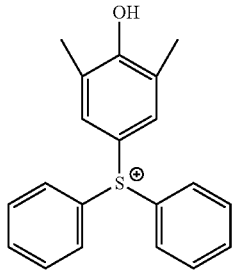
[Chemical Formula 55]
(ca-1-34)
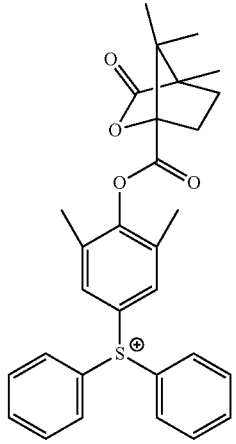
(ca-1-30)
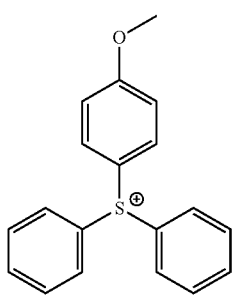
(ca-1-31)
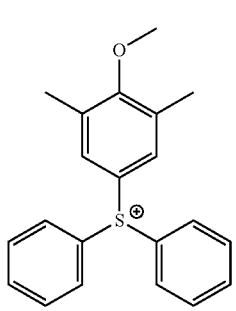
(ca-1-35)
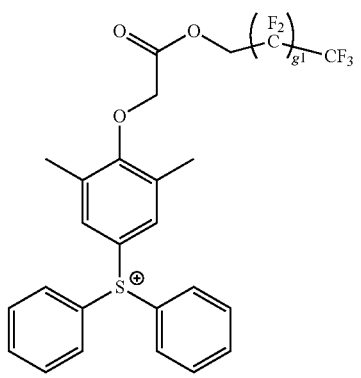

(ca-1-36) 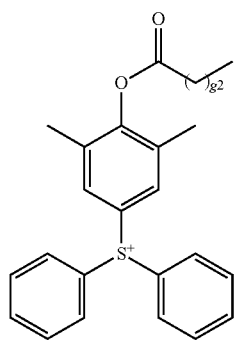
(ca-1-37) 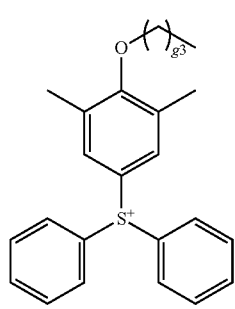
(ca-1-38) 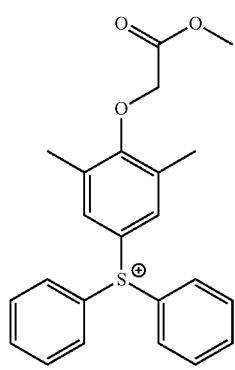
(ca-1-39) 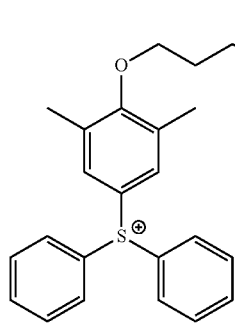
(ca-1-40) 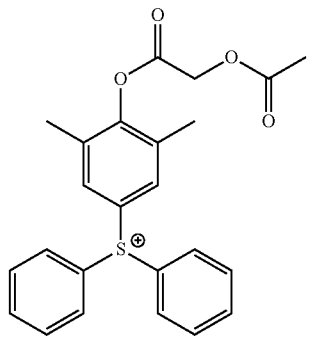
(ca-1-41) 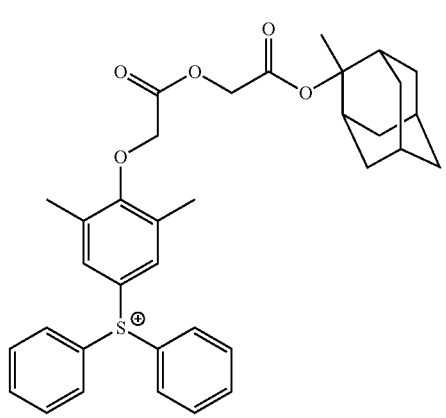
(ca-1-42) 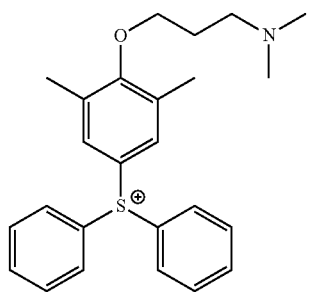
(ca-1-43) 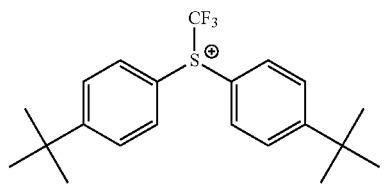
(ca-1-44) 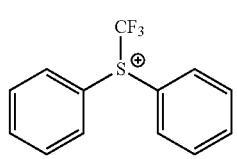
(ca-1-45) 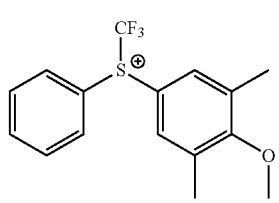

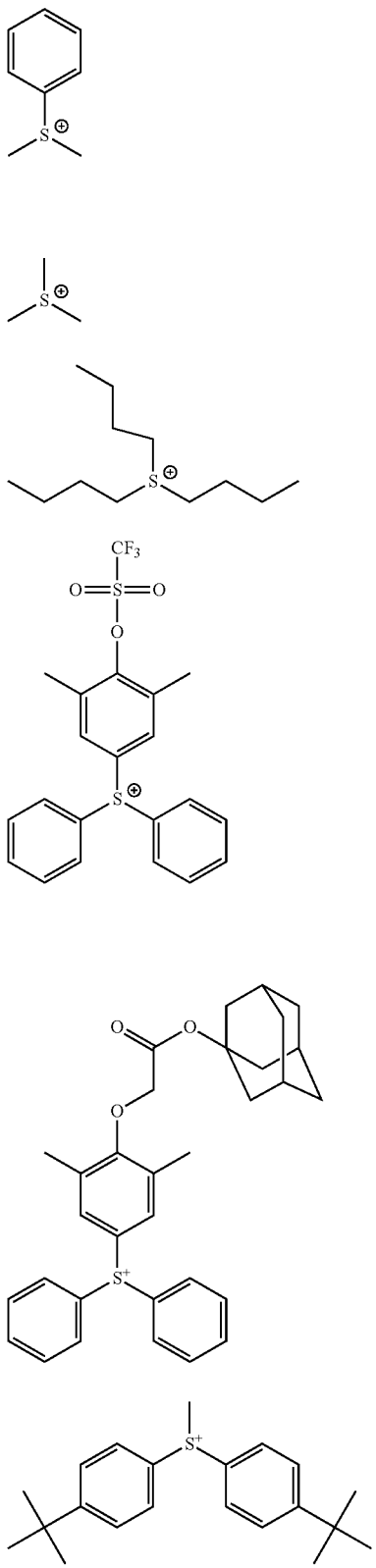
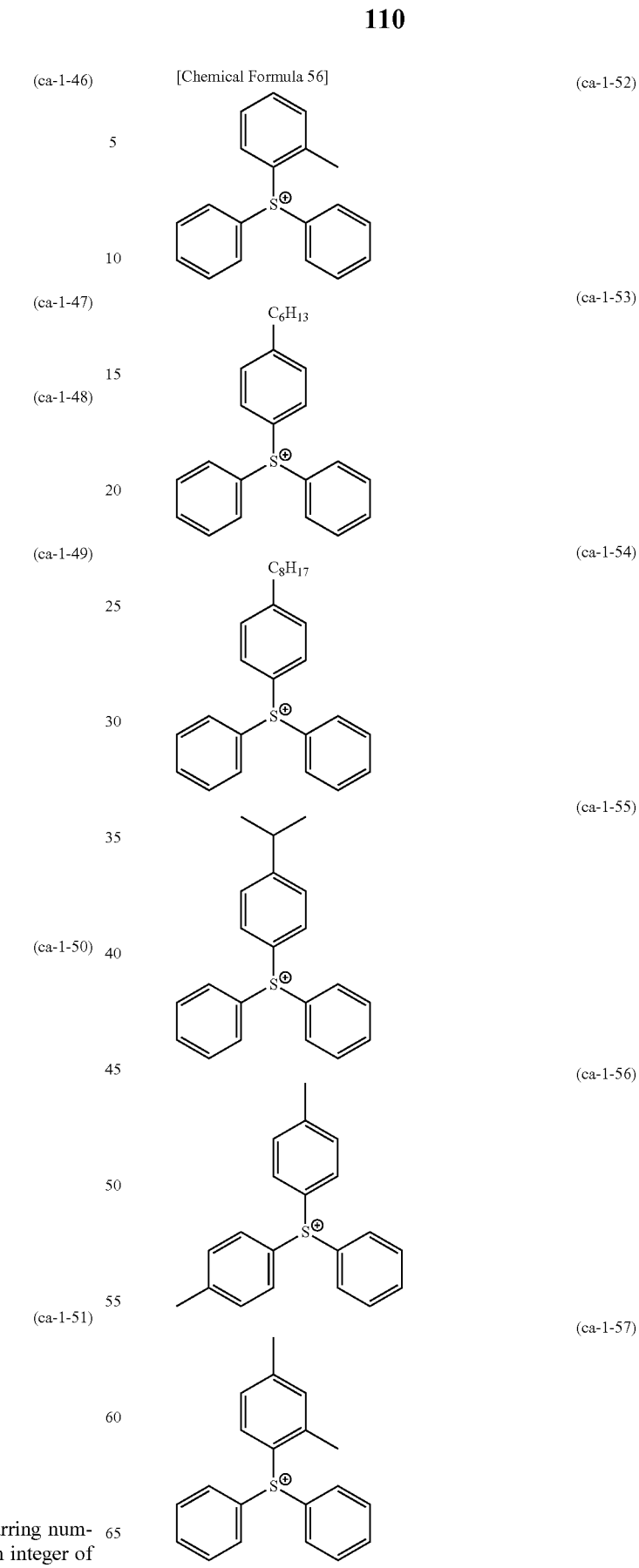
In the formulae, g1, g2 and g3 represent recurring numbers, wherein g1 is an integer of 1 to 5, g2 is an integer of 0 to 20, and g3 is an integer of 0 to 20.

(ca-1-58)
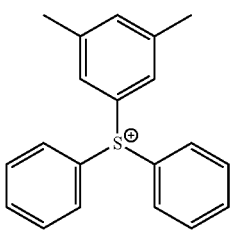
(ca-1-59)
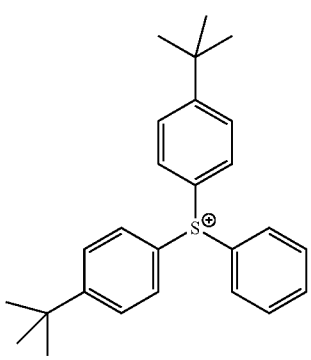
(ca-1-60)
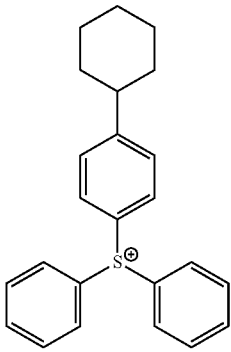
(ca-1-61)
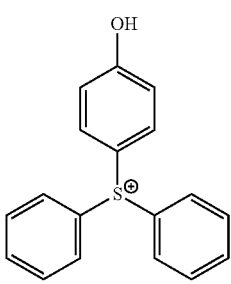
(ca-1-62)
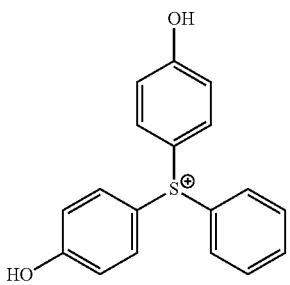
(ca-1-63)
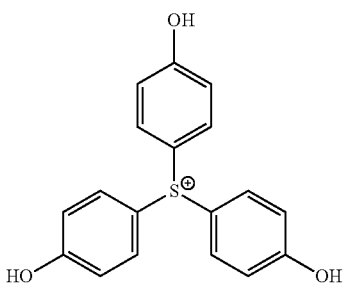
(ca-1-64)
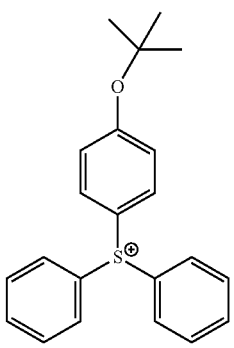
(ca-1-65)
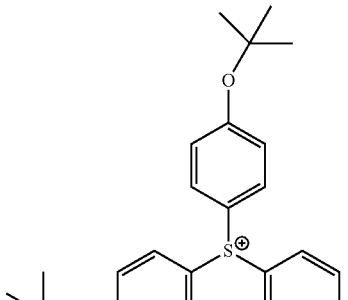
[Chemical Formula 57]
(ca-1-66)
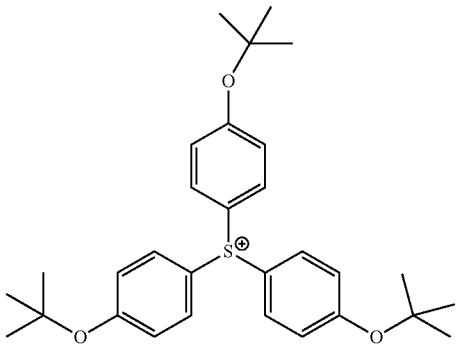

(ca-1-67)
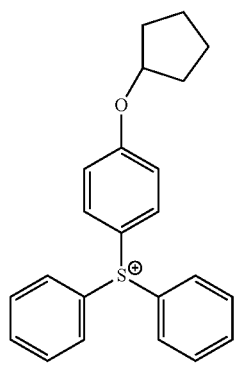
(ca-1-68)
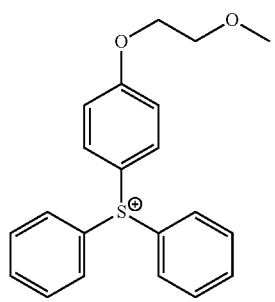
(ca-1-69)
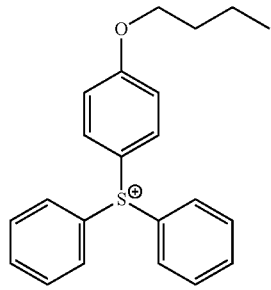
(ca-1-70)
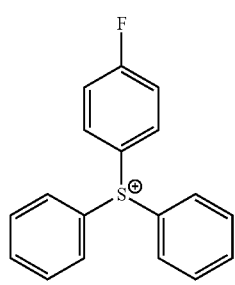
(ca-1-71)
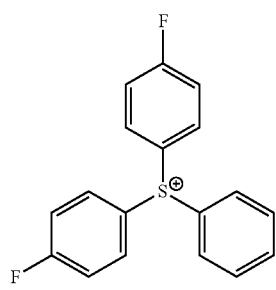
(ca-1-72)
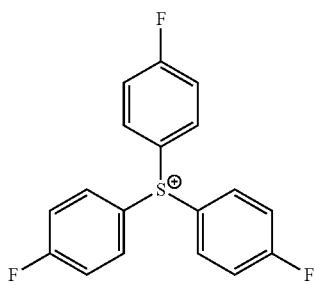
(ca-1-73)
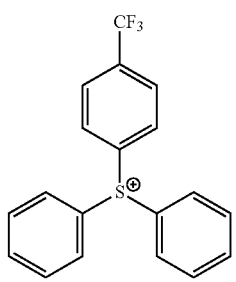
[Chemical Formula 58]
(ca-1-74)
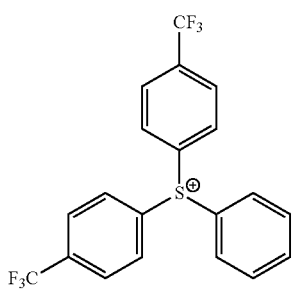
(ca-1-75)
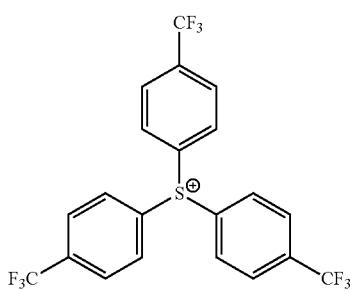
(ca-1-76)
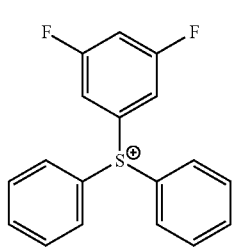

(ca-1-77) 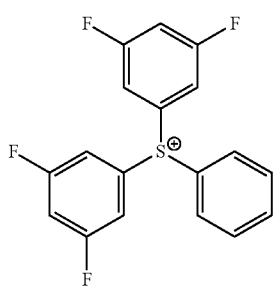
(ca-1-78) 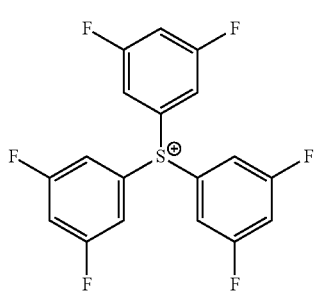
(ca-1-79) 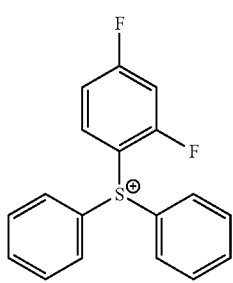
(ca-1-80) 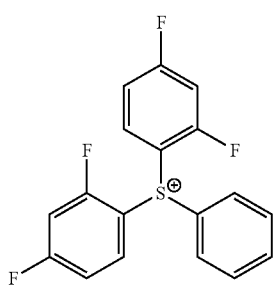
(ca-1-81) 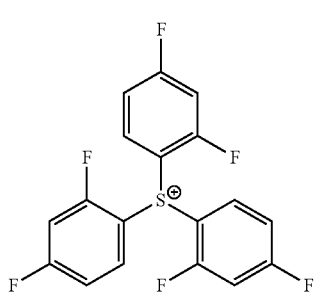
(ca-1-82) 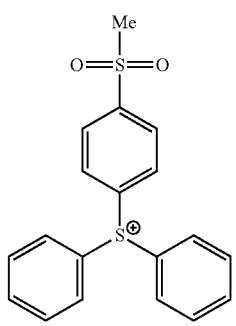
(ca-1-83) 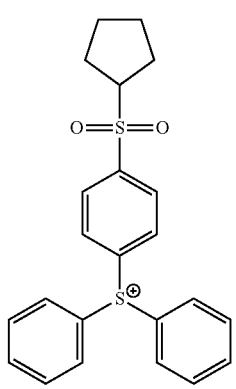
(ca-1-84) 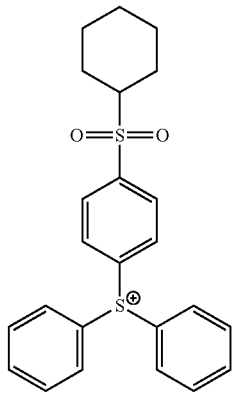
(ca-1-85) 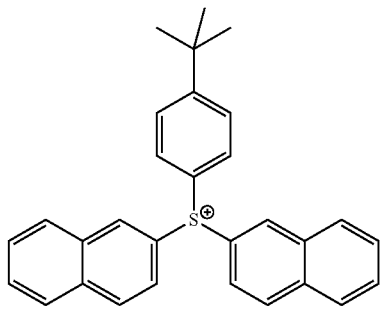

-continued
(ca-1-86)
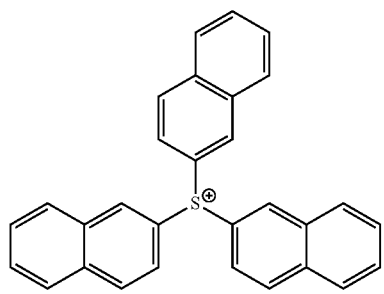
[Chemical Formula 59]
(ca-1-87)
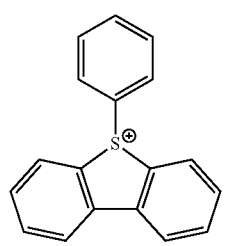
(ca-1-88)
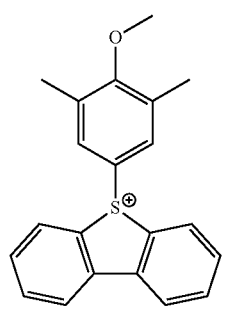
(ca-1-89)
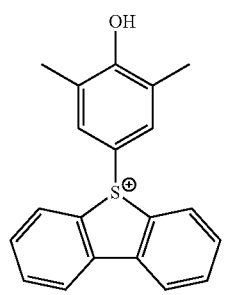
(ca-1-90)
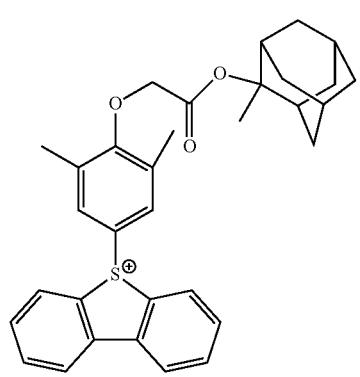
-continued
(ca-1-91)
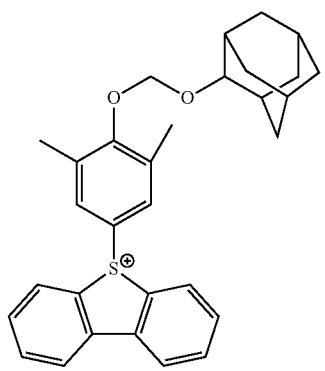
(ca-1-92)
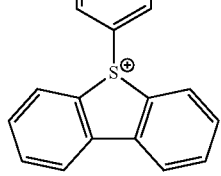
(ca-1-93)
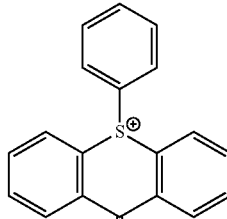
(ca-1-94)
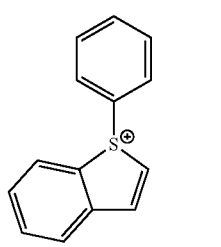
(ca-1-95)
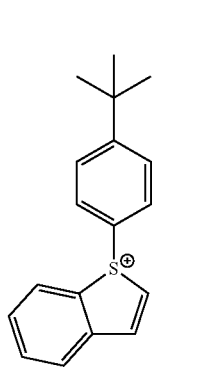

(ca-1-96)
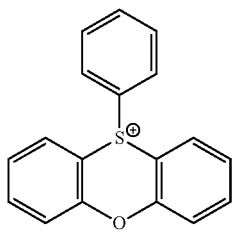
[Chemical Formula 60]
(ca-1-103)
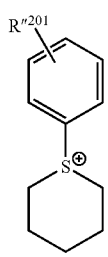
(ca-1-104)
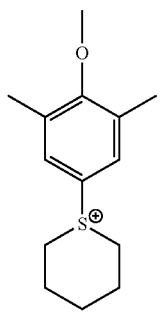
(ca-1-105)
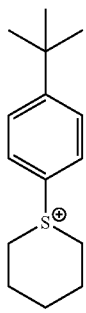
(ca-1-106)
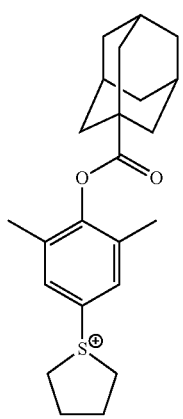
(ca-1-107)
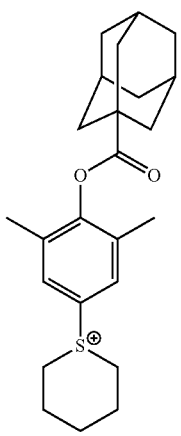
(ca-1-108)
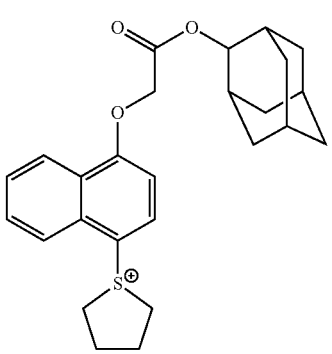
(ca-1-109)
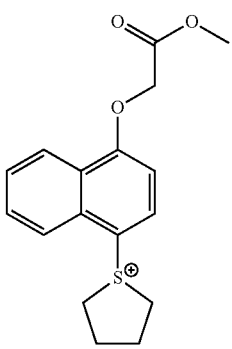
In the formulae, $R'^{201}$ represents a hydrogen atom or a substituent, and as the substituent, the same groups as those described above for substituting $R^{201}$ to $R^{207}$ and $R^{210}$ to $R^{212}$ can be mentioned.
[Chemical Formula 61]
(ca-1-110)
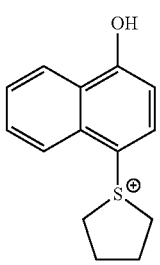

(ca-1-111)
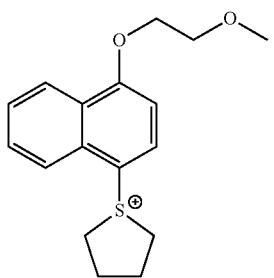
(ca-1-112)
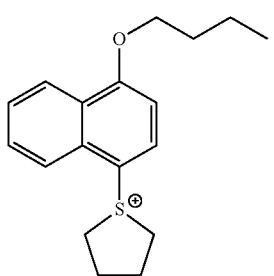
(ca-1-113)
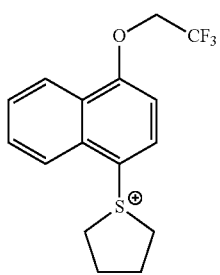
(ca-1-114)
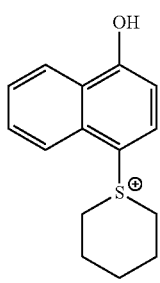
(ca-1-115)
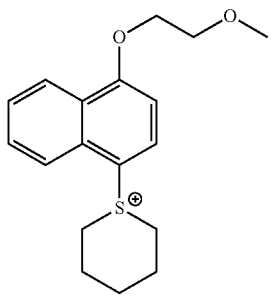
(ca-1-116)
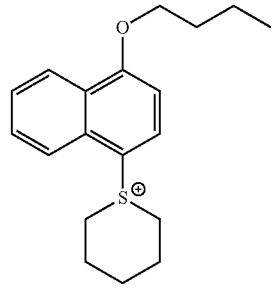
(ca-1-117)
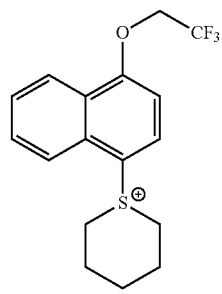
Specific examples of preferable cations represented by the formula (ca-2) include a dihphenyliodonium cation and a bis(4-tert-butylphenyl)iodonium cation.
Specific examples of preferable cations represented by formula (ca-3) include cations represented by formulae (ca-3-1) to (ca-3-6) shown below.
[Chemical Formula 62]
(ca-3-1)
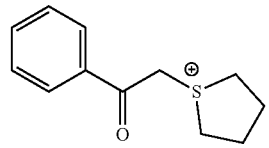
(ca-3-2)
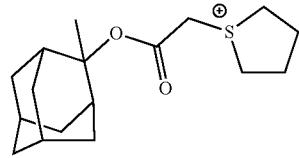
(ca-3-3)
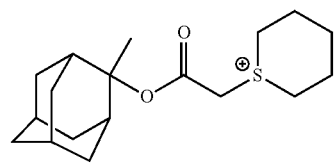
(ca-3-4)
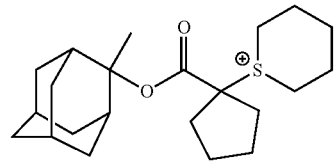

(ca-3-5)
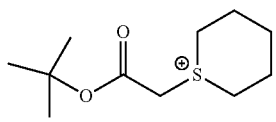
[Chemical Formula 63]
(ca-4-1)
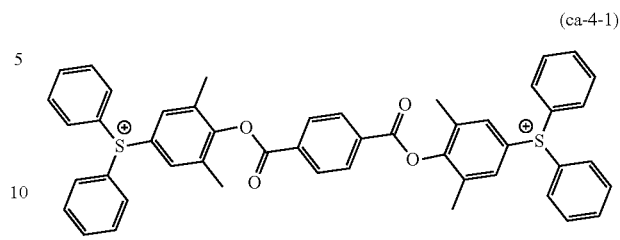
(ca-3-6)
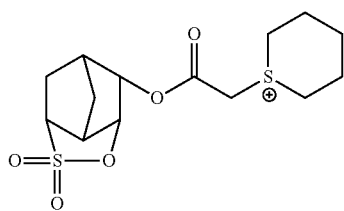
(ca-4-2)
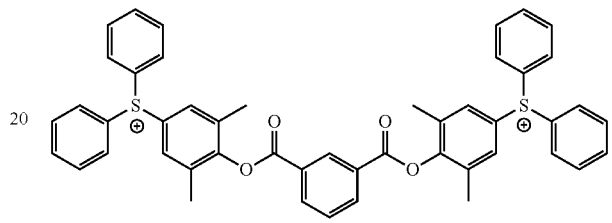
Specific examples of preferable cations represented by formula (ca-4) include cations represented by formulae (ca-4-1) and (ca-4-2) shown below.
Specific examples of preferable cations represented by formula (ca-5) include cations represented by formulae (ca-5-1) to (ca-5-3) shown below.
[Chemical Formula 64]
(ca-5-1)
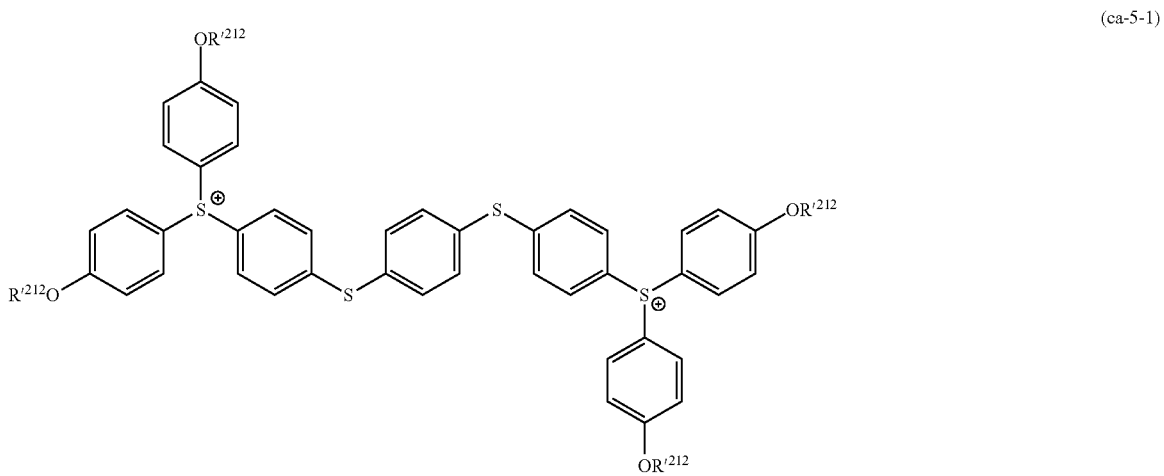

-continued
(ca-5-2)
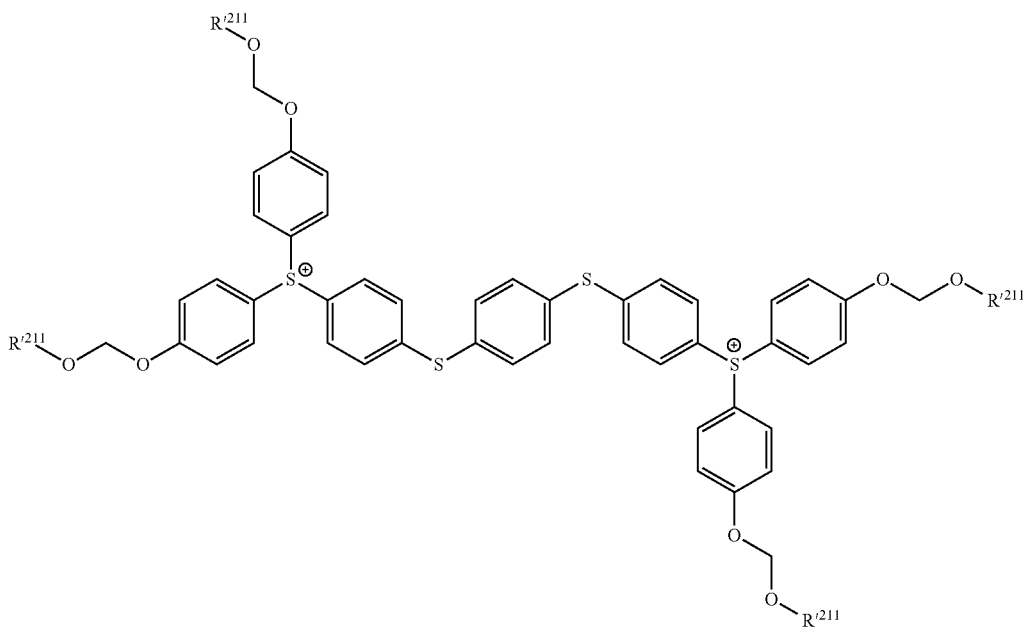
(ca-5-3)
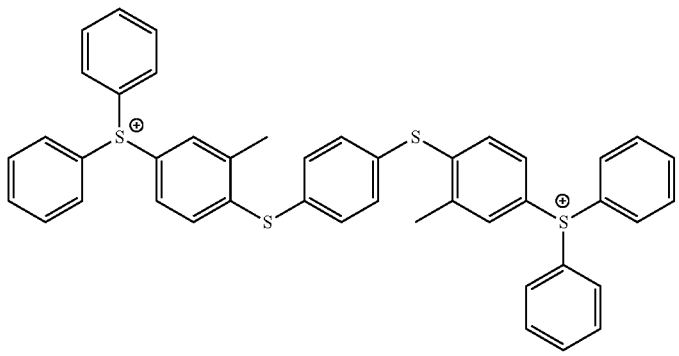
In the resist composition of the present embodiment, among the above examples, as the cation moiety of the component (D0), a cation represented by the aforementioned general formula (ca-1) is preferable.
Specific examples of the component (D0) are shown below, although the component (D0) is not limited to these examples.
[Chemical Formula 65]
(D0-1)
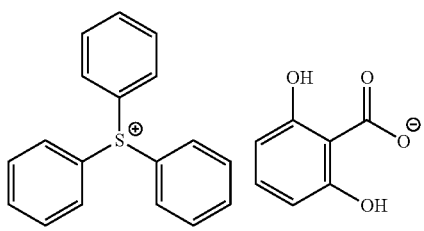
-continued
(D0-2)
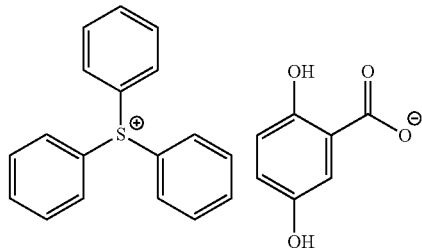
(D0-3)
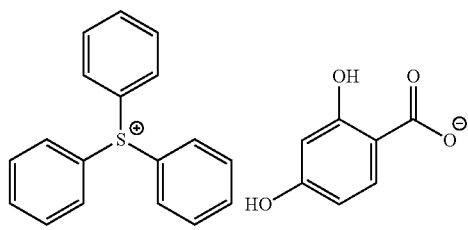

-continued

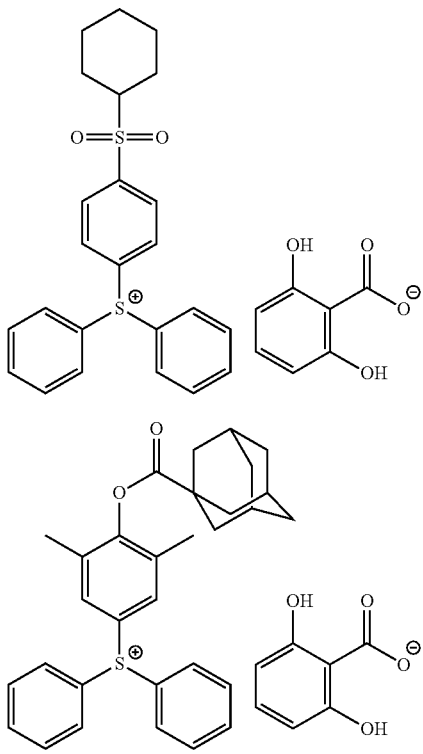

(D0-4)

(D0-5)

In the resist composition of the present embodiment, as the component (D0), one kind of compound may be used, or two or more kinds of compounds may be used in combination.

In the resist composition of the present embodiment, the amount of the component (D0) relative to 100 parts by weight of the component (A) is preferably 1 to 35 parts by weight, more preferably from 2 to 25 parts by weight, still more preferably from 3 to 20 parts by weight, and most preferably 3 to 15 parts by weight.

When the amount of the component (D0) is within the above-mentioned preferable range, solubility in a developing solution may be reliably assured, and the effects of the present invention may be more reliably achieved.

<Optional Components>

The resist composition of the present embodiment may contain, in addition to the aforementioned components (A) and (D0), any other optional components.

Examples of the optional components include the component (B), the component (D) (provided that the component (D0) is excluded), the component (E), the component (F) and the component (S) described below.

<<Component (B)>>

The component (B) is an acid generator component which generates acid upon exposure.

As the component (B), there is no particular limitation, and any of the known acid generators used in conventional chemically amplified resist compositions may be used.

Examples of these acid generators are numerous, and include onium salt acid generators such as iodonium salts and sulfonium salts; oxime sulfonate acid generators; diazomethane acid generators such as bisalkyl or bisaryl sulfonyl diazomethanes and poly(bis-sulfonyl)diazomethanes; nitrobenzylsulfonate acid generators; iminosulfonate acid generators; and disulfone acid generators.

As the onium salt acid generator, a compound represented by general formula (b-1) below (hereafter, sometimes referred to as "component (b-1)"), a compound represented by general formula (b-2) below (hereafter, sometimes referred to as "component (b-2)") or a compound represented by general formula (b-3) below (hereafter, sometimes referred to as "component (b-3)") may be mentioned.

[Chemical Formula 66]

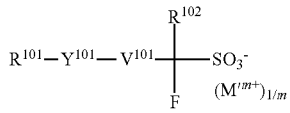

(b-1)

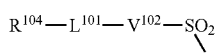

(b-2)

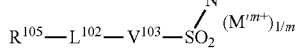

(b-3)

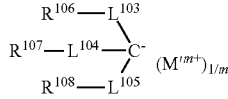

In the formulae, $R^{101}$ and $R^{104}$ to $R^{108}$ each independently represents a cyclic group which may have a substituent, a chain-like alkyl group which may have a substituent or a chain-like alkenyl group which may have a substituent, provided that $R^{104}$ and $R^{105}$ may be mutually bonded to form a ring structure; $R^{102}$ represents a fluorine atom or a fluorinated alkyl group having 1 to 5 carbon atoms; $Y^{101}$ represents a single bond or a divalent group containing an oxygen atom; $V^{101}$ to $V^{103}$ each independently represents a single bond, an alkylene group or a fluorinated alkylene group; $L^{101}$ and $L^{102}$ each independently represents a single bond or an oxygen atom; $L^{103}$ to $L^{105}$ each independently represents a single bond, —CO— or —SO$_2$—; m represents an integer of 1 or more; and $M^{m+}$ represents an m-valent onium cation.

{Anion Moiety}

—Anion Moiety of Component (b-1)

In the formula (b-1), $R^{101}$ represents a cyclic group which may have a substituent, a chain-like alkyl group which may have a substituent or a chain-like alkenyl group which may have a substituent.

Cyclic Group which May have a Substituent:

The cyclic group is preferably a cyclic hydrocarbon group, and the cyclic hydrocarbon group may be either an aromatic hydrocarbon group or an aliphatic hydrocarbon group. An "aliphatic hydrocarbon group" refers to a hydrocarbon group that has no aromaticity. The aliphatic hydrocarbon group may be either saturated or unsaturated, but in general, the aliphatic hydrocarbon group is preferably saturated.

The aromatic hydrocarbon group for $R^{101}$ is a hydrocarbon group having an aromatic ring. The aromatic hydrocarbon ring preferably has 3 to 30 carbon atoms, more preferably 5 to 30, still more preferably 5 to 20, still more preferably 6 to 15, and most preferably 6 to 10. Here, the number of carbon atoms within a substituent(s) is not included in the number of carbon atoms of the aromatic hydrocarbon group.

Examples of the aromatic ring contained in the aromatic hydrocarbon group represented by $R^{101}$ include benzene, fluorene, naphthalene, anthracene, phenanthrene and biphenyl; and aromatic hetero rings in which part of the carbon atoms constituting the aforementioned aromatic rings has been substituted with a hetero atom. Examples of the hetero atom within the aromatic hetero rings include an oxygen atom, a sulfur atom and a nitrogen atom.

Specific examples of the aromatic hydrocarbon group represented by $R^{101}$ include a group in which one hydrogen atom has been removed from the aforementioned aromatic ring (i.e., an aryl group, such as a phenyl group or a naphthyl group), and a group in which one hydrogen of the aforementioned aromatic ring has been substituted with an alkylene group (e.g., an arylalkyl group such as a benzyl group, a phenethyl group, a 1-naphthylmethyl group, a 2-naphthylmethyl group, a 1-naphthylethyl group or a 2-naphthylethyl group). The alkylene group (alkyl chain within the arylalkyl group) preferably has 1 to 4 carbon atom, more preferably 1 or 2, and most preferably 1.

Examples of the cyclic aliphatic hydrocarbon group for $R^{101}$ include aliphatic hydrocarbon groups containing a ring in the structure thereof.

As examples of the hydrocarbon group containing a ring in the structure thereof, an alicyclic hydrocarbon group (a group in which one hydrogen atom has been removed from an aliphatic hydrocarbon ring), a group in which the alicyclic hydrocarbon group is bonded to the terminal of the aforementioned chain-like aliphatic hydrocarbon group, and a group in which the alicyclic group is interposed within the aforementioned linear or branched aliphatic hydrocarbon group, can be given.

The alicyclic hydrocarbon group preferably has 3 to 20 carbon atoms, and more preferably 3 to 12 carbon atoms.

The alicyclic hydrocarbon group may be either a polycyclic group or a monocyclic group. As the monocyclic alicyclic hydrocarbon group, a group in which one or more hydrogen atoms have been removed from a monocycloalkane is preferable. The monocycloalkane preferably has 3 to 6 carbon atoms, and specific examples thereof include cyclopentane and cyclohexane. As the polycyclic alicyclic hydrocarbon group, a group in which one or more hydrogen atoms have been removed from a polycycloalkane is preferable, and the polycyclic group preferably has 7 to 30 carbon atoms. Among polycycloalkanes, a polycycloalkane having a bridged ring polycyclic skeleton, such as adamantane, norbornane, isobornane, tricyclodecane or tetracyclododecane, and a polycycloalkane having a condensed ring polycyclic skeleton, such as a cyclic group having a steroid skeleton are preferable.

Among these examples, as the cyclic aliphatic hydrocarbon group for $R^{101}$, a group in which one or more hydrogen atoms have been removed from a monocycloalkane or a polycycloalkane is preferable, a group in which one or more hydrogen atoms have been removed from a polycycloalkane is more preferable, an adamantyl group or a norbornyl group is still more preferable, and an adamantyl group is most preferable.

The linear aliphatic hydrocarbon group which may be bonded to the alicyclic hydrocarbon group preferably has 1 to 10 carbon atoms, more preferably 1 to 6 carbon atoms, still more preferably 1 to 4 carbon atoms, and most preferably 1 to 3 carbon atoms. As the linear aliphatic hydrocarbon group, a linear alkylene group is preferable. Specific examples thereof include a methylene group [—$CH_2$—], an ethylene group [—$(CH_2)_2$—], a trimethylene group [—$(CH_2)_3$—], a tetramethylene group [—$(CH_2)_4$—] and a pentamethylene group [—$(CH_2)_5$—].

The branched aliphatic hydrocarbon group which may be bonded to the alicyclic hydrocarbon group preferably has 2 to 10 carbon atoms, more preferably 3 to 6 carbon atoms, still more preferably 3 or 4 carbon atoms, and most preferably 3 carbon atoms. As the branched aliphatic hydrocarbon group, branched alkylene groups are preferred, and specific examples include various alkylalkylene groups, including alkylmethylene groups such as —$CH(CH_3)$—, —$CH(CH_2CH_3)$—, —$C(CH_3)_2$—, —$C(CH_3)(CH_2CH_3)$—, —$C(CH_3)(CH_2CH_2CH_3)$—, and —$C(CH_2CH_3)_2$—; alkylethylene groups such as —$CH(CH_3)CH_2$—, —$CH(CH_3)CH(CH_3)$—, —$C(CH_3)_2CH_2$—, —$CH(CH_2CH_3)CH_2$—, and —$C(CH_2CH_3)_2$—$CH_2$—; alkyltrimethylene groups such as —$CH(CH_3)CH_2CH_2$—, and —$CH_2CH(CH_3)CH_2$—; and alkyltetramethylene groups such as —$CH(CH_3)CH_2CH_2CH_2$—, and —$CH_2CH(CH_3)CH_2CH_2$—. As the alkyl group within the alkylalkylene group, a linear alkyl group of 1 to 5 carbon atoms is preferable.

The cyclic hydrocarbon group for $R^{101}$ may contain a hetero atom such as a heterocycle. Specific examples include lactone-containing cyclic groups represented by the aforementioned general formulae (a2-r-1) to (a2-r-7), the —$SO_2$— containing cyclic group represented by the aforementioned formulae (a5-r-1) to (a5-r-4), and other heterocyclic groups represented by chemical formulae (r-hr-1) to (r-hr-16) shown below. In the formulae, * indicates the bonding site which bonds to $Y^\circ$ in formula (b-1).

[Chemical Formula 67]

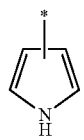

(r-hr-1)

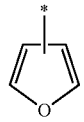

(r-hr-2)

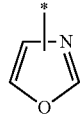

(r-hr-3)

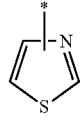

(r-hr-4)

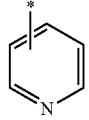

(r-hr-5)

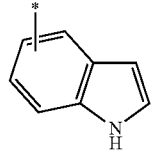

(r-hr-6)

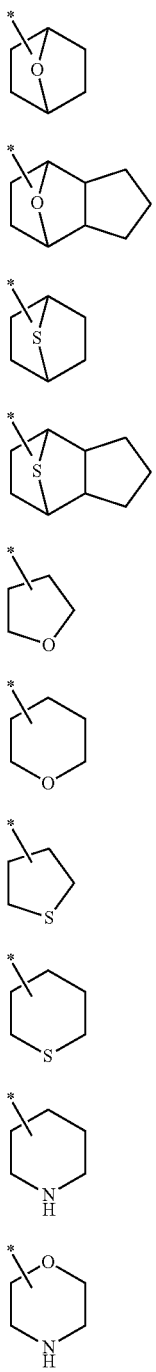

(r-hr-7)
(r-hr-8)
(r-hr-9)
(r-hr-10)
(r-hr-11)
(r-hr-12)
(r-hr-13)
(r-hr-14)
(r-hr-15)
(r-hr-16)

As the substituent for the cyclic group for $R^{101}$, an alkyl group, an alkoxy group, a halogen atom, a halogenated alkyl group, a hydroxyl group, a carbonyl group, a nitro group or the like can be used. The alkyl group as the substituent is preferably an alkyl group of 1 to 5 carbon atoms, and a methyl group, an ethyl group, a propyl group, an n-butyl group or a tert-butyl group is particularly desirable.

The alkoxy group as the substituent is preferably an alkoxy group having 1 to 5 carbon atoms, more preferably a methoxy group, ethoxy group, n-propoxy group, iso-propoxy group, n-butoxy group or tert-butoxy group, and most preferably a methoxy group or an ethoxy group.

The halogen atom as the substituent is preferably a fluorine atom.

Example of the aforementioned halogenated alkyl group includes a group in which a part or all of the hydrogen atoms within an alkyl group of 1 to 5 carbon atoms (e.g., a methyl group, an ethyl group, a propyl group, an n-butyl group or a tert-butyl group) have been substituted with the aforementioned halogen atoms.

The carbonyl group as the substituent is a group that substitutes a methylene group (—$CH_2$—) constituting the cyclic hydrocarbon group.

The cyclic hydrocarbon group for $R^{101}$ may be a condensed cyclic group in which an aliphatic hydrocarbon ring and an aromatic hydrocarbon ring are fused. Examples of the condensed ring include a compound in which one or more aromatic rings are fused with a polycycloalkane having a bridged polycyclic skeleton. Specific examples of the bridged polycycloalkane include a bicycloalkane, such as bicyclo[2.2.1]heptane (norbornane) or bicyclo [2.2.2]octane. As the condensed cyclic group, a group containing a condensed ring in which 2 or 3 aromatic rings are fused with a bicycloalkane is preferable, and a group containing a condensed ring in which 2 or 3 aromatic rings are fused with bicyclo[2.2.2]octane is more preferable. Specific examples of the condensed cyclic group for $R^{101}$ include groups represented by formulae (r-br-1) and (r-br-2) shown below. In the formulae, * indicates the bonding site which bonds to $Y^{101}$ in formula (b-1).

[Chemical Formula 68]

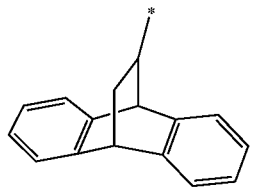

(r-br-1)

(r-br-2)

As the substituent for the condensed cyclic group for $R^{101}$, an alkyl group, an alkoxy group, a halogen atom, a halogenated alkyl group, a hydroxy group, a carbonyl group, a nitro group, an aromatic hydrocarbon group or an alicyclic hydrocarbon group may be mentioned.

The alkyl group, the alkoxy group, the halogen atom and the halogenated alkyl group as the substituent for the condensed cyclic group are the same as defined for the substituents for the cyclic group represented by $R^{101}$.

Examples of the aromatic hydrocarbon group as the substituent for the condensed cyclic group include a group in which one hydrogen atom has been removed from an aromatic hydrocarbon ring (an aryl group, such as a phenyl group or a naphthyl group); a group in which one hydrogen atom of the aforementioned aromatic hydrocarbon ring has been substituted with an alkylene group (an arylalkyl group such as a benzyl group, a phenethyl group, a 1-naphthylmethyl group, a 2-naphthylmethyl group, a 1-naphthylethyl group, or a 2-naphthylethyl group); and a heterocyclic group represented by any of the aforementioned formulae (r-hr-1) to (r-hr-6).

Examples of the alicyclic hydrocarbon group as the substituent for the condensed cyclic group include a group in which one hydrogen atom has been removed from a monocycloalkane such as cyclopentane or cyclohexane; a group in which one hydrogen atom has been removed from a polycycloalkane such as adamantane, norbornane, isobornane, tricyclodecane or tetracyclododecane; a lactone-containing cyclic group represented by any of the aforementioned general formulae (a2-r-1) to (a2-r-7); an —$SO_2$-containing cyclic group represented by any of the aforementioned general formulae (a5-r-1) to (a5-r-4); and a heterocyclic group represented by any of the aforementioned formulae (r-hr-7) to (r-hr-16).

Chain Alkyl Group which May have a Substituent:

The chain-like alkyl group for $R^{101}$ may be linear or branched.

The linear alkyl group preferably has 1 to 20 carbon atoms, more preferably 1 to 15, and most preferably 1 to 10. Specific examples include a methyl group, an ethyl group, a propyl group, a butyl group, a pentyl group, a hexyl group, a heptyl group, an octyl group, a nonyl group, a decyl group, an undecyl group, a dodecyl group, a tridecyl group, an isotridecyl group, a tetradecyl group, a pentadecyl group, a hexadecyl group, an isohexadecyl group, a heptadecyl group, an octadecyl group, a nonadecyl group, an icosyl group, a henicosyl group and a docosyl group.

The branched alkyl group preferably has 3 to 20 carbon atoms, more preferably 3 to 15, and most preferably 3 to 10. Specific examples include a 1-methylethyl group, a 1-methylpropyl group, a 2-methylpropyl group, a 1-methylbutyl group, a 2-methylbutyl group, a 3-methylbutyl group, a 1-ethylbutyl group, a 2-ethylbutyl group, a 1-methylpentyl group, a 2-methylpentyl group, a 3-methylpentyl group and a 4-methylpentyl group.

Chain Alkenyl Group which May have a Substituent:

The chain-like alkenyl group for $R^{101}$ may be linear or branched, and preferably has 2 to 10 carbon atoms, more preferably 2 to 5 carbon atoms, still more preferably 2 to 4 carbon atoms, and most preferably 3 carbon atoms. Examples of linear alkenyl groups include a vinyl group, a propenyl group (an allyl group) and a butynyl group. Examples of branched alkenyl groups include a 1-methylvinyl group, a 2-methylvinyl group, a 1-methylpropenyl group and a 2-methylpropenyl group.

Among these examples, as the chain-like alkenyl group, a linear alkenyl group is preferable, a vinyl group or a propenyl group is more preferable, and a vinyl group is most preferable.

As the substituent for the chain-like alkyl group or alkenyl group for $R^{101}$, an alkoxy group, a halogen atom, a halogenated alkyl group, a hydroxyl group, a carbonyl group, a nitro group, an amino group, a cyclic group for $R^{101}$ or the like can be used.

Among the above examples, as $R^{101}$, a cyclic group which may have a substituent is preferable, and a cyclic hydrocarbon group which may have a substituent is more preferable. Specifically, a phenyl group, a naphthyl group, a group in which one or more hydrogen atoms have been removed from a polycycloalkane, a lactone-containing cyclic group represented by any one of the aforementioned formula (a2-r-1) to (a2-r-7), and an —$SO_2$— containing cyclic group represented by any one of the aforementioned formula (a5-r-1) to (a5-r-4).

In formula (b-1), $Y^{101}$ represents a single bond or a divalent linking group containing an oxygen atom.

In the case where $Y^{101}$ is a divalent linking group containing an oxygen atom, $Y^{101}$ may contain an atom other than an oxygen atom. Examples of atoms other than an oxygen atom include a carbon atom, a hydrogen atom, a sulfur atom and a nitrogen atom.

Examples of divalent linking groups containing an oxygen atom include non-hydrocarbon, oxygen atom-containing linking groups such as an oxygen atom (an ether bond; —O—), an ester bond (—C(=O)—O—), an oxycarbonyl group (—O—C(=O)—), an amido bond (—C(=O)—NH—), a carbonyl group (—C(=O)—) and a carbonate bond (—O—C(=O)—O—); and combinations of the aforementioned non-hydrocarbon, hetero atom-containing linking groups with an alkylene group. Furthermore, the combinations may have a sulfonyl group (—$SO_2$—) bonded thereto. Examples of the divalent linking group containing an oxygen atom include divalent linking groups represented by general formula (y-a1-1) to (y-a1-7) shown below.

[Chemical Formula 69]

(y-a1-1)

(y-a1-2)

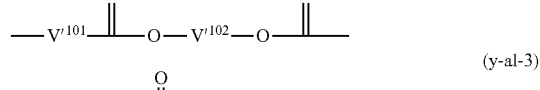
(y-a1-3)

(y-a1-4)

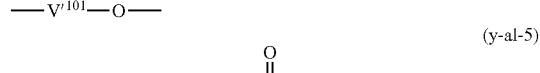
(y-a1-5)

(y-a1-6)

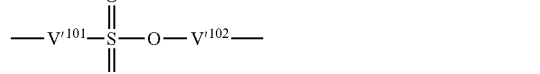
(y-a1-7)

In the formulae, $V'^{101}$ represents a single bond or an alkylene group of 1 to 5 carbon atoms; $V'^{102}$ represents a divalent saturated hydrocarbon group of 1 to 30 carbon atoms.

The divalent saturated hydrocarbon group for $V'^{102}$ is preferably an alkylene group of 1 to 30 carbon atoms, more preferably an alkylene group of 1 to 10 carbon atoms, and still more preferably an alkylene group of 1 to 5 carbon atoms.

The alkylene group for $V'^{101}$ and $V'^{102}$ may be a linear alkylene group or a branched alkylene group, and a linear alkylene group is preferable.

Specific examples of the alkylene group for $V'^{101}$ and $V'^{102}$ include a methylene group [—$CH_2$—]; an alkylmethylene group, such as —CH($CH_3$)—, —CH($CH_2CH_3$)—, —C($CH_3$)$_2$—, —C($CH_3$)($CH_2CH_3$)—, —C($CH_3$)($CH_2CH_2CH_3$)— and —C($CH_2CH_3$)$_2$—; an ethylene group [—$CH_2CH_2$—]; an alkylethylene group, such as —CH $(CH_3)CH_2—$, $—CH(CH_3)CH(CH_3)—$, $—C(CH_3)_2CH_2—$ and $—CH(CH_2CH_3)CH_2—$; a trimethylene group (n-propylene group) $[—CH_2CH_2CH_2—]$; an alkyltrimethylene group, such as $—CH(CH_3)CH_2CH_2—$ and $—CH_2CH(CH_3)CH_2—$; a tetramethylene group $[—CH_2CH_2CH_2CH_2—]$; an alkyltetramethylene group, such as $—CH(CH_3)CH_2CH_2CH_2—$, $—CH_2CH(CH_3)CH_2CH_2—$; and a pentamethylene group $[—CH_2CH_2CH_2CH_2CH_2—]$.

Further, part of methylene group within the alkylene group for $V'^{101}$ and $V'^{102}$ may be substituted with a divalent aliphatic cyclic group of 5 to 10 carbon atoms. The aliphatic cyclic group is preferably a divalent group in which one hydrogen atom has been removed from the cyclic aliphatic hydrocarbon group (monocyclic aliphatic hydrocarbon group or polycyclic aliphatic hydrocarbon group) for $Ra'^3$ in the aforementioned formula (a1-r-1), and a cyclohexylene group, 1,5-adamantylene group or 2,6-adamantylene group is preferable.

$Y^{101}$ is preferably a divalent linking group containing an ether bond or a divalent linking group containing an ester bond, and groups represented by the aforementioned formulas (y-a1-1) to (y-a1-5) are preferable.

In formula (b-1), $V^{101}$ represents a single bond, an alkylene group or a fluorinated alkylene group. The alkylene group and the fluorinated alkylene group for $V^{101}$ preferably has 1 to 4 carbon atoms. Examples of the fluorinated alkylene group for $V^{101}$ include a group in which part or all of the hydrogen atoms within the alkylene group for $V^{101}$ have been substituted with fluorine. Among these examples, as $V^{101}$, a single bond or a fluorinated alkylene group of 1 to 4 carbon atoms is preferable.

In formula (b-1), $R^{102}$ represents a fluorine atom or a fluorinated alkyl group of 1 to 5 carbon atoms. $R^{102}$ is preferably a fluorine atom or a perfluoroalkyl group of 1 to 5 carbon atoms, and more preferably a fluorine atom.

Specific examples of the anion moiety represented by formula (b-1) include a fluorinated alkylsulfonate anion such as a trifluoromethanesulfonate anion or a perfluorobutanesulfonate anion in the case where $Y^{101}$ is a single bond; and an anion represented by any one of formulae (an-1) to (an-3) in the case where $Y^{101}$ represents a divalent linking group containing an oxygen atom.

[Chemical Formula 70]

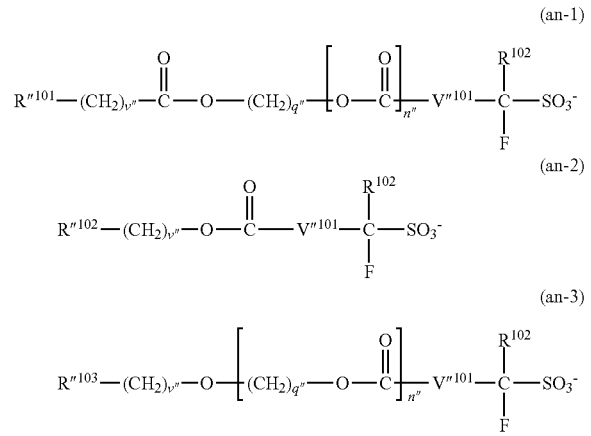

(an-1)

(an-2)

(an-3)

In the formulae, $R'''^{101}$ represents an aliphatic cyclic group which may have a substituent, a monovalent heterocyclic group represented by any of the aforementioned formulae (r-hr-1) to (r-hr-6), a condensed cyclic group represented by the aforementioned formula (r-br-1) or (r-br-2), or a chain-like alkyl group which may have a substituent; $R'''^{102}$ represents an aliphatic cyclic group which may have a substituent, a condensed cyclic group represented by the aforementioned formula (r-br-1) or (r-br-2), a lactone-containing cyclic group represented by any of the aforementioned formulae (a2-r-1) and (a2-r-3) to (a2-r-7), or a $—SO_2-$ containing cyclic group represented by any of formulae (a5-r-1) to (a5-r-4); $R'''^{103}$ represents an aromatic cyclic group which may have a substituent, an aliphatic cyclic group which may have a substituent, or a chain-like alkenyl group which may have a substituent; $V'''^{101}$ represents a single bond, an alkylene group having 1 to 4 carbon atoms or a fluorinated alkylene group having 1 to 4 carbon atoms; $R^{102}$ represents a fluorine atom or a fluorinated alkyl group of 1 to 5 carbon atoms; each $v''$ independently represents an integer of 0 to 3; each $q''$ independently represents an integer of 0 to 20; and $n''$ represents 0 or 1.

As the aliphatic cyclic group for $R'''^{101}$, $R'''^{102}$ and $R'''^{103}$ which may have a substituent, the same groups as the cyclic aliphatic hydrocarbon group for $R^{101}$ in the aforementioned formula (b-1) are preferable. Examples of the substituent include the same substituents as those described above for the cyclic aliphatic hydrocarbon group for $R^{101}$ in the aforementioned formula (b-1).

As the aromatic cyclic group for $R'''^{103}$ which may have a substituent, the same groups as the aromatic hydrocarbon group for the cyclic hydrocarbon group represented by $R^{101}$ in the aforementioned formula (b-1) is preferable. Examples of the substituent include the same substituents as those described above for the aromatic hydrocarbon group for $R^{101}$ in the aforementioned formula (b-1).

As the chain alkyl group for $R'''^{101}$ which may have a substituent, the same chain alkyl groups as those described above for $R^{101}$ in the aforementioned formula (b-1) are preferable.

As the chain alkenyl group for $R'''^{103}$ which may have a substituent, the same chain alkenyl groups as those described above for $R^{101}$ in the aforementioned formula (b-1) are preferable.

—Anion Moiety of Component (b-2)

In formula (b-2), $R^{104}$ and $R^{105}$ each independently represents a cyclic group which may have a substituent, a chain-like alkyl group which may have a substituent or a chain-like alkenyl group which may have a substituent, and is the same as defined for $R^{101}$ in formula (b-1). $R^{104}$ and $R^{105}$ may be mutually bonded to form a ring.

As $R^{104}$ and $R^{105}$, a chain-like alkyl group which may have a substituent is preferable, and a linear or branched alkyl group or a linear or branched fluorinated alkyl group is more preferable.

The chain-like alkyl group preferably has 1 to 10 carbon atoms, more preferably 1 to 7 carbon atoms, and still more preferably 1 to 3 carbon atoms. The smaller the number of carbon atoms of the chain-like alkyl group for $R^{104}$ and $R^{105}$, the more the solubility in a resist solvent is improved. Further, in the chain alkyl group for $R^{104}$ and $R^{105}$, the larger the number of hydrogen atoms being substituted with fluorine atom(s), the acid strength becomes stronger, and the transparency to a high energy beam having a wavelength of no more than 250 nm or electron beam may be improved. The fluorination ratio of the chain-like alkyl group is preferably from 70 to 100%, more preferably from 90 to 100%, and it is particularly desirable that the chain-like alkyl group be a perfluoroalkyl group in which all hydrogen atoms are substituted with fluorine atoms.

In formula (b-2), $V^{102}$ and $V^{103}$ each independently represents a single bond, an alkylene group or a fluorinated alkylene group, and is the same as defined for $V^{101}$ in formula (b-1).

In formula (b-2), $L^{101}$ and $L^{102}$ each independently represents a single bond or an oxygen atom.

—Anion Moiety of Component (b-3)

In formula (b-3), $R^{106}$ to $R^{108}$ each independently represents a cyclic group which may have a substituent, a chain-like alkyl group which may have a substituent or a chain-like alkenyl group which may have a substituent, and is the same as defined for $R^{101}$ in formula (b-1).

In formula (b-3), $L^{103}$ to $L^{105}$ each independently represents a single bond, —CO— or —SO$_2$—.

Among these examples, as the anion moiety of the component (B), an anion for the component (b-1) is preferable. Among these, an anion represented by any one of the aforementioned general formulae (an-1) to (an-3) is more preferable, and an anion represented by the aforementioned general formula (an-1) or (an-2) is more preferable, and an anion represented by the aforementioned general formula (an-2) is still more preferable.

{Cation Moiety}

In formulae (b-1), (b-2) and (b-3), $M'^{m+}$ represents an m-valent onium cation. Among these, a sulfonium cation or a iodonium cation is preferable. m represents an integer of 1 or more.

Preferable examples of the cation moiety (($M'^{m+})_{1/m}$) include an organic cation represented by any of the aforementioned general formulae (ca-1) to (ca-5) for the component (D0) is preferable. Among these examples, a cation represented by general formula (ca-1) is preferable.

In the resist composition of the present embodiment, as the component (B), one kind of compound may be used, or two or more kinds of compounds may be used in combination.

When the resist composition contains the component (B), the amount of the component (B) relative to 100 parts by weight of the component (A) is preferably less than 50 parts by weight, more preferably 1 to 40 parts by weight, and still more preferably 5 to 25 parts by weight.

When the amount of the component (B) is within the above-mentioned preferable range, pattern formation may be satisfactorily performed. Further, by virtue of the above-mentioned range, when each of the components are dissolved in an organic solvent, a homogeneous solution may be more reliably obtained and the storage stability of the resist composition becomes satisfactory.

<<Component (D)>>

The resist composition of the present embodiment may further include a basic component (component (D)) which does not fall under the definition of the component (D0). The component (D) functions as an acid diffusion control agent, i.e., a quencher which traps the acid generated in the resist composition upon exposure.

Examples of the component (D) include a photodegradable base (D1) other than the component (D0) (hereafter, referred to as "component (D1)") which is decomposed upon exposure and then loses the ability of controlling of acid diffusion, and a nitrogen-containing organic compound (D2) (hereafter, referred to as "component (D2)") which does not fall under the definition of components (D0) and (D1).

When a resist pattern is formed using a resist composition containing the component (D), the contrast between exposed portions and unexposed portions of the resist film is further improved.

—Component (D1)

The component (D1) is not particularly limited, as long as it does not fall under the definition of component (D0), and it is decomposed upon exposure and then loses the ability of controlling of acid diffusion. As the component (D1), at least one compound selected from the group consisting of a compound represented by general formula (d1-1) shown below (hereafter, referred to as "component (d1-1)"), a compound represented by general formula (d1-2) shown below (hereafter, referred to as "component (d1-2)") and a compound represented by general formula (d1-3) shown below (hereafter, referred to as "component (d1-3)") is preferably used.

At exposed portions of the resist film, the components (d1-1) to (d1-3) are decomposed and then lose the ability of controlling of acid diffusion (i.e., basicity), and therefore the components (d1-1) to (d1-3) cannot function as a quencher, whereas at unexposed portions of the resist film, the components (d1-1) to (d1-3) functions as a quencher.

[Chemical Formula 71]

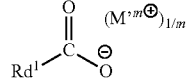

(d1-1)

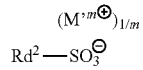

(d1-2)

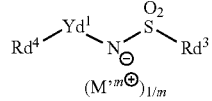

(d1-3)

In the formulae, $Rd^1$ to $Rd^4$ represent a cyclic group which may have a substituent, a chain-like alkyl group which may have a substituent or a chain-like alkenyl group which may have a substituent, provided that, the carbon atom adjacent to the sulfur atom within the $Rd^2$ in general formula (d1-2) has no fluorine atom bonded thereto; $Yd^1$ represents a single bond or a divalent linking group; m represents an integer of 1 or more, and each $M'^{m+}$ independently represents an onium cation having a valency of m.

{Component (d1-1)}

—Anion Moiety

In formula (d1-1), $Rd^1$ represents a cyclic group which may have a substituent, a chain-like alkyl group which may have a substituent or a chain-like alkenyl group which may have a substituent, and is the same groups as those defined above for $R^{101}$ in the aforementioned formula (b-1).

Among these, as the group for $Rd^1$, an aromatic hydrocarbon group which may have a substituent, an aliphatic cyclic group which may have a substituent and a chain-like alkyl group which may have a substituent are preferable. Examples of the substituent for these groups include a hydroxy group, an oxo group, an alkyl group, an aryl group, a fluorine atom, a fluorinated alkyl group, a lactone-containing cyclic group represented by any one of the aforementioned formulae (a2-r-1) to (a2-r-7), an ether bond, an ester bond, and a combination thereof. In the case where an ether bond or an ester bond is included as the substituent, the substituent may be bonded via an alkylene group, and a linking group represented by any one of the aforementioned formulae (y-a1-1) to (y-a1-5) is preferable as the substituent.

Preferable examples of the aromatic hydrocarbon group include a phenyl group, a naphthyl group, and a polycyclic structure (for example, a polycyclic structure formed of a ring structure having a bicyclooctane skeleton and a ring structure other than the bicyclooctane skeleton) containing a bicyclooctane skeleton.

Examples of the aliphatic cyclic group include groups in which one or more hydrogen atoms have been removed from a polycycloalkane such as adamantane, norbornane, isobornane, tricyclodecane or tetracyclododecane.

The chain-like alkyl group preferably has 1 to 10 carbon atoms, and specific examples thereof include a linear alkyl group such as a methyl group, an ethyl group, a propyl group, a butyl group, a pentyl group, a hexyl group, a heptyl group, an octyl group, a nonyl or a decyl group, and a branched alkyl group such as a 1-methylethyl group, a 1-methylpropyl group, a 2-methylpropyl group, a 1-methylbutyl group, a 2-methylbutyl group, a 3-methylbutyl group, a 1-ethylbutyl group, a 2-ethylbutyl group, a 1-methylpentyl group, a 2-methylpentyl group, a 3-methylpentyl group or a 4-methylpentyl group.

In the case where the chain-like alkyl group is a fluorinated alkyl group having a fluorine atom or a fluorinated alkyl group, the fluorinated alkyl group preferably has 1 to 11 carbon atoms, more preferably 1 to 8 carbon atoms, and still more preferably 1 to 4 carbon atoms. The fluorinated alkyl group may contain an atom other than fluorine. Examples of the atom other than fluorine include an oxygen atom, a sulfur atom and a nitrogen atom.

As $Rd^1$, a fluorinated alkyl group in which part or all of the hydrogen atoms constituting a linear alkyl group have been substituted with fluorine atom(s) is preferable, and a fluorinated alkyl group in which all of the hydrogen atoms constituting a linear alkyl group have been substituted with fluorine atoms (i.e., a linear perfluoroalkyl group) is particularly desirable.

Specific examples of preferable anion moieties for the component (d1-1) are shown below.

[Chemical Formula 72]

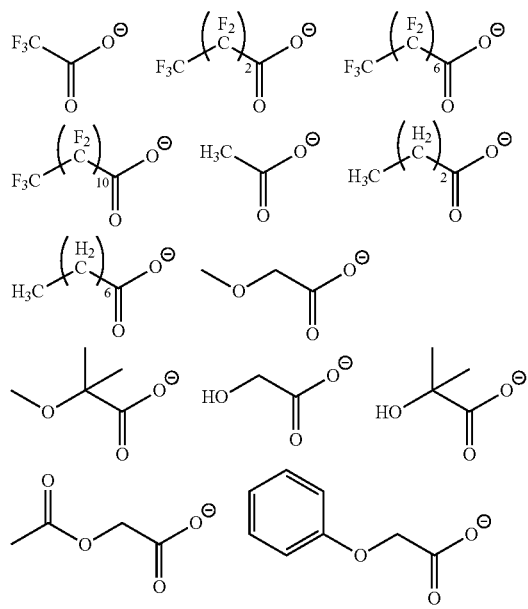

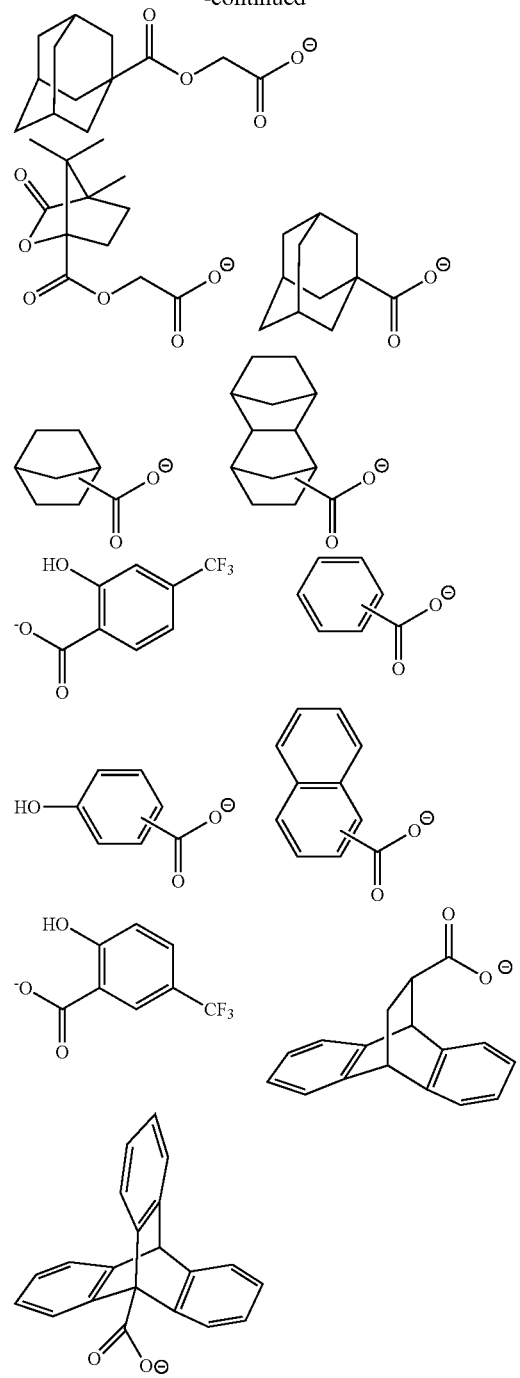

—Cation Moiety

In formula (d1-1), $M'^{m+}$ represents an m-valent organic cation.

Preferable examples of the organic cation for $M'^{m+}$ include the same cation moieties as those represented by the aforementioned general formulae (ca-1) to (ca-5). Among these examples, a cation represented by general formula (ca-1) is preferable.

As the component (d1-1), one kind of compound may be used, or two or more kinds of compounds may be used in combination.

{Component (d1-2)}
—Anion Moiety

In formula (d1-2), $Rd^2$ represents a cyclic group which may have a substituent, a chain-like alkyl group which may have a substituent or a chain-like alkenyl group which may have a substituent, and is the same groups as those defined above for $R^{101}$ in the aforementioned formula (b-1).

However, the carbon atom adjacent to the sulfur atom within the $Rd^2$ has no fluorine atom bonded thereto. As a result, the component (d1-2) becomes a suitably weakly acidic anion, and the quenching ability of the component (D1) is improved.

As $Rd^2$, a chain-like alkyl group which may have a substituent or an aliphatic cyclic group which may have a substituent is preferable. The chain-like alkyl group preferably has 1 to 10 carbon atoms, and more preferably 3 to 10 carbon atoms. As the aliphatic cyclic group, a group in which one or more hydrogen atoms have been removed from adamantane, norbornane, isobornane, tricyclodecane, tetracyclododecane or camphor (which may have a substituent) is more preferable.

The hydrocarbon group for $Rd^2$ may have a substituent. As the substituent, the same groups as those described above for substituting the hydrocarbon group (e.g., aromatic hydrocarbon group, aliphatic cyclic group, chain-like alkyl group) for $Rd^1$ in the formula (d1-1) can be mentioned.

Specific examples of preferable anion moieties for the component (d1-2) are shown below.

[Chemical Formula 73]

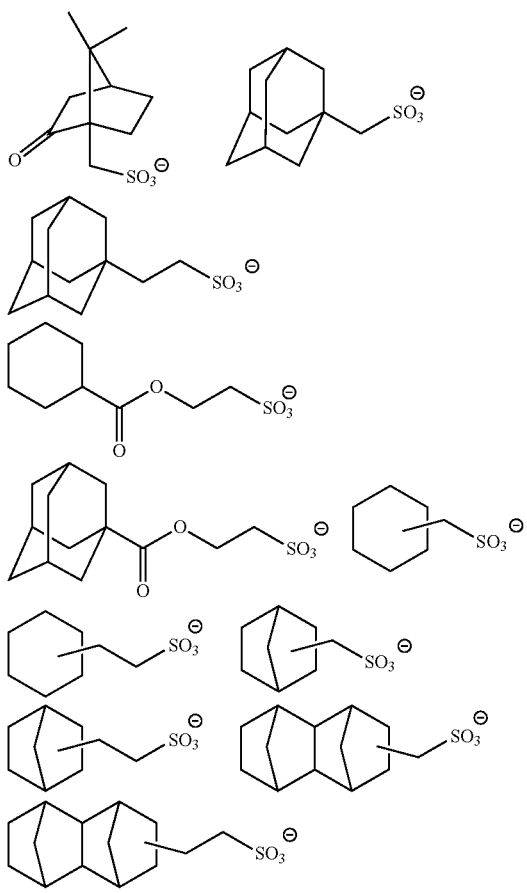

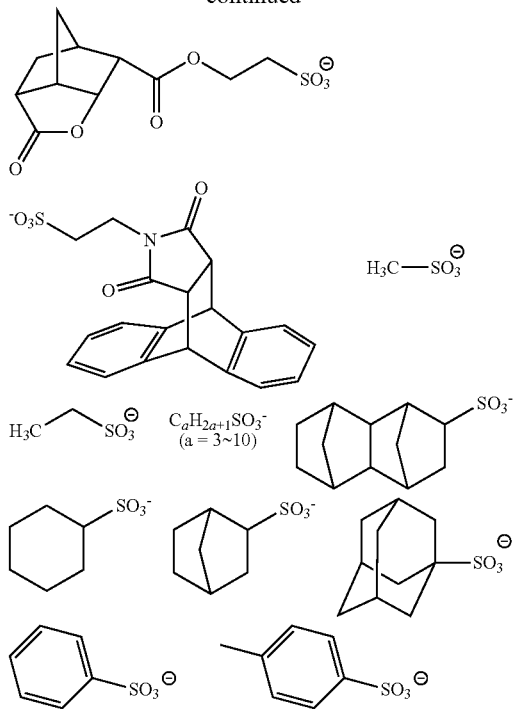

—Cation Moiety

In formula (d1-2), $M'^{m+}$ is an m-valent onium cation, and is the same as defined for $M'^{m+}$ in the aforementioned formula (d1-1).

As the component (d1-2), one type of compound may be used, or two or more types of compounds may be used in combination.

{Component (d1-3)}
—Anion Moiety

In formula (d1-3), $Rd^3$ represents a cyclic group which may have a substituent, a chain-like alkyl group which may have a substituent or a chain-like alkenyl group which may have a substituent, and is the same groups as those defined above for $R^{101}$ in the aforementioned formula (b-1), and a cyclic group containing a fluorine atom, a chain-like alkyl group or a chain-like alkenyl group is preferable. Among these, a fluorinated alkyl group is preferable, and more preferably the same fluorinated alkyl groups as those described above for $Rd^1$.

In formula (d1-3), $Rd^4$ represents a cyclic group which may have a substituent, a chain-like alkyl group which may have a substituent or a chain-like alkenyl group which may have a substituent, and is the same groups as those defined above for $R^{101}$ in the aforementioned formula (b-1).

Among these, an alkyl group which may have substituent, an alkoxy group which may have substituent, an alkenyl group which may have substituent or a cyclic group which may have substituent is preferable.

The alkyl group for $Rd^4$ is preferably a linear or branched alkyl group of 1 to 5 carbon atoms, and specific examples include a methyl group, an ethyl group, a propyl group, an isopropyl group, an n-butyl group, an isobutyl group, a tert-butyl group, a pentyl group, an isopentyl group, and a neopentyl group. Part of the hydrogen atoms within the alkyl group for $Rd^4$ may be substituted with a hydroxy group, a cyano group or the like.

The alkoxy group for $Rd^4$ is preferably an alkoxy group of 1 to 5 carbon atoms, and specific examples thereof include a methoxy group, an ethoxy group, an n-propoxy group, an iso-propoxy group, an n-butoxy group and a tert-butoxy group. Among these, a methoxy group and an ethoxy group are preferable.

As the alkenyl group for $Rd^4$, the same groups as those described above for $R^{101}$ in the aforementioned formula (b-1) may be mentioned, and a vinyl group, a propenyl group (an allyl group), a 1-methylpropenyl group and a 2-methylpropenyl group are preferable. These groups may have an alkyl group of 1 to 5 carbon atoms or a halogenated alkyl group of 1 to 5 carbon atoms as a substituent.

As the cyclic group for $Rd^4$, the same groups as those described above for $R^{101}$ in the aforementioned formula (b-1) may be mentioned. Among these, as the cyclic group, an alicyclic group (e.g., a group in which one or more hydrogen atoms have been removed from a cycloalkane such as cyclopentane, cyclohexane, adamantane, norbornane, isobornane, tricyclodecane or tetracyclododecane) or an aromatic group (e.g., a phenyl group or a naphthyl group) is preferable. When $Rd^4$ is an alicyclic group, the resist composition can be satisfactorily dissolved in an organic solvent, thereby improving the lithographic properties.

In formula (d1-3), $Yd^1$ represents a single bond or a divalent linking group. The divalent linking group for $Yd^1$ is not particularly limited, and examples thereof include a divalent hydrocarbon group (aliphatic hydrocarbon group, or aromatic hydrocarbon group) which may have a substituent and a divalent linking group containing a hetero atom. The divalent linking groups are the same as defined for the divalent hydrocarbon group which may have a substituent and the divalent linking group containing a hetero atom explained above as the divalent linking group for $Ya^{x1}$ in the aforementioned formula (a10-1).

As $Yd^1$, a carbonyl group, an ester bond, an amide bond, an alkylene group or a combination of these is preferable. As the alkylene group, a linear or branched alkylene group is more preferable, and a methylene group or an ethylene group is still more preferable.

Specific examples of preferable anion moieties for the component (d1-3) are shown below.

[Chemical Formula 74]

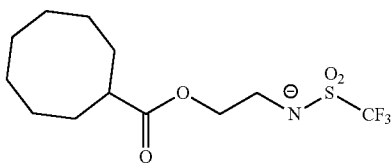

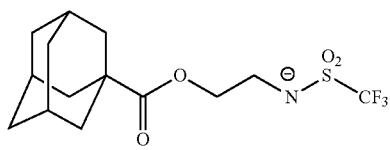

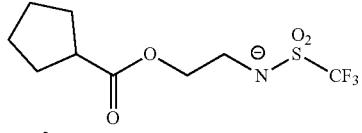

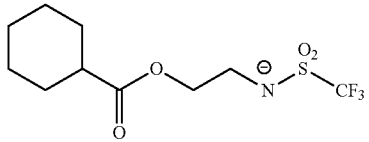

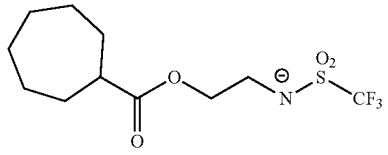

-continued

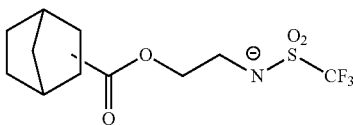

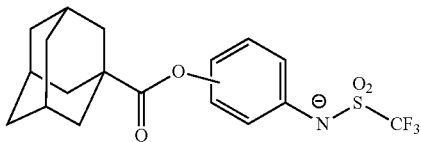

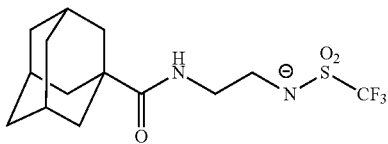

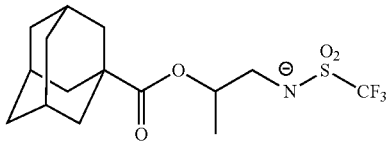

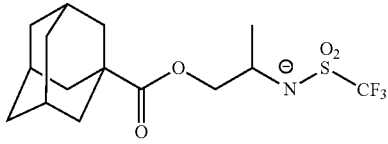

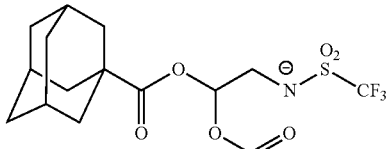

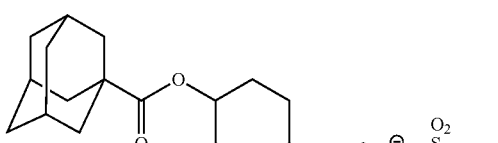

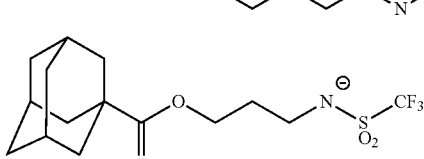

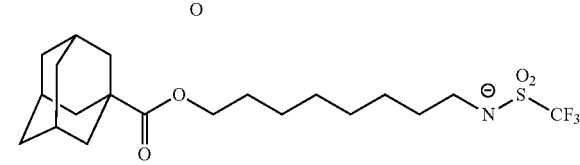

145
-continued

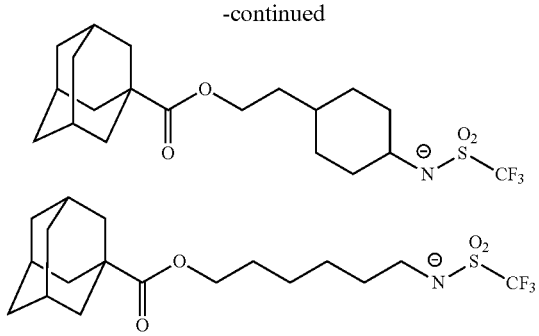

[Chemical Formula 75]

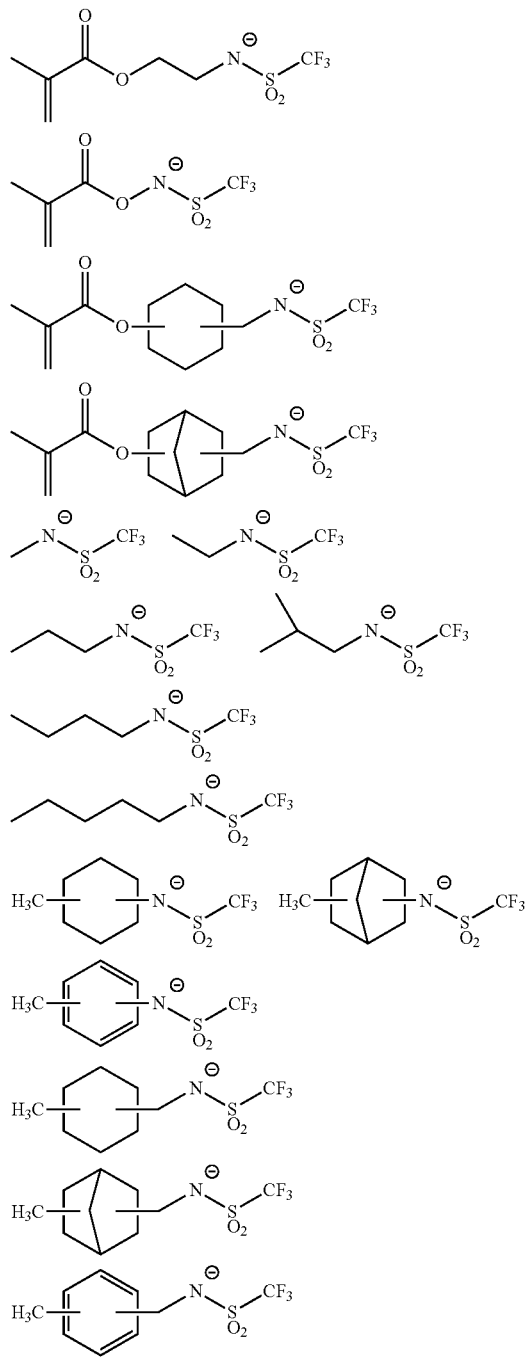

146
-continued

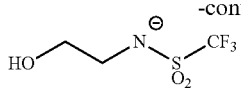

—Cation Moiety

In formula (d1-3), $M'^{m+}$ is an m-valent onium cation, and is the same as defined for $M'^{m+}$ in the aforementioned formula (d1-1).

As the component (d1-3), one type of compound may be used, or two or more types of compounds may be used in combination.

As the component (D1), one type of the aforementioned components (d1-1) to (d1-3), or at least two types of the aforementioned components (d1-1) to (d1-3) can be used in combination.

In the case where the resist composition contains the component (D1), the amount of the component (D1) relative to 100 parts by weight of the component (A) is preferably within a range from 0.5 to 35 parts by weight, more preferably from 1 to 25 parts by weight, still more preferably from 2 to 20 parts by weight, and still more preferably 3 to 15 parts by weight.

When the amount of the component (D1) is at least as large as the lower limit of the above-mentioned range, excellent lithographic properties and excellent resist pattern shape may be more reliably obtained. On the other hand, when the amount of the component (D1) is no more than the upper limit of the above-mentioned preferable range, a good balance may be achieved with the other structural units, and the lithography properties may be improved.

Production Method of Component (D1):

The production methods of the components (d1-1) and (d1-2) are not particularly limited, and the components (d1-1) and (d1-2) can be produced by conventional methods. Further, the production method of the component (d1-3) is not particularly limited, and the component (d1-3) can be produced in the same manner as disclosed in US2012-0149916.

—Component (D2)

The component (D2) is a basic component, and is a nitrogen-containing organic compound which acts as an acid diffusion control agent in the resist composition.

The component (D2) is not particularly limited as long as it acts as an acid diffusion control agent and does not fall under the definition of the component (D0) and the component (D1). Examples thereof include aliphatic amines and aromatic amines.

Among the aliphatic amines, secondary aliphatic amines and tertiary aliphatic amines are preferable.

An aliphatic amine is an amine having one or more aliphatic groups, and the aliphatic groups preferably have 1 to 12 carbon atoms.

Examples of these aliphatic amines include amines in which at least one hydrogen atom of ammonia ($NH_3$) has been substituted with an alkyl group or hydroxyalkyl group of no more than 12 carbon atoms (i.e., alkylamines or alkylalcoholamines), and cyclic amines.

Specific examples of alkylamines and alkylalcoholamines include monoalkylamines such as n-hexylamine, n-heptylamine, n-octylamine, n-nonylamine, and n-decylamine; dialkylamines such as diethylamine, di-n-propylamine, di-n-heptylamine, di-n-octylamine, and dicyclohexylamine; trialkylamines such as trimethylamine, triethylamine, tri-n-propylamine, tri-n-butylamine, tri-n-hexylamine, tri-n-pentylamine, tri-n-heptylamine, tri-n-octylamine, tri-n- nonylamine, tri-n-decylamine, and tri-n-dodecylamine; and alkyl alcohol amines such as diethanolamine, triethanolamine, diisopropanolamine, triisopropanolamine, di-n-octanolamine, and tri-n-octanolamine. Among these, trialkylamines of 5 to 10 carbon atoms are preferable, and tri-n-pentylamine and tri-n-octylamine are particularly desirable.

Examples of the cyclic amine include heterocyclic compounds containing a nitrogen atom as a hetero atom. The heterocyclic compound may be a monocyclic compound (aliphatic monocyclic amine), or a polycyclic compound (aliphatic polycyclic amine).

Specific examples of the aliphatic monocyclic amine include piperidine, and piperazine. The aliphatic polycyclic amine preferably has 6 to 10 carbon atoms, and specific examples thereof include 1,5-diazabicyclo[4.3.0]-5-nonene, 1,8-diazabicyclo[5.4.0]-7-undecene, hexamethylenetetramine, and 1,4-diazabicyclo[2.2.2]octane.

Examples of other aliphatic amines include tris(2-methoxymethoxyethyl)amine, tris{2-(2-methoxyethoxy)ethyl}amine, tris{2-(2-methoxyethoxymethoxy)ethyl}amine, tris{2-(1-methoxyethoxy)ethyl}amine, tris{2-(1-ethoxyethoxy)ethyl}amine, tris{2-(1-ethoxypropoxy)ethyl}amine, tris [2-{2-(2-hydroxyethoxy)ethoxy}ethyl] amine and triethanolamine triacetate, and triethanolamine triacetate is preferable.

Examples of aromatic amines include 4-dimethylaminopyridine, pyrrole, indole, pyrazole, imidazole and derivatives thereof, as well as tribenzylamine, aniline compound and N-tert-butoxycarbonylpyrrolidine.

As the component (D2), one kind of compound may be used, or two or more kinds of compounds may be used in combination. Among the above examples, as the component (D2), an aromatic amine is preferable, and an aniline compound is more preferable. Examples of the aniline compound include 2,6-diisopropylaniline, N, N-dimethylaniline, N, N-dibutylaniline, and N, N-dihexylaniline.

When the resist composition contains the component (D2), the amount of the component (D2) is typically used in an amount within a range from 0.01 to 5 parts by weight, relative to 100 parts by weight of the component (A). When the amount of the component (D2) is within the above-mentioned preferable range, a good balance may be achieved with the other structural units, and the lithography properties may be improved.

<<At Least One Compound (E) Selected from the Group Consisting of an Organic Carboxylic Acid, or a Phosphorus Oxo Acid or Derivative Thereof>>

In the resist composition of the present embodiment, for preventing any deterioration in sensitivity, and improving the resist pattern shape and the post exposure stability of the latent image formed by the pattern-wise exposure of the resist layer, at least one compound (E) (hereafter referred to as the component (E)) selected from the group consisting of an organic carboxylic acid, or a phosphorus oxo acid or derivative thereof may be added.

Examples of suitable organic carboxylic acids include acetic acid, malonic acid, citric acid, malic acid, succinic acid, benzoic acid, and salicylic acid.

Examples of phosphorus oxo acids include phosphoric acid, phosphonic acid and phosphinic acid. Among these, phosphonic acid is particularly desirable.

Examples of oxo acid derivatives include esters in which a hydrogen atom within the above-mentioned oxo acids is substituted with a hydrocarbon group. Examples of the hydrocarbon group include an alkyl group of 1 to 5 carbon atoms and an aryl group of 6 to 15 carbon atoms.

Examples of phosphoric acid derivatives include phosphoric acid esters such as di-n-butyl phosphate and diphenyl phosphate.

Examples of phosphonic acid derivatives include phosphonic acid esters such as dimethyl phosphonate, di-n-butyl phosphonate, phenylphosphonic acid, diphenyl phosphonate and dibenzyl phosphonate.

Examples of phosphinic acid derivatives include phosphinic acid esters and phenylphosphinic acid.

In the resist composition of the present embodiment, as the component (E), one kind of compound may be used, or two or more kinds of compounds may be used in combination.

When the resist composition contains the component (E), the amount of the component (E) is typically used in an amount within a range from 0.01 to 5 parts by weight, relative to 100 parts by weight of the component (A).

<<Fluorine Additive (F)>>

In the present embodiment, the resist composition may further include a fluorine additive (hereafter, referred to as "component (F)") for imparting water repellency to the resist film, or improving lithography properties.

As the component (F), for example, a fluorine-containing polymeric compound described in Japanese Unexamined Patent Application, First Publication No. 2010-002870, Japanese Unexamined Patent Application, First Publication No. 2010-032994, Japanese Unexamined Patent Application, First Publication No. 2010-277043, Japanese Unexamined Patent Application, First Publication No. 2011-13569, and Japanese Unexamined Patent Application, First Publication No. 2011-128226 can be used.

Specific examples of the component (F) include polymers having a structural unit (f1) represented by general formula (f1-1) shown below. As the polymer, a polymer (homopolymer) consisting of a structural unit (f1) represented by formula (f1-1) shown below; a copolymer of the structural unit (f1) and the aforementioned structural unit (a1); and a copolymer of the structural unit (f1), a structural unit derived from acrylic acid or methacrylic acid and the aforementioned structural unit (a1) are preferable. As the structural unit (a1) to be copolymerized with the structural unit (f1), a structural unit derived from 1-ethyl-1-cyclooctyl (meth) acrylate or a structural unit derived from 1-methyl-1-adamantyl (meth)acrylate is preferable.

[Chemical Formula 76]

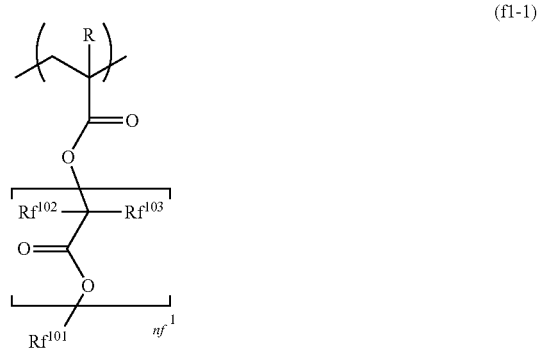

(f1-1)

In the formula, R is the same as defined above; $Rf^{102}$ and $Rf^{103}$ each independently represents a hydrogen atom, a halogen atom, an alkyl group of 1 to 5 carbon atoms, or a halogenated alkyl group of 1 to 5 carbon atoms, provided that $Rf^{102}$ and $Rf^{103}$ may be the same or different; $nf^1$ represents an integer of 0 to 5; and $Rf^{101}$ represents an organic group containing a fluorine atom.

In formula (f1-1), R bonded to the carbon atom on the α-position is the same as defined above. As R, a hydrogen atom or a methyl group is preferable.

In formula (f1-1), as the halogen atom for $Rf^{102}$ and $Rf^{03}$, a fluorine atom is preferable. Examples of the alkyl group of 1 to 5 carbon atoms for $Rf^{102}$ and $Rf^{103}$ include the same alkyl group of 1 to 5 carbon atoms as those described above for R, and a methyl group or an ethyl group is preferable. Specific examples of the halogenated alkyl group of 1 to 5 carbon atoms represented by $Rf^{102}$ or $Rf^{103}$ include groups in which part or all of the hydrogen atoms of the aforementioned alkyl groups of 1 to 5 carbon atoms have been substituted with halogen atoms. As the halogen atom, a fluorine atom is most preferable. Among these, as $Rf^{102}$ and $Rf^{103}$, a hydrogen atom, a fluorine atom or an alkyl group of 1 to 5 carbon atoms is preferable, and a hydrogen atom, a fluorine atom, a methyl group or an ethyl group is more preferable. In formula (f1-1), $nf^1$ represents an integer of 0 to 5, preferably an integer of 0 to 3, and more preferably 1 or 2.

In formula (f1-1), $Rf^{101}$ represents an organic group containing a fluorine atom, and is preferably a hydrocarbon group containing a fluorine atom.

The hydrocarbon group containing a fluorine atom may be linear, branched or cyclic, and preferably has 1 to 20 carbon atoms, more preferably 1 to 15 carbon atoms, and most preferably 1 to 10 carbon atoms.

It is preferable that the hydrocarbon group having a fluorine atom has 25% or more of the hydrogen atoms within the hydrocarbon group fluorinated, more preferably 50% or more, and most preferably 60% or more, as the hydrophobicity of the resist film during immersion exposure is enhanced.

Among these, as $Rf^{101}$, a fluorinated hydrocarbon group of 1 to 6 carbon atoms is preferable, and a trifluoromethyl group, —$CH_2$—$CF_3$, —$CH_2$—$CF_2$—$CF_3$, —$CH(CF_3)_2$, —$CH_2$—$CH_2$—$CF_3$, and —$CH_2$—$CH_2$—$CF_2$—$CF_2$—$CF_2$—$CF_3$ are most preferable.

The weight average molecular weight (Mw) (the polystyrene equivalent value determined by gel permeation chromatography) of the component (F) is preferably 1,000 to 50,000, more preferably 5,000 to 40,000, and most preferably 10,000 to 30,000. When the weight average molecular weight (Mw) is no more than the upper limit of the above-mentioned range, the resist may exhibit satisfactory solubility in a resist solvent. On the other hand, when the weight average molecular weight (Mw) is at least as large as the lower limit of the above-mentioned range, the water repellency of the resist film may become satisfactory.

Further, the dispersity (Mw/Mn) of the component (F) is preferably 1.0 to 5.0, more preferably 1.0 to 3.0, and most preferably 1.0 to 2.5.

In the resist composition of the present embodiment, as the component (F), one kind of compound may be used, or two or more kinds of compounds may be used in combination.

When the resist composition contains the component (F), the component (F) is used in an amount within a range from 0.5 to 10 parts by weight, relative to 100 parts by weight of the component (A).

<<Organic Solvent (S)>>

The resist composition of the present embodiment may be prepared by dissolving the resist materials for the resist composition in an organic solvent (hereafter, referred to as "component (S)").

The component (S) may be any organic solvent which can dissolve the respective components to give a homogeneous solution, and any organic solvent can be appropriately selected from those which have been conventionally known as solvents for a chemically amplified resist composition.

Examples thereof include lactones such as γ-butyrolactone; ketones such as acetone, methyl ethyl ketone, cyclohexanone, methyl-n-pentyl ketone, methyl isopentyl ketone, and 2-heptanone; polyhydric alcohols, such as ethylene glycol, diethylene glycol, propylene glycol and dipropylene glycol; compounds having an ester bond, such as ethylene glycol monoacetate, diethylene glycol monoacetate, propylene glycol monoacetate, and dipropylene glycol monoacetate; polyhydric alcohol derivatives including compounds having an ether bond, such as a monoalkylether (e.g., monomethylether, monoethylether, monopropylether or monobutylether) or monophenylether of any of these polyhydric alcohols or compounds having an ester bond (among these, propylene glycol monomethyl ether acetate (PGMEA) and propylene glycol monomethyl ether (PGME) are preferable); cyclic ethers such as dioxane; esters such as methyl lactate, ethyl lactate (EL), methyl acetate, ethyl acetate, butyl acetate, methyl pyruvate, ethyl pyruvate, methyl methoxypropionate, and ethyl ethoxypropionate; aromatic organic solvents such as anisole, ethylbenzylether, cresylmethylether, diphenylether, dibenzylether, phenetole, butylphenylether, ethylbenzene, diethylbenzene, pentylbenzene, isopropylbenzene, toluene, xylene, cymene and mesitylene; and dimethylsulfoxide (DMSO).

In the resist composition of the present embodiment, as the component (S), one kind of solvent may be used, or two or more kinds of compounds may be used as a mixed solvent. Among these examples, PGMEA, PGME, γ-butyrolactone, EL and cyclohexanone are preferable.

Further, as the component (S), a mixed solvent obtained by mixing PGMEA with a polar solvent is preferable. The mixing ratio (weight ratio) of the mixed solvent can be appropriately determined, taking into consideration the compatibility of the PGMEA with the polar solvent, but is preferably in the range of 1:9 to 9:1, more preferably from 2:8 to 8:2.

Specifically, when EL or cyclohexanone is mixed as the polar solvent, the PGMEA:EL or cyclohexanone weight ratio is preferably from 1:9 to 9:1, and more preferably from 2:8 to 8:2. Alternatively, when PGME is mixed as the polar solvent, the PGMEA:PGME weight ratio is preferably from 1:9 to 9:1, more preferably from 2:8 to 8:2, and still more preferably 3:7 to 7:3. Furthermore, a mixed solvent of PGMEA, PGME and cyclohexanone is also preferable.

Further, as the component (S), a mixed solvent of at least one of PGMEA and EL with γ-butyrolactone is also preferable. The mixing ratio (former:latter) of such a mixed solvent is preferably from 70:30 to 95:5.

The amount of the component (S) is not particularly limited, and is appropriately adjusted to a concentration which enables coating of a coating solution to a substrate. In general, the component (S) is used in an amount such that the solid content of the resist composition becomes within the range from 0.1 to 20% by weight, and preferably from 0.2 to 15% by weight.

If desired, other miscible additives can also be added to the resist composition of the present invention. Examples of such miscible additives include additive resins for improving the performance of the resist film, dissolution inhibitors, plasticizers, stabilizers, colorants, halation prevention agents, and dyes.

After dissolving the resist materials in the organic solvent (S), the resist composition of the present embodiment may have impurities or the like removed by using a polyimide porous film, a polyamide-imide porous film, or the like. For example, the resist composition may be subjected to filtration using a filter formed of a polyimide porous membrane, a filter formed of a polyamide-imide porous film, or a filter formed of a polyimide porous membrane and a polyamide-imide porous film. Examples of the polyimide porous membrane and the polyamide-imide porous film include those described in Japanese Unexamined Patent Application, First Publication No. 2016-155121.

As described above, the resist composition of the present embodiment includes a polymeric compound (A10) having a structural unit (a0) and a component (D0). The structural unit (a0) has an acid dissociable group represented by "—$C^t(R^{11})(R^{12})(R^{13})$" in formula (a0-1). In the acid dissociable group, the α-position of the tertiary carbon atom $C^t$ is a carbon atom constituting a carbon-carbon unsaturated bond. Therefore, the deprotection of the acid dissociable group by acid may proceed more reliably. Further, since the anion moiety of the component (D0) has plurality of hydroxy groups, the resist composition has high affinity for a developing solution, and the solubility of the exposed portions in a developing solution is improved. By the above synergetic effects, the resist composition according to the present embodiment may exhibit improved sensitivity and lithography properties, and is capable of forming a resist pattern having a high rectangularity.

(Method of Forming a Resist Pattern)

The method of forming a resist pattern according to the second aspect of the present invention includes: using a resist composition according to the first aspect to form a resist film on a substrate; exposing the resist film; and developing the exposed resist film to form a resist pattern.

The method for forming a resist pattern according to the present embodiment can be performed, for example, as follows.

Firstly, a resist composition of the first aspect is applied to a substrate using a spinner or the like, and a bake treatment (post applied bake (PAB)) is conducted at a temperature of 80 to 150° C. for 40 to 120 seconds, preferably 60 to 90 seconds, to form a resist film.

Following selective exposure of the thus formed resist film, either by exposure through a mask having a predetermined pattern formed thereon (mask pattern) using an exposure apparatus such an electron beam lithography apparatus or an EUV exposure apparatus, or by patterning via direct irradiation with an electron beam without using a mask pattern, baking treatment (post exposure baking (PEB)) is conducted under temperature conditions of 80 to 150° C. for 40 to 120 seconds, and preferably 60 to 90 seconds.

Next, the resist film is subjected to a developing treatment. The developing treatment is conducted using an alkali developing solution in the case of an alkali developing process, and a developing solution containing an organic solvent (organic developing solution) in the case of a solvent developing process.

After the developing treatment, it is preferable to conduct a rinse treatment. The rinse treatment is preferably conducted using pure water in the case of an alkali developing process, and a rinse solution containing an organic solvent in the case of a solvent developing process.

In the case of a solvent developing process, after the developing treatment or the rinsing, the developing solution or the rinse liquid remaining on the pattern can be removed by a treatment using a supercritical fluid.

After the developing treatment or the rinse treatment, drying is conducted. If desired, bake treatment (post bake) can be conducted following the developing.

In this manner, a resist pattern can be formed.

The substrate is not specifically limited and a conventionally known substrate can be used. For example, substrates for electronic components, and such substrates having wiring patterns formed thereon can be used. Specific examples of the material of the substrate include metals such as silicon wafer, copper, chromium, iron and aluminum; and glass. Suitable materials for the wiring pattern include copper, aluminum, nickel, and gold.

Further, as the substrate, any one of the above-mentioned substrates provided with an inorganic and/or organic film on the surface thereof may be used. As the inorganic film, an inorganic antireflection film (inorganic BARC) can be used. As the organic film, an organic antireflection film (organic BARC) and an organic film such as a lower-layer organic film used in a multilayer resist method can be used.

Here, a "multilayer resist method" is method in which at least one layer of an organic film (lower-layer organic film) and at least one layer of a resist film (upper resist film) are provided on a substrate, and a resist pattern formed on the upper resist film is used as a mask to conduct patterning of the lower-layer organic film. This method is considered as being capable of forming a pattern with a high aspect ratio. More specifically, in the multilayer resist method, a desired thickness can be ensured by the lower-layer organic film, and as a result, the thickness of the resist film can be reduced, and an extremely fine pattern with a high aspect ratio can be formed.

The multilayer resist method is broadly classified into a method in which a double-layer structure consisting of an upper-layer resist film and a lower-layer organic film is formed (double-layer resist method), and a method in which a multilayer structure having at least three layers consisting of an upper-layer resist film, a lower-layer organic film and at least one intermediate layer (thin metal film or the like) provided between the upper-layer resist film and the lower-layer organic film (triple-layer resist method).

The wavelength to be used for exposure is not particularly limited and the exposure can be conducted using radiation such as ArF excimer laser, KrF excimer laser, $F_2$ excimer laser, extreme ultraviolet rays (EUV), vacuum ultraviolet rays (VUV), electron beam (EB), X-rays, and soft X-rays. The resist composition of the present embodiment is effective to KrF excimer laser, ArF excimer laser, EB and EUV, and more effective to ArF excimer laser, EB and EUV, and most effective to EB and EUV. That is, the method of forming a resist pattern according to the present embodiment is effective in the case where the step of exposing the resist film includes exposing the resist film with extreme ultraviolet rays (EUV) or electron beam (EB).

The exposure of the resist film can be either a general exposure (dry exposure) conducted in air or an inert gas such as nitrogen, or immersion exposure (immersion lithography).

In immersion lithography, the region between the resist film and the lens at the lowermost point of the exposure apparatus is pre-filled with a solvent (immersion medium) that has a larger refractive index than the refractive index of air, and the exposure (immersion exposure) is conducted in this state.

The immersion medium preferably exhibits a refractive index larger than the refractive index of air but smaller than the refractive index of the resist film to be exposed. The refractive index of the immersion medium is not particularly limited as long as it satisfies the above-mentioned requirements.

Examples of this immersion medium which exhibits a refractive index that is larger than the refractive index of air but smaller than the refractive index of the resist film include water, fluorine-based inert liquids, silicon-based solvents and hydrocarbon-based solvents.

Specific examples of the fluorine-based inert liquids include liquids containing a fluorine-based compound such as $C_3HCl_2F_5$, $C_4F_9OCH_3$, $C_4F_9OC_2H_5$ or $C_5H_3F_7$ as the main component, which have a boiling point within a range from 70 to 180° C. and preferably from 80 to 160° C. A fluorine-based inert liquid having a boiling point within the above-mentioned range is advantageous in that the removal of the immersion medium after the exposure can be conducted by a simple method. As a fluorine-based inert liquid, a perfluoroalkyl compound in which all of the hydrogen atoms of the alkyl group are substituted with fluorine atoms is particularly desirable. Examples of these perfluoroalkyl compounds include perfluoroalkylether compounds and perfluoroalkylamine compounds.

Specifically, one example of a suitable perfluoroalkylether compound is perfluoro(2-butyl-tetrahydrofuran) (boiling point 102° C.), and an example of a suitable perfluoroalkylamine compound is perfluorotributylamine (boiling point 174° C.).

As the immersion medium, water is preferable in terms of cost, safety, environment and versatility.

As an example of the alkali developing solution used in an alkali developing process, a 0.1 to 10% by weight aqueous solution of tetramethylammonium hydroxide (TMAH) can be given.

As the organic solvent contained in the organic developing solution used in a solvent developing process, any of the conventional organic solvents can be used which are capable of dissolving the component (A) (prior to exposure). Specific examples of the organic solvent include polar solvents such as ketone solvents, ester solvents, alcohol solvents, nitrile solvents, amide solvents and ether solvents, and hydrocarbon solvents.

A ketone solvent is an organic solvent containing C—C(=O)—C within the structure thereof. An ester solvent is an organic solvent containing C—C(=O)—O—C within the structure thereof. An alcohol solvent is an organic solvent containing an alcoholic hydroxy group in the structure thereof. An "alcoholic hydroxy group" refers to a hydroxy group bonded to a carbon atom of an aliphatic hydrocarbon group. A nitrile solvent is an organic solvent containing a nitrile group in the structure thereof. An amide solvent is an organic solvent containing an amide group within the structure thereof. An ether solvent is an organic solvent containing C—O—C within the structure thereof.

Some organic solvents have a plurality of the functional groups which characterizes the aforementioned solvents within the structure thereof. In such a case, the organic solvent can be classified as any type of the solvent having the characteristic functional group. For example, diethylene glycol monomethyl ether may be classified as an alcohol solvent or an ether solvent.

A hydrocarbon solvent consists of a hydrocarbon which may be halogenated, and does not have any substituent other than a halogen atom. As the halogen atom, a fluorine atom is preferable.

As the organic solvent contained in the organic developing solution, among these, a polar solvent is preferable, and ketone solvents, ester solvents and nitrile solvents are preferable.

Examples of ketone solvents include 1-octanone, 2-octanone, 1-nonanone, 2-nonanone, acetone, 4-heptanone, 1-hexanone, 2-hexanone, diisobutyl ketone, cyclohexanone, methylcyclohexanone, phenylacetone, methyl ethyl ketone, methyl isobutyl ketone, acetylacetone, acetonylacetone, ionone, diacetonylalcohol, acetylcarbinol, acetophenone, methyl naphthyl ketone, isophorone, propylenecarbonate, γ-butyrolactone and methyl amyl ketone (2-heptanone). Among these examples, as a ketone solvent, methyl amyl ketone (2-heptanone) is preferable.

Examples of ester solvents include methyl acetate, butyl acetate, ethyl acetate, isopropyl acetate, amyl acetate, isoamyl acetate, ethyl methoxyacetate, ethyl ethoxyacetate, ethylene glycol monoethyl ether acetate, ethylene glycol monopropyl ether acetate, ethylene glycol monobutyl ether acetate, ethylene glycol monophenyl ether acetate, diethylene glycol monomethyl ether acetate, diethylene glycol monopropyl ether acetate, diethylene glycol monoethyl ether acetate, diethylene glycol monophenyl ether acetate, diethylene glycol monobutyl ether acetate, diethylene glycol monoethyl ether acetate, 2-methoxybutyl acetate, 3-methoxybutyl acetate, 4-methoxybutyl acetate, 3-methyl-3-methoxybutyl acetate, 3-ethyl-3-methoxybutyl acetate, propylene glycol monomethyl ether acetate, propylene glycol monoethyl ether acetate, propylene glycol monopropyl ether acetate, 2-ethoxybutyl acetate, 4-ethoxybutyl acetate, 4-propoxybutyl acetate, 2-methoxypentyl acetate, 3-methoxypentyl acetate, 4-methoxypentyl acetate, 2-methyl-3-methoxypentyl acetate, 3-methyl-3-methoxypentyl acetate, 3-methyl-4-methoxypentyl acetate, 4-methyl-4-methoxypentyl acetate, propylene glycol diacetate, methyl formate, ethyl formate, butyl formate, propyl formate, ethyl lactate, butyl lactate, propyl lactate, ethyl carbonate, propyl carbonate, butyl carbonate, methyl pyruvate, ethyl pyruvate, propyl pyruvate, butyl pyruvate, methyl acetoacetate, ethyl acetoacetate, methyl propionate, ethyl propionate, propyl propionate, isopropyl propionate, methyl 2-hydroxypropionate, ethyl 2-hydroxypropionate, methyl-3-methoxypropionate, ethyl-3-methoxypropionate, ethyl-3-ethoxypropionate and propyl-3-methoxypropionate. Among these examples, as an ester solvent, butyl acetate is preferable. Among these examples, as an ester solvent, butyl acetate is preferable.

Examples of nitrile solvents include acetonitrile, propionitrile, valeronitrile, and butyronitrile.

If desired, the organic developing solution may have a conventional additive blended. Examples of the additive include surfactants. The surfactant is not particularly limited, and for example, an ionic or non-ionic fluorine and/or silicon surfactant may be used. As the surfactant, a non-ionic surfactant is preferable, and a non-ionic fluorine surfactant or a non-ionic silicon surfactant is more preferable.

When a surfactant is added, the amount thereof based on the total amount of the organic developing solution is generally 0.001 to 5% by weight, preferably 0.005 to 2% by weight, and more preferably 0.01 to 0.5% by weight.

The developing treatment may be performed by a conventional developing method. Examples thereof include a method in which the substrate is immersed in the developing solution for a predetermined time (a dip method), a method in which the developing solution is cast up on the surface of the substrate by surface tension and maintained for a predetermined period (a puddle method), a method in which the developing solution is sprayed onto the surface of the substrate (spray method), and a method in which the developing solution is continuously ejected from a developing solution ejecting nozzle while scanning at a constant rate to apply the developing solution to the substrate while rotating the substrate at a constant rate (dynamic dispense method).

As the organic solvent contained in the rinse liquid used in the rinse treatment after the developing treatment in the case of a solvent developing process, any of the aforementioned organic solvents contained in the organic developing solution can be used which hardly dissolves the resist pattern. In general, at least one solvent selected from the group consisting of hydrocarbon solvents, ketone solvents, ester solvents, alcohol solvents, amide solvents and ether solvents is used. Among these, at least one solvent selected from the group consisting of hydrocarbon solvents, ketone solvents, ester solvents, alcohol solvents and amide solvents is preferable, more preferably at least one solvent selected from the group consisting of alcohol solvents and ester solvents, and an alcohol solvent is particularly desirable.

The alcohol solvent used for the rinse liquid is preferably a monohydric alcohol of 6 to 8 carbon atoms, and the monohydric alcohol may be linear, branched or cyclic. Specific examples thereof include 1-hexanol, 1-heptanol, 1-octanol, 2-hexanol, 2-heptanol, 2-octanol, 3-hexanol, 3-heptanol, 3-octanol, 4-octanol and benzyl alcohol. Among these, 1-hexanol, 2-heptanol and 2-hexanol are preferable, and 1 hexanol and 2-hexanol are more preferable.

As the organic solvent, one kind of solvent may be used alone, or two or more kinds of solvents may be used in combination. Further, an organic solvent other than the aforementioned examples or water may be mixed together. However, in consideration of the development characteristics, the amount of water within the rinse liquid, based on the total amount of the rinse liquid is preferably 30% by weight or less, more preferably 10% by weight or less, still more preferably 5% by weight or less, and most preferably 3% by weight or less.

If desired, the rinse solution may have a conventional additive blended. Examples of the additive include surfactants. Examples of the additive include surfactants. As the surfactant, the same surfactants as those described above can be mentioned, a non-ionic surfactant is preferable, and a non-ionic fluorine surfactant or a non-ionic silicon surfactant is more preferable.

When a surfactant is added, the amount thereof based on the total amount of the rinse liquid is generally 0.001 to 5% by weight, preferably 0.005 to 2% by weight, and more preferably 0.01 to 0.5% by weight.

The rinse treatment using a rinse liquid (washing treatment) can be conducted by a conventional rinse method. Examples of the rinse method include a method in which the rinse liquid is continuously applied to the substrate while rotating it at a constant rate (rotational coating method), a method in which the substrate is immersed in the rinse liquid for a predetermined time (dip method), and a method in which the rinse liquid is sprayed onto the surface of the substrate (spray method).

According to the method of forming a resist pattern of the present embodiment described above, since the resist composition according to the first aspect described above is used, a resist pattern having good lithography properties and a high rectangularity may be formed with high sensitivity.

EXAMPLES

As follows is a description of examples of the present invention, although the scope of the present invention is by no way limited by these examples.

Synthesis Example 1

[Synthesis of Polymeric Compound (A-1)]

10.0 g of monomer (a10-1pre), 13.1 g of monomer (a0-1-1) and 2.4 g of dimethyl-2,2'-azobisisoutyrate (V-601) as a polymerization initiator were dissolved in 50.0 g of methyl ethyl ketone (MEK), followed by heating to 85° C. in a nitrogen atmosphere, and stirring for 5 hours. Then, 9.4 g of acetic acid and 160 g of methanol was added to the reaction liquid, and a deprotection reaction was conducted at 30° C. for 8 hours. After the reaction finished, the obtained reaction liquid was washed by precipitating in 2,500 g of heptane. The obtained white solid was subjected to filtration, followed by drying under reduced pressure for one night, so as to obtain 12.0 g of a polymeric compound (A-1) as an objective compound.

[Chemical Formula 77]

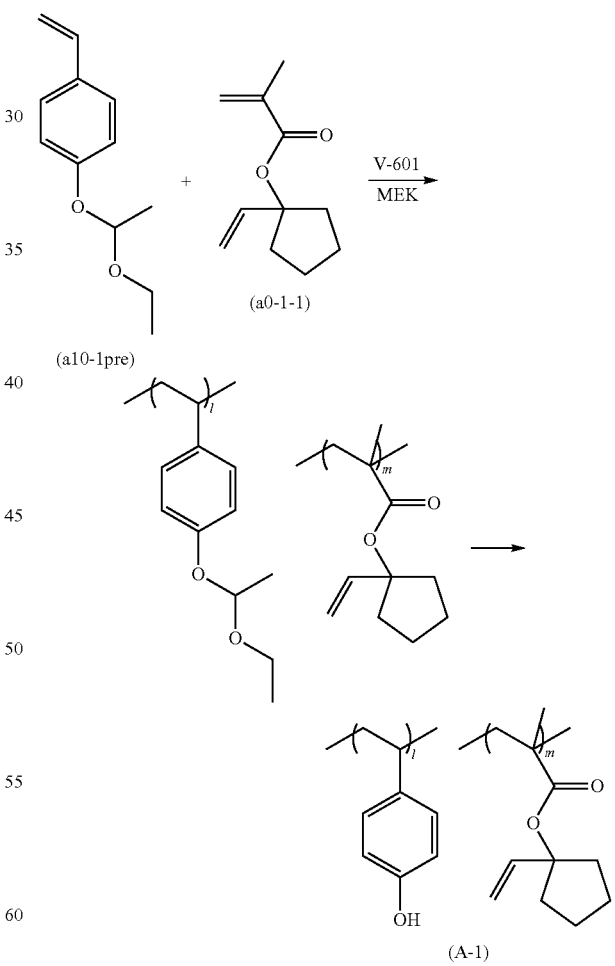

With respect to the polymeric compound (A-1), the weight average molecular weight (Mw) and the polydispersity (Mw/Mn) were determined by the polystyrene equivalent value as measured by gel permeation chromatography (GPC). As a result, it was found that the weight average molecular weight was 6,800, and the polydispersity was 1.67. The composition of the copolymer (ratio (molar ratio) of the respective structural units within the structural formula) as determined by $^{13}$C-NMR was l/m=50/50.

Synthesis Examples 2 to 23

Using the following compounds, polymeric compounds (A-2) to (A-23) having the compositional ratio indicated in Table 1 were synthesized in the same manner.

With respect to each polymeric compound, the compositional ratio of the polymers (the molar ratio of the respective structural units in the polymeric compound) as determined by $^{13}$C-NMR, the weight average molecular weight (Mw) and the polydispersity (Mw/Mn) determined by the polystyrene equivalent value as measured by GPC are also shown in Table 1.

[Chemical Formula 78]

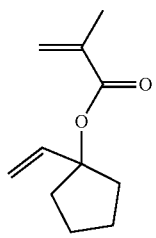
(a0-1-1)

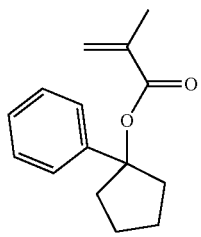
(a0-1-2)

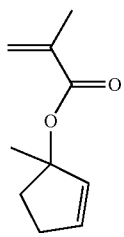
(a0-1-3)

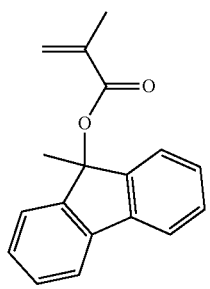
(a0-1-4)

-continued

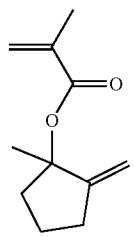
(a0-1-5)

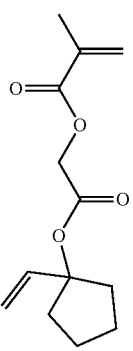
(a0-1-6)

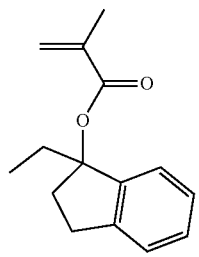
(a0-1-7)

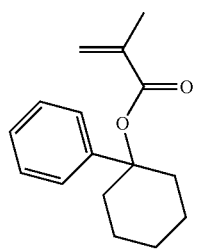
(a0-1-8)

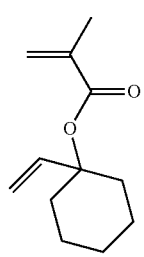
(a0-1-9)

[Chemical Formula 79]
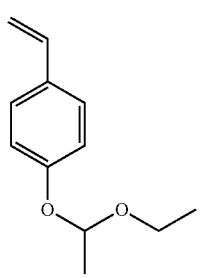
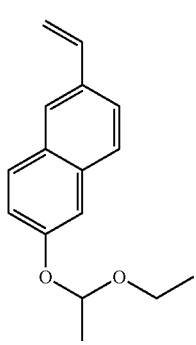
[Chemical Formula 80]
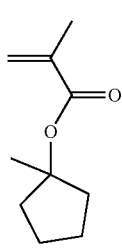 (a1-1)
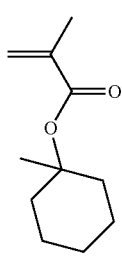 (a1-2)
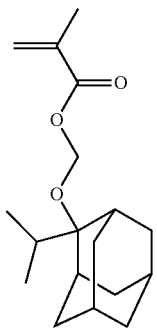 (a1-3)
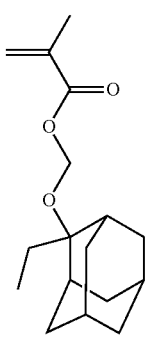 (a1-4)
[Chemical Formula 81]
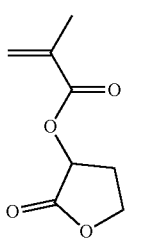 (a2-1)
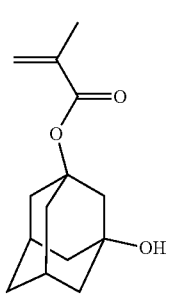 (a3-1)
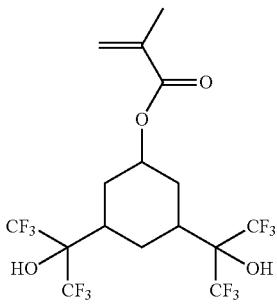 (a3-2)
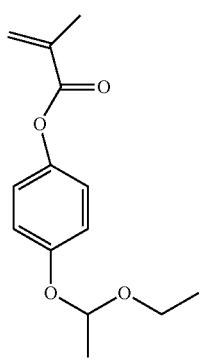 (a10-3pre)
(a10-1pre)
(a10-2pre)
Polymeric compounds (A-1) to (A-23) obtained by the above synthesis examples are shown below.

[Chemical Formula 82]
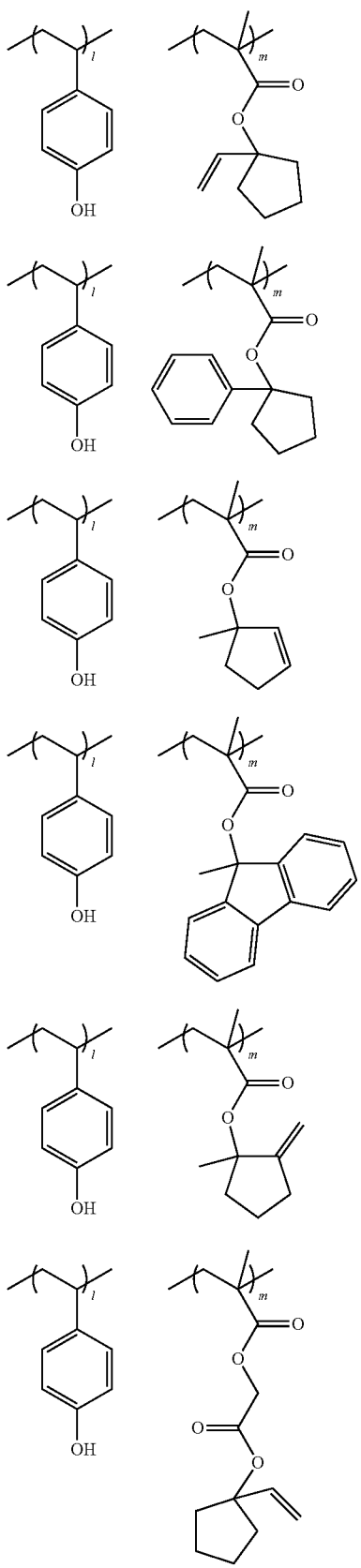
[Chemical Formula 83]
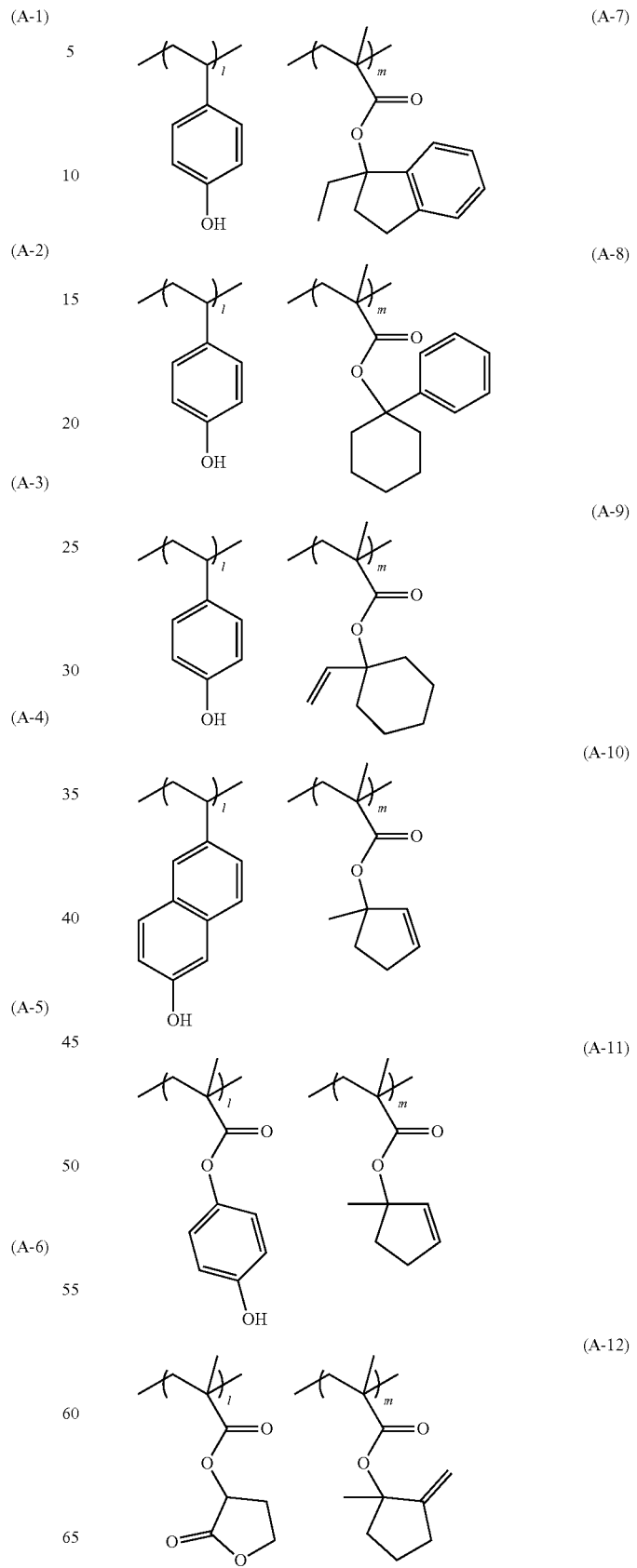

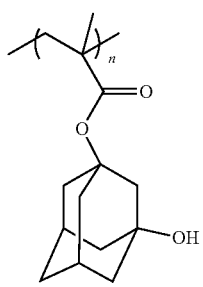
[Chemical Formula 84]
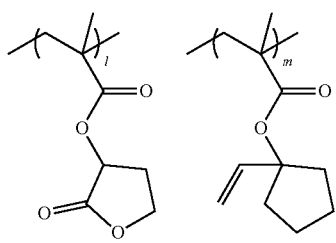
(A-13)
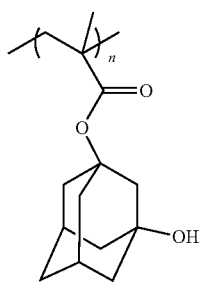
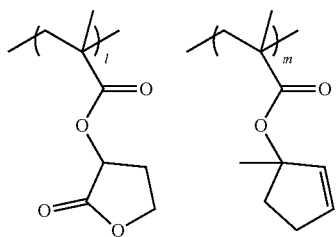
(A-14)
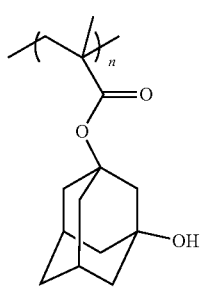
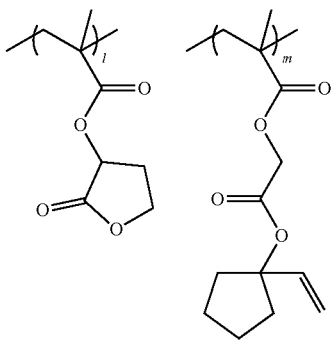
(A-15)
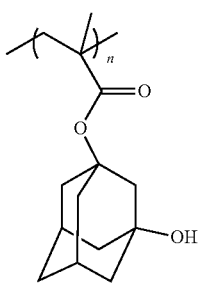
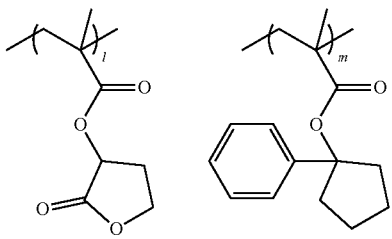
(A-16)
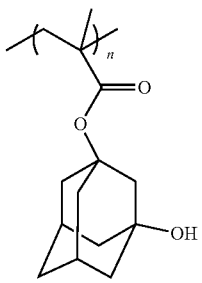
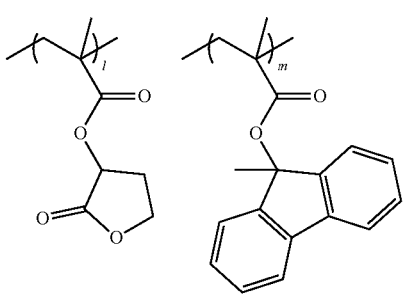
(A-17)

-continued

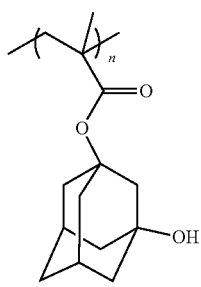

[Chemical Formula 85]

(A-18)

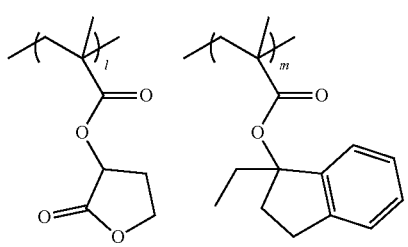

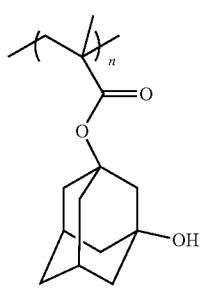

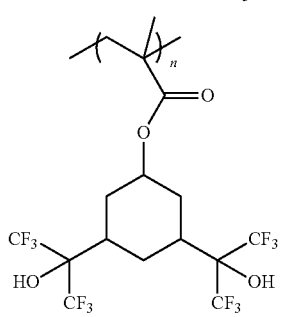

-continued

[Chemical Formula 86]

(A-20)

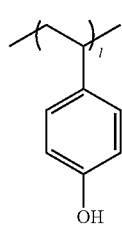 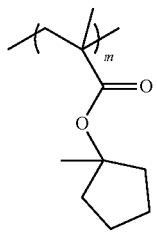

(A-21)

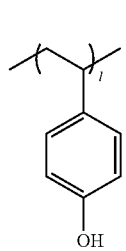 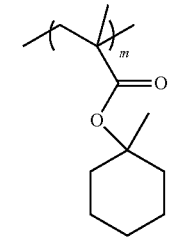

(A-22)

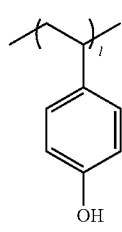 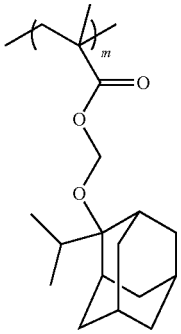

(A-19)

(A-23)

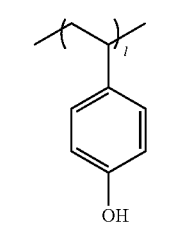

The structural unit represented by chemical formula (a10-1) shown below, the structural unit represented by chemical formula (a10-2) shown below and the structural unit represented by chemical formula (a10-3) shown below which constitute the above copolymers are obtained by copolymerizing the monomer represented by the aforementioned chemical formula (a10-1pre), the monomer represented by the aforementioned chemical formula (a10-2pre) and the monomer represented by the aforementioned chemical formula (a10-3pre), respectively.

[Chemical Formula 87]

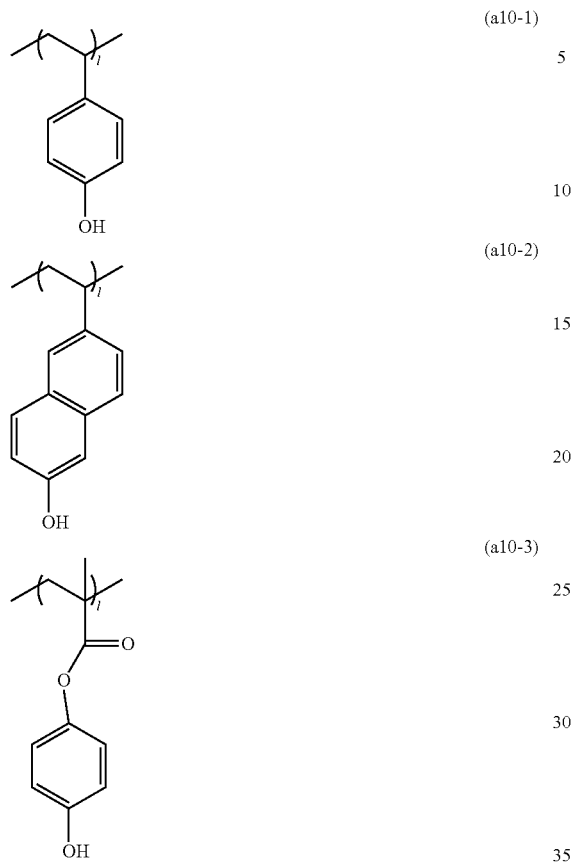

(a10-1)

(a10-2)

(a10-3)

TABLE 1

| | Polymeric compound | Copolymer compositional ratio of polymeric compound (molar ratio) | Weight average molecular weight (Mw) | Polydispersity (Mw/Mn) |
|---|---|---|---|---|
| Synthesis Example 1 | (A-1) | (a10-1)/(a0-1-1) = 50/50 | 6800 | 1.67 |
| Synthesis Example 2 | (A-2) | (a10-1)/(a0-1-2) = 50/50 | 7200 | 1.71 |
| Synthesis Example 3 | (A-3) | (a10-1)/(a0-1-3) = 50/50 | 6700 | 1.71 |
| Synthesis Example 4 | (A-4) | (a10-1)/(a0-1-4) = 50/50 | 6700 | 1.72 |
| Synthesis Example 5 | (A-5) | (a10-1)/(a0-1-5) = 50/50 | 6700 | 1.71 |
| Synthesis Example 6 | (A-6) | (a10-1)/(a0-1-6) = 50/50 | 7000 | 1.72 |
| Synthesis Example 7 | (A-7) | (a10-1)/(a0-1-7) = 60/40 | 7000 | 1.71 |
| Synthesis Example 8 | (A-8) | (a10-1)/(a0-1-8) = 50/50 | 7100 | 1.72 |
| Synthesis Example 9 | (A-9) | (a10-1)/(a0-1-9) = 50/50 | 6800 | 1.66 |
| Synthesis Example 10 | (A-10) | (a10-2)/(a0-1-3) = 50/50 | 6600 | 1.68 |
| Synthesis Example 11 | (A-11) | (a10-3)/(a0-1-3) = 50/50 | 6900 | 1.69 |
| Synthesis Example 12 | (A-12) | (a2-1)/(a0-1-5)/(a3-1) = 30/60/10 | 7000 | 1.71 |
| Synthesis Example 13 | (A-13) | (a2-1)/(a0-1-1)/(a3-1) = 30/60/10 | 7000 | 1.64 |

TABLE 1-continued

| Polymeric compound | Copolymer compositional ratio of polymeric compound (molar ratio) | Weight average molecular weight (Mw) | Polydispersity (Mw/Mn) |
|---|---|---|---|
| Synthesis Example 14 | (A-14) | (a2-1)/(a0-1-3)/(a3-1) = 30/60/10 | 6900 | 1.64 |
| Synthesis Example 15 | (A-15) | (a2-1)/(a0-1-6)/(a3-1) = 30/60/10 | 6800 | 1.67 |
| Synthesis Example 16 | (A-16) | (a2-1)/(a0-1-2)/(a3-1) = 30/60/10 | 6800 | 1.62 |
| Synthesis Example 17 | (A-17) | (a2-1)/(a0-1-4)/(a3-1) = 30/60/10 | 6600 | 1.69 |
| Synthesis Example 18 | (A-18) | (a2-1)/(a0-1-7)/(a3-1) = 30/60/10 | 6800 | 1.65 |
| Synthesis Example 19 | (A-19) | (a2-1)/(a0-1-4)/(a3-2) = 30/60/10 | 6700 | 1.70 |
| Synthesis Example 20 | (A-20) | (a10-1)/(a1-1) = 50/50 | 7000 | 1.72 |
| Synthesis Example 21 | (A-21) | (a10-1)/(a1-2) = 50/50 | 7300 | 1.68 |
| Synthesis Example 22 | (A-22) | (a10-1)/(a1-3) = 50/50 | 6700 | 1.63 |
| Synthesis Example 23 | (A-23) | (a10-1)/(a1-4) = 50/50 | 6900 | 1.70 |

<Production of Resist Composition>

Examples 1 to 23, Comparative Examples 1 to 5

The components shown in Tables 2 to 4 were mixed together and dissolved to obtain each resist composition.

TABLE 2

| | Component (A) | Component (B) | Component (D) | Component (S) |
|---|---|---|---|---|
| Example 1 | (A)-1 [100] | (B1)-1 [15] | (D0)-1 [5] | (S)-1 [6000] |
| Example 2 | (A)-2 [100] | (B1)-1 [15] | (D0)-1 [5] | (S)-1 [6000] |
| Example 3 | (A)-3 [100] | (B1)-1 [15] | (D0)-1 [5] | (S)-1 [6000] |
| Example 4 | (A)-4 [100] | (B1)-1 [15] | (D0)-1 [5] | (S)-1 [6000] |
| Example 5 | (A)-5 [100] | (B1)-1 [15] | (D0)-1 [5] | (S)-1 [6000] |
| Example 6 | (A)-6 [100] | (B1)-1 [15] | (D0)-1 [5] | (S)-1 [6000] |
| Example 7 | (A)-7 [100] | (B1)-1 [15] | (D0)-1 [5] | (S)-1 [6000] |
| Example 8 | (A)-8 [100] | (B1)-1 [15] | (D0)-1 [5] | (S)-1 [6000] |
| Example 9 | (A)-9 [100] | (B1)-1 [15] | (D0)-1 [5] | (S)-1 [6000] |
| Example 10 | (A)-10 [100] | (B1)-1 [15] | (D0)-1 [5] | (S)-1 [6000] |
| Example 11 | (A)-11 [100] | (B1)-1 [15] | (D0)-1 [5] | (S)-1 [6000] |

TABLE 3

| | Component (A) | Component (B) | Component (D) | Component (S) |
|---|---|---|---|---|
| Example 12 | (A)-12 [100] | (B1)-1 [15] | (D0)-1 [5] | (S)-1 [6000] |
| Example 13 | (A)-13 [100] | (B1)-1 [15] | (D0)-1 [5] | (S)-1 [6000] |
| Example 14 | (A)-14 [100] | (B1)-1 [15] | (D0)-1 [5] | (S)-1 [6000] |
| Example 15 | (A)-15 [100] | (B1)-1 [15] | (D0)-1 [5] | (S)-1 [6000] |
| Example 16 | (A)-16 [100] | (B1)-1 [15] | (D0)-1 [5] | (S)-1 [6000] |
| Example 17 | (A)-17 [100] | (B1)-1 [15] | (D0)-1 [5] | (S)-1 [6000] |
| Example 18 | (A)-18 [100] | (B1)-1 [15] | (D0)-1 [5] | (S)-1 [6000] |
| Example 19 | (A)-19 [100] | (B1)-1 [15] | (D0)-1 [5] | (S)-1 [6000] |
| Example 20 | (A)-1 [100] | (B1)-1 [15] | (D0)-2 [5] | (S)-1 [6000] |
| Example 21 | (A)-1 [100] | (B1)-1 [15] | (D0)-3 [5] | (S)-1 [6000] |
| Example 22 | (A)-1 [100] | (B1)-1 [15] | (D0)-4 [5] | (S)-1 [6000] |
| Example 23 | (A)-1 [100] | (B1)-1 [15] | (D0)-5 [5] | (S)-1 [6000] |

TABLE 4

| | Component (A) | Component (B) | Component (D) | Component (S) |
|---|---|---|---|---|
| Comparative Example 1 | (A)-1 [100] | (B1)-1 [15] | (D1)-1 [5] | (S)-1 [6000] |
| Comparative Example 2 | (A)-20 [100] | (B1)-1 [15] | (D0)-1 [5] | (S)-1 [6000] |
| Comparative Example 3 | (A)-21 [100] | (B1)-1 [15] | (D0)-1 [10] | (S)-1 [6000] |
| Comparative Example 4 | (A)-22 [100] | (B1)-1 [15] | (D0)-1 [5] | (S)-1 [6000] |
| Comparative Example 5 | (A)-23 [100] | (B1)-1 [15] | (D0)-1 [5] | (S)-1 [6000] |

In Tables 2 to 4, the reference characters indicate the following. The values in brackets [ ] indicate the amount (in terms of parts by weight) of the component added.

(A)-1 to (A)-23: the aforementioned polymeric compounds (A-1) to (A-23).

(B1)-1: an acid generator represented by chemical formula (B1-1) shown below

[Chemical Formula 88]

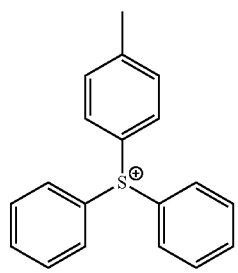

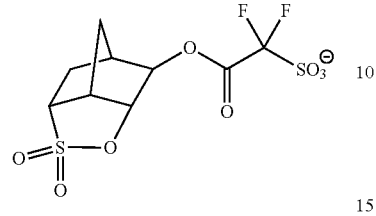
(B1-1)

(D0)-1 to (D0)-5: Acid diffusion control agents consisting of compounds represented by chemical formulae (D0-1) to (D0-5) shown below, respectively.

(D1)-1: Acid diffusion control agent represented by chemical formula (D1-1) shown below.

(S)-1: a mixed solvent of propylene glycol monomethyl ether acetate/propylene glycol monomethyl ether=60/40 (weight ratio).

[Chemical Formula 89]

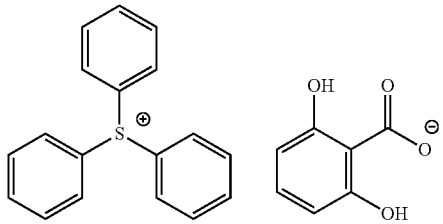
(D0-1)

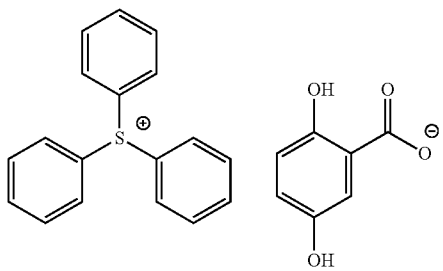
(D0-2)

(D0-3)

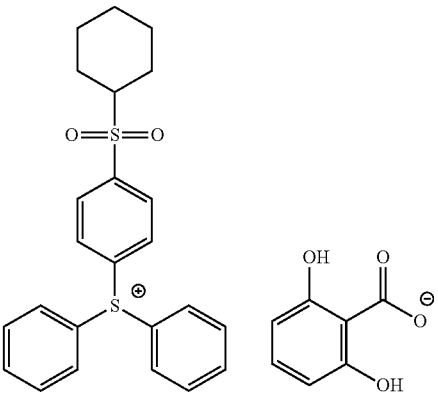
(D0-4)

(D0-5)

[Chemical Formula 90]

(D1-1)

<Formation of Resist Pattern>

Each of the resist compositions of examples and comparative examples was applied to an 8-inch silicon substrate which had been treated with hexamethyldisilazane (HMDS) using a spinner, and was then prebaked (PAB) on a hot plate at 110° C. for 60 seconds and dried, so as to form a resist film having a film thickness of 30 nm.

A drawing (exposure) was carried out on the resist film using an electron beam lithography system JEOL-JBX-9300FS (manufactured by JEOL Ltd.) with acceleration voltage of 100 kV and a target size of 1:1 line-and-space pattern (line width: 50 nm to 16 nm) (hereinafter referred to as an "LS pattern"). Then, a post exposure bake (PEB) treatment was conducted at 90° C. for 60 seconds. Thereafter, alkali developing was conducted for 60 seconds at 23° C. in a 2.38% by weight aqueous solution of tetramethylammonium hydroxide (TMAH) (product name: NMD-3; manufactured by Tokyo Ohka Kogyo Co., Ltd.).

Then, water rinsing was conducted for 15 seconds using pure water.

As a result, a 1:1 LS pattern having a line width of 50 nm to 16 nm was formed.

[Evaluation of Optimum Exposure Dose (Eop)]

The optimum exposure dose Eop (µC/cm²) with which the LS pattern having a target size (line width: 50 nm) was formed in the above "Formation of resist pattern" was determined. The results are indicated under "Eop(µC/cm²)" in Tables 5 to 7.

[Evaluation of Line Width Roughness (LWR)]

With respect to the LS pattern formed in the above "formation of resist pattern", 3σ was determined as a yardstick for indicating LWR. The results are indicated under "LWR (nm)" in Tables 5 to 7.

"3σ" indicates a value of 3 times the standard deviation (σ) (i.e., 3σ) (unit: nm) determined by measuring the line positions at 400 points in the lengthwise direction of the line using a scanning electron microscope (product name: S-9380, manufactured by Hitachi High-Technologies Corporation; acceleration voltage: 800V).

The smaller this 3σ value is, the lower the level of roughness on the side walls of the line, indicating that an LS pattern with a uniform width was obtained.

[Evaluation of Resolution]

The optimum exposure dose Eop (µC/cm²) with which the LS pattern having a target size (line width: 50 nm) was formed in the above "Formation of resist pattern" was determined. When the LS pattern was formed by gradually increasing the exposure dose from the optimum exposure dose Eop, the minimum dimension of the pattern that was resolved without collapsing was determined using a scanning electron microscope S-9380 (manufactured by Hitachi High Technologies Co., Ltd.). The results are indicated under "Resolution (nm)" in Tables 5 to 7.

[Evaluation of LS Pattern Shape]

The cross-sectional shape of the LS pattern formed in the above "Formation of resist pattern" was observed using a scanning electron microscope (product name: SU8000, manufactured by Hitachi High-Technologies Corporation; acceleration voltage: 300V). The shape was evaluated in accordance with the following criteria. The results are indicated under "Pattern shape" in Tables 5 and 7.

A: The cross-sectional shape of the pattern is rectangular, and the perpendicularity is high.

B: The perpendicularity of the cross-sectional shape of the pattern is slightly poor as compared to "A".

C: The cross-sectional shape of the pattern is top-rounding (the top of the pattern is rounded) or has a T-top shape.

TABLE 5

| | PAB (° C.) | PEB (° C.) | Eop [µC/cm²] | LWR [nm] | Resolution [nm] | Pattern shape |
|---|---|---|---|---|---|---|
| Example 1 | 110 | 90 | 87 | 4.4 | 26 | A |
| Example 2 | 110 | 90 | 83 | 4.6 | 26 | A |
| Example 3 | 110 | 90 | 90 | 4.8 | 26 | A |
| Example 4 | 110 | 90 | 88 | 4.8 | 28 | B |
| Example 5 | 110 | 90 | 92 | 4.7 | 28 | B |
| Example 6 | 110 | 90 | 83 | 4.9 | 28 | B |
| Example 7 | 110 | 90 | 84 | 4.8 | 28 | B |
| Example 8 | 110 | 90 | 88 | 4.5 | 26 | A |
| Example 9 | 110 | 90 | 94 | 4.5 | 26 | A |
| Example 10 | 110 | 90 | 89 | 4.7 | 28 | A |
| Example 11 | 110 | 90 | 88 | 4.9 | 28 | B |

TABLE 6

| | PAB (° C.) | PEB (° C.) | Eop [µC/cm²] | LWR [nm] | Resolution [nm] | Pattern shape |
|---|---|---|---|---|---|---|
| Example 12 | 110 | 90 | 92 | 4.6 | 28 | B |
| Example 13 | 110 | 90 | 86 | 4.8 | 28 | B |
| Example 14 | 110 | 90 | 88 | 4.6 | 28 | B |
| Example 15 | 110 | 90 | 90 | 4.7 | 28 | B |
| Example 16 | 110 | 90 | 92 | 4.6 | 28 | B |
| Example 17 | 110 | 90 | 90 | 4.7 | 28 | B |
| Example 18 | 110 | 90 | 86 | 4.8 | 28 | B |
| Example 19 | 110 | 90 | 88 | 4.9 | 28 | B |
| Example 20 | 110 | 90 | 88 | 4.4 | 26 | A |
| Example 21 | 110 | 90 | 87 | 4.5 | 26 | A |
| Example 22 | 110 | 90 | 89 | 4.4 | 26 | A |
| Example 23 | 110 | 90 | 86 | 4.6 | 26 | A |

TABLE 7

| | PAB (° C.) | PEB (° C.) | Eop [µC/cm²] | LWR [nm] | Resolution [nm] | Pattern shape |
|---|---|---|---|---|---|---|
| Comparative Example 1 | 110 | 90 | 114 | 6.9 | 50 | C |
| Comparative Example 2 | 110 | 90 | 127 | 6.6 | 50 | C |
| Comparative Example 3 | 110 | 90 | 133 | 6.4 | 50 | C |
| Comparative Example 4 | 110 | 90 | 125 | 6.5 | 50 | C |
| Comparative Example 5 | 110 | 90 | 128 | 6.6 | 50 | C |

As seen from the results shown in Tables 5 to 7, the resist compositions of examples could form a resist pattern with high sensitivity, reduced roughness, high resolution and high rectangularity of the pattern, as compared to the resist compositions of comparative examples.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. A resist composition which generates acid upon exposure and exhibits changed solubility in a developing solution under action of acid, the resist composition comprising:

a resin component (A1) which exhibits changed solubility in a developing solution under action of acid, an acid generator component (B) which generates acid upon exposure, and a compound (D0) represented by general formula (d0) shown below having a cation moiety and an anion moiety, the resin component (A1) comprising a polymeric compound (A10) having a structural unit (a0) derived from a compound represented by general formula (a0-1) shown below:

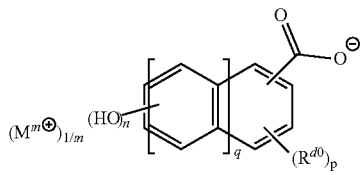
(d0)

wherein $M^{m+}$ represents an m-valent organic cation; m represents an integer of 1 or more, $R^{d0}$ represents a substituent; p represents an integer of 0 to 3; when p is 2 or 3, the plurality of $R^{d0}$ may be the same or different from each other; q represents an integer of 0 to 3; n represents an integer of 2 or more; provided that n+p≤(q×2)+5;

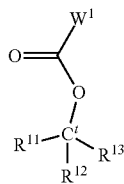
(a0-1)

wherein $W^1$ represents a polymerizable group-containing group; represents a tertiary carbon atom, and the α-position of $C^t$ is a carbon atom which constitutes a carbon-carbon unsaturated bond; $R^{11}$ represents a chain hydrocarbon group; $R^{12}$ and $R^{13}$ each independently represents a chain hydrocarbon group which may have a substituent, or $R^{12}$ and $R^{13}$ are mutually bonded to form a cyclic group which may have a substituent.

2. The resist composition according to claim 1, wherein the compound (DO) is a compound represented by general formula (d0-1) shown below having a cation moiety and an anion moiety:

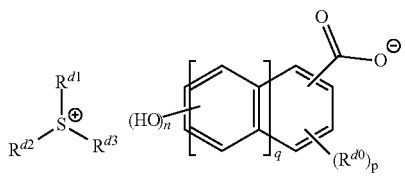
(d0-1)

wherein $R^{d1}$ represents an aryl group which may have a substituent; $R^{d2}$ and $R^{d3}$ each independently represents an aryl group which may have a substituent, or $R^{d2}$ and $R^{d3}$ are mutually bonded to form a ring with the sulfur atom; $R^{d0}$ represents a substituent; p represents an integer of 0 to 3; when p is 2 or 3, the plurality of $R^{d0}$ may be the same or different from each other; q represents an integer of 0 to 3; n represents an integer of 2 or more; provided that n+p≤(q×2)+5.

3. The resist composition according to claim 1, wherein the structural unit (a0) is a structural unit derived from a compound represented by general formula (a0-11) shown below:

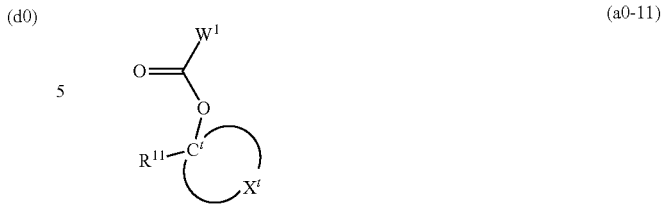
(a0-11)

wherein $W^1$ represents a polymerizable group-containing group; $C^t$ represents a tertiary carbon atom, and the α-position of $C^t$ is a carbon atom which constitutes a carbon-carbon unsaturated bond; $R^{11}$ represents an aromatic hydrocarbon group which may have a substituent, or a chain hydrocarbon group; $X^t$ represents a group which forms a cyclic hydrocarbon group together with $C^t$; provided that part or all of the hydrogen atoms of the cyclic hydrocarbon group may be substituted with a substituent.

4. The resist composition according to claim 1, wherein the amount of the structural unit (a0) based on the combined total (100 mol %) of all structural units constituting the polymeric compound (A10) is 40 to 70 mol %.

5. A method of forming a resist pattern, comprising:

forming a resist film using the resist composition according to claim 1;

exposing the resist film; and developing the exposed resist film to form a resist pattern.

6. The method according to claim 5, wherein the resist film is exposed to extreme ultraviolet (EUV) or electron beam (EB).

7. A resist composition which generates acid upon exposure and exhibits changed solubility in a developing solution under action of acid, the resist composition comprising:

a resin component (A1) which exhibits changed solubility in a developing solution under action of acid, an acid generator component (B) which generates acid upon exposure, and a compound (DO) represented by general formula (d0) shown below having a cation moiety and an anion moiety, the resin component (A1) comprising a polymeric compound (A10) having a structural unit (a0) derived from a compound represented by general formula (a0-11-1) shown below:

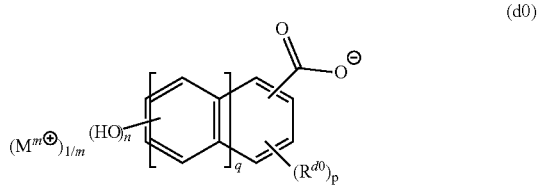
(d0)

wherein $M^{m+}$ represents an m-valent organic cation; m represents an integer of 1 or more, $R^{d0}$ represents a substituent; p represents an integer of 0 to 3; when p is 2 or 3, the plurality of $R^{d0}$ may be the same or different from each other; q represents an integer of 0 to 3; n represents an integer of 2 or more; provided that n+p (q×2)+5;

(a0-11-1)

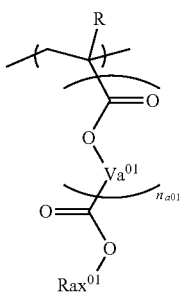

wherein R represents a hydrogen atom, an alkyl group of 1 to 5 carbon atoms or a halogenated alkyl group of 1 to 5 carbon atoms; $Va^{01}$ represents a divalent hydrocarbon group optionally having an ether bond; $n_{a01}$ represents an integer of 0 to 2; $Rax^{01}$ is a group represented by general formula (a0-r-1) shown below, a general formula (a0-r-2) shown below or a group represented by general formula (a0-r-3) shown below:

(a0-r-1)

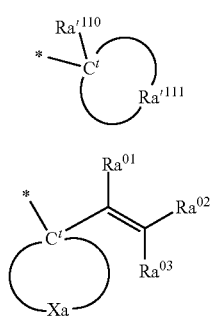

(a0-r-2)

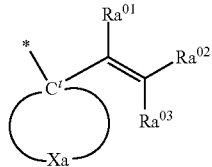

(a0-r-3)

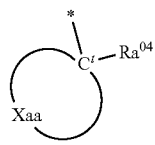

wherein, in formula (a0-r-1), $C^t$ represents a tertiary carbon atom; $Ra'^{110}$ represents a linear or branched alkyl group having 1 to 12 carbon atoms optionally having part thereof substituted with a halogen atom or a hetero atom-containing group; $Ra'^{111}$ is a group which forms a monocyclic alicyclic hydrocarbon group together with $C^t$; provided that part or all of the hydrogen atoms of the monocyclic alicyclic hydrocarbon group may be substituted; provided that, in the monocyclic alicyclic hydrocarbon group, the α-position of $C^t$ is a carbon atom constituting a carbon-carbon unsaturated bond; in formula (a0-r-2), $C^t$ represents a tertiary carbon atom; Xa is a group which forms a monocyclic alicyclic hydrocarbon group together with $C^t$; provided that part or all of the hydrogen atoms of the monocyclic alicyclic hydrocarbon group may be substituted; $Ra^{01}$ to $Ra^{03}$ each independently represents a hydrogen atom, a monovalent saturated chain hydrocarbon group of 1 to 10 carbon atoms or a monovalent saturated aliphatic cyclic hydrocarbon group of 3 to 20 carbon atoms; provided that part or all of the hydrogen atoms of the saturated chain hydrocarbon or the saturated aliphatic cyclic hydrocarbon may be substituted with a substituent; 2 or more of $Ra^{01}$ to $Ra^{03}$ may be mutually bonded to form an aliphatic cyclic structure, but does not form a bridged structure; in formula (a0-r-3), $C^t$ represents a tertiary carbon atoms; Xaa is a group which forms a cyclopentane ring together with $C^t$; provided that part or all of the hydrogen atoms of the monocyclic alicyclic hydrocarbon group may be substituted with a substituent; $Ra^{04}$ represents an aromatic hydrocarbon group which may have a substituent; and * represents a bonding site.

* * * * *